US011220692B2

(12) United States Patent
Gehlsen et al.

(10) Patent No.: US 11,220,692 B2
(45) Date of Patent: Jan. 11, 2022

(54) PICHIA PASTORIS STRAINS FOR PRODUCING PREDOMINANTLY HOMOGENEOUS GLYCAN STRUCTURE

(71) Applicant: Research Corporation Technologies, Inc., Tucson, AZ (US)

(72) Inventors: Kurt R. Gehlsen, Tucson, AZ (US); Thomas G. Chappell, San Marcos, CA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 16/801,466

(22) Filed: Feb. 26, 2020

(65) Prior Publication Data

US 2020/0190526 A1 Jun. 18, 2020

Related U.S. Application Data

(63) Continuation of application No. 16/404,838, filed on May 7, 2019, now Pat. No. 10,612,033, which is a continuation of application No. 15/444,870, filed on Feb. 28, 2017, now Pat. No. 10,329,572, which is a continuation of application No. 14/437,683, filed as application No. PCT/US2013/066335 on Oct. 23, 2013, now Pat. No. 9,617,550.

(60) Provisional application No. 61/717,423, filed on Oct. 23, 2012.

(51) Int. Cl.
*C12N 15/81* (2006.01)
*C12N 9/10* (2006.01)
*C12N 9/24* (2006.01)

(52) U.S. Cl.
CPC ......... *C12N 15/815* (2013.01); *C12N 9/1051* (2013.01); *C12N 9/2488* (2013.01); *C12Y 204/01232* (2013.01); *C12Y 302/0113* (2013.01)

(58) Field of Classification Search
None
See application file for complete search history.

(56) References Cited

U.S. PATENT DOCUMENTS

| | | | |
|---|---|---|---|
| 7,029,872 | B2 | 4/2006 | Gerngross |
| 9,617,550 | B2 | 4/2017 | Gehlsen et al. |
| 10,329,572 | B2 | 6/2019 | Gehlsen et al. |
| 2005/0106664 | A1 | 5/2005 | Contreras et al. |
| 2011/0027831 | A1 | 2/2011 | Hamilton |
| 2012/0029174 | A1 | 2/2012 | Callewaert et al. |
| 2015/0267212 | A1 | 9/2015 | Gehlsen et al. |
| 2017/0166910 | A1 | 6/2017 | Gehlsen et al. |
| 2019/0256860 | A1 | 8/2019 | Gehlsen et al. |

FOREIGN PATENT DOCUMENTS

| | | |
|---|---|---|
| CN | 101484585 A | 7/2009 |
| JP | 2007-511223 A | 5/2007 |
| JP | 2009-536031 A | 10/2009 |
| WO | 2007/130638 A2 | 5/2014 |

OTHER PUBLICATIONS

Becker B. et al., "Short Communication The Transmembrane Domain of Murine α-mannosidase IB is a Major Determinant of Golgi Localization", European J. Cell Biol 79:986-992 (Dec. 2000).
Choi B-K et al., "Use of Combinatorial Genetic Libraries to Humanize N-Linked Glycosylation in the Yeast Pichia Pastoris", PNAS 100(9):5022-5027 (Apr. 29, 2003).
Depoureq K. et al., Engineering of Glycosylation in Yeast and Other Fungi: Current State and Perspectives, Appl Microbiol Biotechnol 87:1617-1631 (2010).
Deschutter K. et al., "Genome Sequence of the Recombinant Protein Production Host Pichia Pastoris", Nat. Biotechnol. 27(6):561-566, Accession No. XP_002489596.1 (Jul. 22, 2009).
Eckart M.R. et al., "Quality and Authenticity of Heterologous Proteins Synthesized in Yeast", Current Opinion in Biotechnology 7:525-530 (1996).
Gonzalez M. et al., "High Abundance of Serine/Threonine-Rich Regions Predicted to Be Hyper-O-Glycosylated in the Secretory Proteins Coded By Eight Fungal Genomes", BMC Microbiology 12(213):1-10 (2012).
Gonzalez D. et al., "The α-Mannosidases: Phylogeny and Adaptive Diversification", Mol Biol Evolution 17(2):292-300 (2000).
Harris S. et al., "Localization of a Yeast Early Golgi Mannosyltransferase, Och1p, Involves Retrograde Transport", The Journal of Cell Biology 132(6):985-998 (Mar. 1996).
Herscovics A., "Structure and Function of Class I α1,2-Mannosidases Involved in Glycoprotein Synthesis and Endoplasmic Reticulum Quality Control", Biochimie 83:757-762 (2001).
Herscovics A. et al., "Isolation of a Mouse Golgi Mannosidease cDNA, a Member of a Gene Family Conserved from Yeast to Mammals", J. Biol. Chem. 269(13):9864-9871 (Apr. 1994).
Jacobs P. et al., "Engineering Complex-Type N-Glycosylation in Pichia Pastoris Using GlycoSwitch Technology", Nature Protocols 4(1):58-70 (2009).
Kitajima T. et al., "*Saccharomyces cerevisiae* α1,6-Mannosyltransferase Has a Catalytic potential to Transfer a Second Mannose Molecule", The FEBS Journal 273:5074-5085, 273 (2006).

(Continued)

*Primary Examiner* — Paul J Holland
(74) *Attorney, Agent, or Firm* — Scully, Scott, Murphy & Presser, P.C.

(57) ABSTRACT

Disclosed herein are novel *Pichia pastoris* strains for expression of exogenous proteins with substantially homogeneous N-glycans. The strains are genetically engineered to include a mutant OCH1 allele which is transcribed into an mRNA coding for a mutant OCH1 gene product (i.e., α-1,6-mannosyltransferase, or "OCH1 protein"). The mutant OCH1 protein contains a catalytic domain substantially identical to that of the wild type OCH1 protein, but lacks an N-terminal sequence necessary to target the OCH1 protein to the Golgi apparatus. The strains disclosed herein are robust, stable, and transformable, and the mutant OCH1 allele and the ability to produce substantially homogeneous N-glycans are maintained for generations after rounds of freezing and thawing and after subsequent transformations.

8 Claims, 12 Drawing Sheets

Specification includes a Sequence Listing.

(56) References Cited

OTHER PUBLICATIONS

Kim M. et al., "Functional Characterization of the Hansenula polymorpha HOC1, OCH1, and OCR1 Genes as Members of the Yeast OCH1 Mannosyltransferase Family Involved in Protein Glycosylation", J. Biol. Chem. 281(10):6261-6272 (Mar. 2006).

Lal A. et al., "Isolation and Expression of Murine and Rabbit cDNAs Encoding an αI,2-Mannosidase Involved in the Processing of Asparagine-Linked Oligosaccharides", J. Biol. Chem. 269(13):9872-9881 (Apr. 1994).

Laroy W. et al., "Glycome Mapping on DNA Sequencing Equipment", Nature Protocols 1(1):397-405 (2006).

Maras M. et al., "Molecular Cloning and Enzymatic Characterization of a Trichoderma Reesei 1,2-α-D-Mannosidase" J. Biotechnol. 77:255-263 (2000).

Nakayama K. et al., "OCH1 Encodes a Novel Membrane Bound Mannosyltransferase: Outer Chain Elongation of Asparagines-Linked Oligosaccharides", EMBO Journal 11(7):2511-2519 (1992).

Nett J. et al., "A combinatorial Genetic Library Approach to Target Heterologous Glycosylation Enzymes to the Endoplasmic Reticulum or the Golgi Apparatus of Pichia Pastoris", Yeast 28:237-252 (2011).

Romero P. et al., "Glycoprotein Biosynthesis in *Saccharomyces cerevisiae*. Partial Purification of the α-1,6-Mannosyltransferase That Initiates Outer Chain Synthesis", Glycobiology 4(2):135-140 (1994).

Schneikert J. et al., "Characterization of a Noel Mouse Recombinant Processing α-Mannosidase", Glycobiology 4(4):445-450 (1994).

Tremblay L. et al., "Molecular cloning, chromosomal mapping and tissue-specific expression of a novel human α1,2-mannosidase gene involved in N-glycan maturation", Glycobiology 8(6):585-595 (1998).

Tu L. et al., "Localization of Golgi-Resident Glycosyltransferases" Cell. Mol. Life Sci. 67:29-41 (2010).

Verostek M. F. et al., "Mannosyltransferase Activites in Membranes From Various Yeast Strains", Glycobiology 5(7):671-681 (1995).

Wiggins S.A.R. et al., "Activity of the Yeast MNN1 α 1,3-Mannosyltransferase Requires a Motif Conserved in Many Other Families of Glycosyltransferases", Proc. Natl. Acad. Sci. USA 95:7945-7950 (Jul. 1998).

Yoko-O T. et al., "Schizosaccharomyces Pombe och1+ Encodes α-1,6-Mannosyltransferase that is Involved in Outer Chain Elongation of N-Linked Oligosaccharides", FEBS Letters 489:75-80 (2001).

International Search Report dated Feb. 20, 2014 received in International Application No. PCT/US 2013/066335.

Chinese Office Action dated May 3, 2016 received in Chinese Application No. 201380055395.9, together with an English-language translation.

Extended Supplementary European Search Report dated May 18, 2016 received in European Application No. 13 84 9948.8.

Japanese Notice of Reasons for Rejection dated Aug. 23, 2017 received in Japanese Application No. 2015-539748, together with an English-language translation.

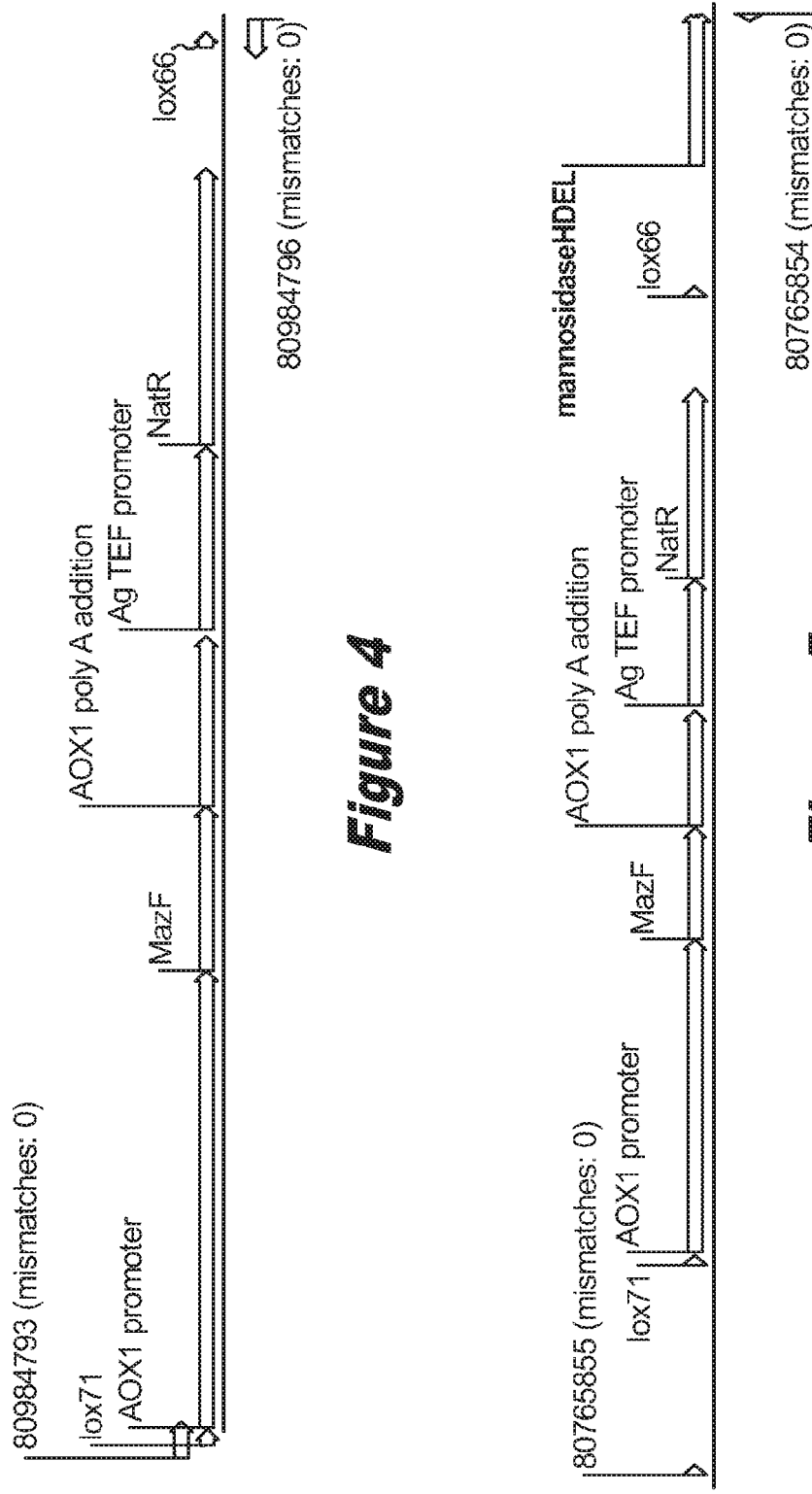

The filled circles (●) refers to the commercial Herceptin produced by CHO cells, the filled squares (■) refers to Man5-type trastuzumab.

SEQUENCE LISTING

<160> NUMBER OF SEQ ID NOS: 93

<210> SEQ ID NO 1
<211> LENGTH: 9865
<212> TYPE: DNA
<213> ORGANISM: Artificial Sequence
<220> FEATURE:
<223> OTHER INFORMATION: Synthetic Nucleotide

<400> SEQUENCE: 1

| | | | | | |
|---|---|---|---|---|---|
| aacgtcaaag | acagcaatgg | agtcaatatt | gataacacca | ctggcagagc | ggttcgtacg | 60 |
| tcgttttgga | gccgatatga | ggctcagcgt | gctaacagca | cgattgacaa | gaagactctc | 120 |
| gagtgacagt | aggttgagta | aagtattcgc | ttagattccc | aaccttcgtt | ttattctttc | 180 |
| gtagacaaag | aagctgcatg | cgaacatagg | gacaactttt | ataaatccaa | ttgtcaaacc | 240 |
| aacgtaaaac | cctctggcac | cattttcaac | atatatttgt | gaagcagtac | gcaatatcga | 300 |
| taaatactca | ccgttgtttg | taacagcccc | aacttgcata | cgccttctaa | tgacctcaaa | 360 |
| tggataagcc | gcagcttgtg | ctaacatacc | agcagcaccg | cccgcggtca | gctgcgccca | 420 |
| cacatataaa | ggcaatctac | gatcatggga | ggaattagtt | ttgaccgtca | ggtcttcaag | 480 |
| agttttgaac | tcttcttctt | gaactgtgta | accttttaaa | tgacgggatc | taaatacgtc | 540 |
| atggatgaga | tcatgtgtgt | aaaaactgac | tccagcatat | ggaatcattc | caaagattgt | 600 |
| aggagcgaac | ccacgataaa | agtttcccaa | ccttgccaaa | gtgtctaatg | ctgtgacttg | 660 |
| aaatctgggt | tcctcgttga | agaccctgcg | tactatgccc | aaaaactttc | ctccacgagc | 720 |
| cctattaact | tctctatgag | tttcaaatgc | caaacggaca | cggattaggt | ccaatgggta | 780 |
| agtgaaaaac | acagagcaaa | ccccagctaa | tgagccggcc | agtaaccgtc | ttggagctgt | 840 |
| ttcataagag | tcattaggga | tcaataacgt | tctaatctgt | tcataacata | caaattttat | 900 |
| ggctgcatag | ggaaaaattc | tcaacagggt | agccgaatga | ccctgatata | gacctgcgac | 960 |
| accatcatac | ccatagatct | gcctgacagc | cttaaagagc | ccgctaaaag | acccggaaaa | 1020 |
| ccgagagaac | tctggattag | cagtctgaaa | aagaatcttc | actctgtcta | gtggagcaat | 1080 |
| taatgtctta | gcggcacttc | ctgctactcc | gccagctact | cctgaataga | tcacatactg | 1140 |
| caaagactgc | ttgtcgatga | ccttgggggtt | atttagcttc | aagggcaatt | tttgggacat | 1200 |
| tttggacaca | ggagactcag | aaacagacac | agagcgttct | gagtcctggt | gctcctgacg | 1260 |
| taggcctaga | acaggaatta | ttggctttat | ttgtttgtcc | atttcatagg | cttggggtaa | 1320 |
| tagatagatg | acagagaaat | agagaagacc | taatattttt | tgttcatggc | aaatcgcggg | 1380 |
| ttcgcggtcg | ggtcacacac | ggagaagtaa | tgagaagagc | tggtaatctg | ggtaaaagg | 1440 |
| gttcaaaaga | aggtcgcctg | gtagggatgc | aatacaaggt | tgtcttggag | tttacattga | 1500 |
| ccagatgatt | tggcttttc | tctgttcaat | tcacattttt | cagcgagaat | cggattgacg | 1560 |
| gagaaatggc | ggggtgtggg | gtggatagat | ggcagaaatg | ctcgcaatca | ccgcgaaaga | 1620 |
| aagactttat | ggaatagaac | tactgggtgg | tgtaaggatt | acatagctag | tccaatggag | 1680 |
| tccgttggaa | aggtaagaag | aagctaaaac | cggctaagta | actagggaag | aatgatcaga | 1740 |
| ctttgatttg | atgaggtctg | aaaatactct | gctgcttttt | cagttgcttt | ttccctgcaa | 1800 |
| cctatcattt | tccttttcat | aagcctgcct | tttctgtttt | cacttatatg | agttccgccg | 1860 |
| agacttcccc | aaattctctc | ctggaacatt | ctctatcgct | ctccttccaa | gttgcgcccc | 1920 |
| ctggcactgc | ctagtaatat | taccacgcga | cttatattca | gttccacaat | ttccagtgtt | 1980 |
| cgtagcaaat | atcatcagcc | taccgttcgt | atagcataca | ttatacgaac | ggtacttttt | 2040 |
| tgtagaaatg | tcttggtgtc | ctcgtccaat | caggtagcca | tctctgaaat | atctggctcc | 2100 |
| gttgcaactc | cgaacgacct | gctggcaacg | taaaattctc | cggggtaaaa | cttaaatgtg | 2160 |
| gagtaatgga | accagaaacg | tctcttccct | tctctctcct | tccaccgccc | gttaccgtcc | 2220 |

```
ctaggaaatt ttactctgct ggagagcttc ttctacggcc cccttgcagc aatgctcttc    2280
ccagcattac gttgcgggta aaacggaggt cgtgtacccg acctagcagc ccagggatgg    2340
aaaagtcccg gccgtcgctg gcaataatag cgggcggacg catgtcatga gattattgga    2400
aaccaccaga atcgaatata aaaggcgaac acctttccca attttggttt ctcctgaccc    2460
aaagacttta aatttaattt atttgtccct atttcaatca attgaacaac tatttcgcga    2520
aacgatgaga tttccttcaa tttttactgc tgttttattc gcagcatcct ccgcattagc    2580
tgctccagtc aacactacaa cagaagatga aacggcacaa attccggctg aagctgtcat    2640
cggttactca gatttagaag gggatttcga tgttgctgtt ttgccatttt ccaacagcac    2700
aaataacggg ttattgttta taaatactac tattgccagc attgctgcta aagaagaagg    2760
ggtatctctc gagaaaagag aggctgaagc tgaattcgcc acaaaacgtg gatctcccaa    2820
ccctacgagg gcggcagcag tcaaggccgc attccagacg tcgtggaacg cttaccacca    2880
tttgcctttt ccccatgacg acctccaccc ggtcagcaac agctttgatg atgagagaaa    2940
cggctggggc tcgtcggcaa tcgatggctt ggacacggct atcctcatgg gggatgccga    3000
cattgtgaac acgatccttc agtatgtacc gcagatcaac ttcaccacga ctgcggttgc    3060
caaccaaggc atctccgtgt tcgagaccaa cattcggtac ctcggtggcc tgctttctgc    3120
ctatgacctg ttgcgaggtc cttttcagctc cttggcgaca aaccagaccc tggtaaacag    3180
ccttctgagg caggctcaaa cactggccaa cggcctcaag gttgcgttca ccactcccag    3240
cggtgtcccg gaccctaccg tcttcttcaa ccctactgtc cggagaagtg gtgcatctag    3300
caacaacgtc gctgaaattg gaagcctggt gctcgagtgg acacggttga gcgacctgac    3360
gggaaacccg cagtatgccc agcttgcgca agggcgag tcgtatctcc tgaatccaaa    3420
gggaagcccg gaggcatggc ctggcctgat tggaacgttt gtcagcacga gcaacggtac    3480 cttcaggat agcagcggca gctggtccgg cctcatggac agcttctacg agtacctgat    3540
caagatgtac ctgtacgacc cggttgcgtt tgcacactac aaggatcgct gggtccttgc    3600
tgccgactcg accattgcgc atctcgcctc tcacccgtcg acgcgcaagg acttgacctt    3660
tttgtcttcg tacaacggac agtctacgtc gccaaactca ggacatttgg ccagttttgc    3720
cggtggcaac ttcatcttgg gaggcattct cctgaacgag caaaagtaca ttgactttgg    3780
aatcaagctt gccagctcgt actttgccac gtacaaccag acggcttctg gaatcggccc    3840
cgaaggcttc gcgtgggtgg acagcgtgac gggcgccggc ggctcgccgc cctcgtccca    3900
gtccgggttc tactcgtcgg caggattctg ggtgacggca ccgtattaca tcctgcggcc    3960
ggagacgctg gagagcttgt actacgcata ccgcgtcacg gcgactcca gtggcagga    4020 cctggcgtgg gaagcgttca gtgccattga ggacgcatgc cgcgccggca gcgcgtactc    4080
gtccatcaac gacgtgacgc aggccaacgg cggggtgcc tctgacgata tggagagctt    4140
ctggtttgcc gaggcgctca gtatgcgta cctgatcttt gcggaggagt cggatgtgca    4200
ggtgcaggcc aacggcggga acaaatttgt ctttaacacg gaggcgcacc cctttagcat    4260
ccgttcatca tcacgacggg gcggccacct tgctcacgac gagttgtaat ctaggcggc    4320 cgccagcttg ggcccgaaca aaaactcatc tcagaagagg atctgaatag cgccgtcgac    4380
catcatcatc atcatcattg agttttagcc ttagacatga ctgttcctca gttcaagttg    4440
ggcacttacg agaagaccgg tcttgctaga ttcaatcaa gaggatgtca gaatgccatt    4500
tgcctgagag atgcaggctt catttttgat acttttttat ttgtaaccta tatagtatag    4560 gattttttt gtcatttgt ttcttctcgt acgagcttgc tcctgatcag cctatctcgc    4620
```

```
agctgatgaa tatcttgtgg tagggqtttg ggaaaatcat tcgagtttga tgttttcctt   4680
ggtatttccc actcctcttc agagtacaga agattaagtg agaccttcgt tgtgcggat    4740
cccccacaca ccatagcttc aaaatgtttc tactccttt ttactcttcc agattttctc    4800
ggactccgcg catcgccgta ccacttcaaa acacccaagc acagcatact aaatttcccc   4860
tctttcttcc tctagggtgt cgttaattac ccgtactaaa ggtttggaaa agaaaaaaga   4920
gaccgcctcg tttcttttc ttcgtcgaaa aaggcaataa aaattttat cacgtttctt     4980
tttcttgaaa atttttttt ttgattttt tctctttcga tgacctccca ttgatattta     5040
agttaataaa cggtcttcaa tttctcaagt ttcagtttca tttttcttgt tctattacaa   5100
cttttttac ttcttgctca ttagaaagaa agcatagcaa tctaatctaa gggcggtgtt    5160
gacaattaat catcggcata gtatatcggc atagtataat acgacaaggt gaggaactaa   5220
accatggcca agcctttgtc tcaagaagaa tccaccctca ttgaaagagc aacggctaca   5280
atcaacagca tccccatctc tgaagactac agcgtcgcca gcgcagctct ctctagcgac   5340
ggccgcatct tcactggtgt caatgtatat catttactg ggggaccttg tgcagaactc     5400
gtggtgctgg gcactgctgc tgctgcggca gctggcaacc tgacttgtat cgtcgcgatc   5460
ggaaatgaga acagggcat cttgagcccc tgcggacggt gccgacaggt gcttctcgat    5520
ctgcatcctg ggatcaaagc catagtgaag gacagtgatg gacagccgac ggcagttggg   5580
attcgtgaat tgctgccctc tggttatgtg tgggagggct aagcacttcg tggccgagga   5640
gcaggactga cacgtccgac gcggcccgac gggtccgagg cctcggagat ccgtcccct    5700
tttcctttgt cgatatcatg taattagtta tgtcacgctt acattcacgc cctcccccca   5760
catccgctct aaccgaaaag gaaggagtta gacaacctga agtctaggtc cctatttatt   5820
tttttatagt tatgttagta ttaagaacgt tatttatatt tcaaattttt ctttttttc    5880
tgtacagacg cgtgtacgca tgtaacatta tactgaaaac cttgcttgag aaggttttgg   5940
gacgctcgaa ggctttaatt tgcaagctgg agaccaacat gtgagcaaaa ggccagcaaa   6000
aggccaggaa ccgtaaaaag gccgcgttgc tggcgttttt ccataggctc cgcccccctg   6060
acgagcatca caaaaatcga cgctcaagtc agaggtggcg aaacccgaca ggactataaa   6120
gataccaggc gtttccccct ggaagctccc tcgtgcgctc tcctgttccg accctgccgc   6180
ttaccggata ccctgtccgcc tttctccctt cgggaagcgt ggcgctttct catagctcac  6240
gctgtaggta tctcagttcg gtgtaggtcg ttcgctccaa gctgggctgt gtgcacgaac   6300
ccccccgttca gcccgaccgc tgcgccttat ccggtaacta tcgtcttgag tccaacccgg  6360
taagacacga cttatcgcca ctggcagcag ccactggtaa caggattagc agagcgaggt   6420
atgtaggcgg tgctacagag ttcttgaagt ggtggcctaa ctacggctac actagaagaa   6480
cagtatttgg tatctgcgct ctgctgaagc cagttacctt cggaaaaaga gttggtagct   6540
cttgatccgg caaacaaacc accgctggta gcggtggttt ttttgtttgc aagcagcaga   6600
ttacgcgcag aaaaaaagga tctcaagaag atcctttgat cttttctacg gggtctgacg   6660
ctcagtggaa cgaaaactca cgttaaggga ttttggtcat gagatcagat ctaacatcca   6720
taatcgtatt cgccgtttct gtcatttgcg ttttgtacgg accctcacaa caattatcat   6780
ctccaaaaat agactatgat ccattgacgc tccgatcact tgatttgaag actttggaag   6840
ctccttcaca gttgagtcca ggcaccgtag aagataatct tcgaagacaa ttggagtttc   6900
attttcctta ccgcagttac gaaccttttc cccaacatat ttggcaaacg tggaaagttt   6960
```

```
ctccctctga tagttccttt ccgaaaaact tcaaagactt aggtgaaagt tggctgcaaa      7020
ggtccccaaa ttatgatcat tttgtgatac ccgatgatgc agcatgggaa cttattcacc      7080
atgaatacga acgtgtacca gaagtcttgg aagctttcca cctgctacca gagcccattc      7140
taaaggccga ttttttcagg tatttgattc tttttgcccg tggaggactg tatgctgaca      7200
tggacactat gttattaaaa ccaatagaat cgtggctgac tttcaatgaa actattggtg      7260
gagtaaaaaa caatgctggg ttggtcattg gtattgaggc tgatcctgat agacctgatt      7320
ggcacgactg gtatgctaga aggatacaat tttgccaatg gcaattcag tccaaacgag       7380
gacacccagc actgcgtgaa ctgattgtaa gagttgtcag cacgacttta cggaaagaga      7440
aaagcggtta cttgaacatg gtggaaggaa aggatcgtgg aagtgatgtg atggactgga      7500
cgggtccagg aatatttaca gacactctat tgattatat gactaatgtc aatacaacag        7560
gccactcagg ccaaggaatt ggagctggct cagcgtatta caatgcctta tcgttggaag      7620
aacgtgatgc cctctctgcc cgcccgaacg gagagatgtt aaaagagaaa gtcccaggta      7680
aatatgcaca gcaggttgtt ttatgggaac aatttaccaa cctgcgctcc cccaaattaa      7740
tcgacgatat tcttattctt ccgatcacca gcttcagtcc agggattggc acagtggag       7800
ctggagattt gaaccatcac cttgcatata ttaggcatac atttgaagga agttggaagg      7860
actaaagaaa gctagagtaa aatagatata gcgagattag agaatgaata ccttcttcta      7920
agcgatcgtc cgtcatcata gaatatcatg gactgtatag tttttttttt gtacatataa      7980
tgattaaacg gtcatccaac atctcgttga cagatctctc agtacgcgaa atccctgact      8040
atcaaagcaa gaaccgatga agaaaaaaac aacagtaacc caaacaccac aacaaacact      8100
ttatcttctc ccccccaaca ccaatcatca aagagatgtc ggaaccaaac accaagaagc      8160
aaaaactaac cccatataaa aacatcctgg tagataatgc tggtaacccg ctctccttcc      8220
atattctggg ctacttcacg aagtctgacc ggtctcagtt gatcaacatg atcctcgaaa      8280
tgggtggcaa gatcgttcca gacctgcctc ctctggtaga tggagtgttg ttttgacag       8340
gggattacaa gtctattgat gaagataccc taaagcaact gggggacgtt ccaatataca      8400
gagactcctt catctaccag tgttttgtgc acaagacatc tcttcccatt gacactttcc      8460
gaattgacaa gaacgtcgac ttggctcaag atttgatcaa tagggccctt caagagtctg      8520
tggatcatgt cacttctgcc agcacagctg cagctgctgc tgttgttgtc gctaccaacg      8580
gcctgtcttc taaaccagac gctcgtacta gcaaaataca gttcactccc gaagaagatc      8640
gttttattct tgactttgtt aggagaaatc ctaaacgaag aaacacacat caactgtaca      8700
ctgagctcgc tcagcacatg aaaaaccata cgaatcattc tatccgccac agatttcgtc      8760
gtaatctttc cgctcaactt gattgggttt atgatatcga tccattgacc aaccaacctc      8820
gaaaagatga aaacgggaac tacatcaagg tacaagatct tccacaagga attcgtggtc      8880
attattctgc ccaagatgat tacaatttgt gtttatcggt tcaaccttc attgaatctg       8940
tagatgagac aacaggccaa gaatttttca aacctctgaa aggtgtattt gatgacttgg      9000
aatctcgctt tcctcaccat acaaagactt cctggagaga cagattcaga aagtttgcct      9060
ctaaatacgg tgttcgtcag tacatcgcgt attatgaaaa gactgttgaa ctcaatggtg      9120
ttcctaatcc gatgacgaac tttacctcaa aggcttccat tgaaaaattt agagaaagac      9180
gcgggacttc acgtaacagt ggccttccag gcccggttgg tgtagaagct gtaagctctt      9240
tggaccacat atccccattg gtcacatcta attccaattc tgcagctgct gcagctgctg      9300
ccgcagcagt tgcagcctct gcctctgctt cttcagctcc taatacttca actaccaatt      9360
```

-continued

```
tctttgaaca ggagaatatt gcccaagttc tctctgcaca taacaacgag cagtctattg    9420
cagaagttat tgagtccgca cagaatgtca cacccatga aagtgaacct atagctgatc    9480
atgttcgaaa aaatcttaca gacgatgaat tgcttgacaa aatggatgat attttaagct    9540
ccagaagtct aggcggacta gatgacttga taaagatcct ctacactgag ctgggatttg    9600
ctcatcgtta taccgaattt cttttttacct catgttctgg tgatgtgatt ttcttccgac    9660
cattagtgga acatttcctt cttactggtg agtgggagct ggagaatact cgtggcatct    9720
ggaccggtcg tcaagacgaa atgctacgtg ctagcaatct agatgacctg cacaagttaa    9780
ttgacctgca tgggaaagaa cgtgttgaga ccagaagaaa agccatcaag ggagaatgat    9840
cataagaaat gaaaaacgta taagt                                          9865
```

<210> SEQ ID NO 2
<211> LENGTH: 404
<212> TYPE: PRT
<213> ORGANISM: Pichia pastoris

<400> SEQUENCE: 2

```
Met Ala Lys Ala Asp Gly Ser Leu Leu Tyr Tyr Asn Pro His Asn Pro
1               5                   10                  15

Pro Arg Arg Tyr Tyr Phe Tyr Met Ala Ile Phe Ala Val Ser Val Ile
            20                  25                  30

Cys Val Leu Tyr Gly Pro Ser Gln Gln Leu Ser Ser Pro Lys Ile Asp
        35                  40                  45

Tyr Asp Pro Leu Thr Leu Arg Ser Leu Asp Leu Lys Thr Leu Glu Ala
    50                  55                  60

Pro Ser Gln Leu Ser Pro Gly Thr Val Glu Asp Asn Leu Arg Arg Gln
65                  70                  75                  80

Leu Glu Phe His Phe Pro Tyr Arg Ser Tyr Glu Pro Phe Pro Gln His
                85                  90                  95

Ile Trp Gln Thr Trp Lys Val Ser Pro Ser Asp Ser Ser Phe Pro Lys
            100                 105                 110

Asn Phe Lys Asp Leu Gly Glu Ser Trp Leu Gln Arg Ser Pro Asn Tyr
        115                 120                 125

Asp His Phe Val Ile Pro Asp Asp Ala Ala Trp Glu Leu Ile His His
    130                 135                 140

Glu Tyr Glu Arg Val Pro Glu Val Leu Glu Ala Phe His Leu Leu Pro
145                 150                 155                 160

Glu Pro Ile Leu Lys Ala Asp Phe Phe Arg Tyr Leu Ile Leu Phe Ala
                165                 170                 175

Arg Gly Leu Tyr Ala Asp Met Asp Thr Met Leu Leu Lys Pro Ile
            180                 185                 190

Glu Ser Trp Leu Thr Phe Asn Glu Thr Ile Gly Gly Val Lys Asn Asn
        195                 200                 205

Ala Gly Leu Val Ile Gly Ile Glu Ala Asp Pro Asp Arg Pro Asp Trp
    210                 215                 220

His Asp Trp Tyr Ala Arg Arg Ile Gln Phe Cys Gln Trp Ala Ile Gln
225                 230                 235                 240

Ser Lys Arg Gly His Pro Ala Leu Arg Glu Leu Ile Val Arg Val Val
                245                 250                 255

Ser Thr Thr Leu Arg Lys Glu Lys Ser Gly Tyr Leu Asn Met Val Glu
            260                 265                 270

Gly Lys Asp Arg Gly Ser Asp Val Met Asp Trp Thr Gly Pro Gly Ile
```

```
            275                 280                 285
Phe Thr Asp Thr Leu Phe Asp Tyr Met Thr Asn Val Asn Thr Thr Gly
    290                 295                 300

His Ser Gly Gln Gly Ile Gly Ala Gly Ser Ala Tyr Tyr Asn Ala Leu
305                 310                 315                 320

Ser Leu Glu Glu Arg Asp Ala Leu Ser Ala Arg Pro Asn Gly Glu Met
                325                 330                 335

Leu Lys Glu Lys Val Pro Gly Lys Tyr Ala Gln Gln Val Val Leu Trp
            340                 345                 350

Glu Gln Phe Thr Asn Leu Arg Ser Pro Lys Leu Ile Asp Asp Ile Leu
        355                 360                 365

Ile Leu Pro Ile Thr Ser Phe Ser Pro Gly Ile Gly His Ser Gly Ala
    370                 375                 380

Gly Asp Leu Asn His His Leu Ala Tyr Ile Arg His Thr Phe Glu Gly
385                 390                 395                 400

Ser Trp Lys Asp

<210> SEQ ID NO 3
<211> LENGTH: 388
<212> TYPE: PRT
<213> ORGANISM: Pichia pastoris

<400> SEQUENCE: 3

Met Arg Ser Asp Leu Thr Ser Ile Ile Val Phe Ala Val Ser Val Ile
1               5                   10                  15

Cys Val Leu Tyr Gly Pro Ser Gln Gln Leu Ser Ser Pro Lys Ile Asp
            20                  25                  30

Tyr Asp Pro Leu Thr Leu Arg Ser Leu Asp Leu Lys Thr Leu Glu Ala
        35                  40                  45

Pro Ser Gln Leu Ser Pro Gly Thr Val Glu Asp Asn Leu Arg Arg Gln
    50                  55                  60

Leu Glu Phe His Phe Pro Tyr Arg Ser Tyr Glu Pro Phe Pro Gln His
65                  70                  75                  80

Ile Trp Gln Thr Trp Lys Val Ser Pro Ser Asp Ser Ser Phe Pro Lys
                85                  90                  95

Asn Phe Lys Asp Leu Gly Glu Ser Trp Leu Gln Arg Ser Pro Asn Tyr
            100                 105                 110

Asp His Phe Val Ile Pro Asp Asp Ala Ala Trp Glu Leu Ile His His
        115                 120                 125

Glu Tyr Glu Arg Val Pro Glu Val Leu Glu Ala Phe His Leu Leu Pro
    130                 135                 140

Glu Pro Ile Leu Lys Ala Asp Phe Phe Arg Tyr Leu Ile Leu Phe Ala
145                 150                 155                 160

Arg Gly Gly Leu Tyr Ala Asp Met Asp Thr Met Leu Leu Lys Pro Ile
                165                 170                 175

Glu Ser Trp Leu Thr Phe Asn Glu Thr Ile Gly Gly Val Lys Asn Asn
            180                 185                 190

Ala Gly Leu Val Ile Gly Ile Glu Ala Asp Pro Asp Arg Pro Asp Trp
        195                 200                 205

His Asp Trp Tyr Ala Arg Arg Ile Gln Phe Cys Gln Trp Ala Ile Gln
    210                 215                 220

Ser Lys Arg Gly His Pro Ala Leu Arg Glu Leu Ile Val Arg Val Val
225                 230                 235                 240

Ser Thr Thr Leu Arg Lys Glu Lys Ser Gly Tyr Leu Asn Met Val Glu
```

```
                245                 250                 255
Gly Lys Asp Arg Gly Ser Asp Val Met Asp Trp Thr Gly Pro Gly Ile
            260                 265                 270

Phe Thr Asp Thr Leu Phe Asp Tyr Met Thr Asn Val Asn Thr Thr Gly
            275                 280                 285

His Ser Gly Gln Gly Ile Gly Ala Gly Ser Ala Tyr Tyr Asn Ala Leu
            290                 295                 300

Ser Leu Glu Glu Arg Asp Ala Leu Ser Ala Arg Pro Asn Gly Glu Met
305                 310                 315                 320

Leu Lys Glu Lys Val Pro Gly Lys Tyr Ala Gln Gln Val Val Leu Trp
                325                 330                 335

Glu Gln Phe Thr Asn Leu Arg Ser Pro Lys Leu Ile Asp Asp Ile Leu
            340                 345                 350

Ile Leu Pro Ile Thr Ser Phe Ser Pro Gly Ile Gly His Ser Gly Ala
            355                 360                 365

Gly Asp Leu Asn His His Leu Ala Tyr Ile Arg His Thr Phe Glu Gly
            370                 375                 380

Ser Trp Lys Asp
385

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

Ala Lys Ala Asp Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Ala Lys Ala Asp Gly Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Ala Lys Ala Asp Gly Ser Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

Ala Lys Ala Asp Gly Ser Leu Leu
```

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Ala Lys Ala Asp Gly Ser Leu Leu Tyr
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 9

Ala Lys Ala Asp Gly Ser Leu Leu Tyr Tyr
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 10

Met Ala Lys Ala Asp Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Met Ala Lys Ala Asp Gly Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

Met Ala Lys Ala Asp Gly Ser Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Met Ala Lys Ala Asp Gly Ser Leu Leu
1               5

```
<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 14

Met Ala Lys Ala Asp Gly Ser Leu Leu Tyr
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 15

Met Ala Lys Ala Asp Gly Ser Leu Leu Tyr Tyr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 16

Met Ala Lys Ala Asp Gly Ser Leu Leu Tyr Tyr Asn
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 17

Met Ala Lys Ala Asp Gly Ser Leu Leu Tyr Tyr Asn Pro
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 18

Met Ala Lys Ala Asp Gly Ser Leu Leu Tyr Tyr Asn Pro His
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

Met Ala Lys Ala Asp Gly Ser Leu Leu Tyr Tyr Asn Pro His Asn
1               5                   10                  15
```

```
<210> SEQ ID NO 20
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 20

Met Ala Lys Ala Asp Gly Ser Leu Leu Tyr Tyr Asn Pro His Asn Pro
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 21

Met Ala Lys Ala Asp Gly Ser Leu Leu Tyr Tyr Asn Pro His Asn Pro
1               5                   10                  15

Pro

<210> SEQ ID NO 22
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 22

Met Ala Lys Ala Asp Gly Ser Leu Leu Tyr Tyr Asn Pro His Asn Pro
1               5                   10                  15

Pro Arg

<210> SEQ ID NO 23
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 23

Met Ala Lys Ala Asp Gly Ser Leu Leu Tyr Tyr Asn Pro His Asn Pro
1               5                   10                  15

Pro Arg Arg

<210> SEQ ID NO 24
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 24

Met Ala Lys Ala Asp Gly Ser Leu Leu Tyr Tyr Asn Pro His Asn Pro
1               5                   10                  15

Pro Arg Arg Tyr
            20

<210> SEQ ID NO 25
<211> LENGTH: 21
<212> TYPE: PRT
<213> ORGANISM: Artificial Sequence
```

```
<220> FEATURE:
<223> OTHER INFORMATION: Synthetic Peptide

<400> SEQUENCE: 25

Met Ala Lys Ala Asp Gly Ser Leu Leu Tyr Tyr Asn Pro His Asn Pro
 1               5                  10                  15

Pro Arg Arg Tyr Tyr
            20

<210> SEQ ID NO 26
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 26

Ala Lys Ala Asp Gly Ser Leu Leu Tyr Tyr Asn Pro His Asn Pro Pro
 1               5                  10                  15

Arg Arg Tyr Tyr Phe Tyr Met Ala
            20

<210> SEQ ID NO 27
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 27

Met Ala Lys Ala Asp Gly Ser Leu Leu Tyr Tyr Asn Pro His Asn Pro
 1               5                  10                  15

Pro Arg Arg Tyr Tyr Phe Tyr Met Ala
            20                  25

<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 28

Arg Ser Asp Leu Thr Ser Ile Ile Val
 1               5

<210> SEQ ID NO 29
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 29
gcgaaggcag atggc                                                    15

<210> SEQ ID NO 30
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 30
gcgaaggcag atggcagt                                                 18
```

<210> SEQ ID NO 31
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 31
gcgaaggcag atggcagttt g                                    21

<210> SEQ ID NO 32
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 32
gcgaaggcag atggcagttt gctc                                 24

<210> SEQ ID NO 33
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 33
gcgaaggcag atggcagttt gctctac                              27

<210> SEQ ID NO 34
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 34
gcgaaggcag atggcagttt gctctactat                           30

<210> SEQ ID NO 35
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 35
atggcgaagg cagatggc                                        18

<210> SEQ ID NO 36
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 36
atggcgaagg cagatggcag t                                    21

<210> SEQ ID NO 37
<211> LENGTH: 24
<212> TYPE: DNA
<213> ORGANISM: Artificial Sequence
<220> FEATURE:

<223> OTHER INFORMATION: Synthetic Oligonucleotide

<400> SEQUENCE: 37
atggcgaagg cagatggcag tttg                                          24

<210> SEQ ID NO 38
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 38
atggcgaagg cagatggcag tttgctc                                       27

<210> SEQ ID NO 39
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 39
atggcgaagg cagatggcag tttgctctac                                    30

<210> SEQ ID NO 40
<211> LENGTH: 30
<212> TYPE: DNA
<213> ORGANISM: Artificial Sequence
<220> FEATURE:
<223> OTHER INFORMATION: Synthetic Oligonucleotide'

<400> SEQUENCE: 40
atggcgaagg cagatggcag tttgctctac                                    30

<210> SEQ ID NO 41
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 41
atggcgaagg cagatggcag tttgctctac tataat                             36

<210> SEQ ID NO 42
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 42
atggcgaagg cagatggcag tttgctctac tataatcct                          39

<210> SEQ ID NO 43
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 43
atggcgaagg cagatggcag tttgctctac tataatcctc ac                      42

```
<210> SEQ ID NO 44
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 44
atggcgaagg cagatggcag tttgctctac tataatcctc ac                        42

<210> SEQ ID NO 45
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 45
atggcgaagg cagatggcag tttgctctac tataatcctc acaatcca                  48

<210> SEQ ID NO 46
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 46
atggcgaagg cagatggcag tttgctctac tataatcctc acaatccacc c              51

<210> SEQ ID NO 47
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 47
atggcgaagg cagatggcag tttgctctac tataatcctc acaatccacc caga           54

<210> SEQ ID NO 48
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 48
atggcgaagg cagatggcag tttgctctac tataatcctc acaatccacc cagaagg        57

<210> SEQ ID NO 49
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 49
atggcgaagg cagatggcag tttgctctac tataatcctc acaatccacc cagaaggtat     60

<210> SEQ ID NO 50
<211> LENGTH: 63
<212> TYPE: DNA
<213> ORGANISM: Artificial Sequence
<220> FEATURE:
<223> OTHER INFORMATION: Synthetic Oligonucleotide
```

<400> SEQUENCE: 50

```
atggcgaagg cagatggcag tttgctctac tataatcctc acaatccacc cagaaggtat    60
tac                                                                  63
```

<210> SEQ ID NO 51
<211> LENGTH: 73
<212> TYPE: DNA
<213> ORGANISM: Artificial Sequence
<220> FEATURE:
<223> OTHER INFORMATION: Synthetic Oligonucleotide

<400> SEQUENCE: 51

```
gcgaaggcag atggcagttt gctctactat aatcctcaca atccacccag aaggtattac    60
ttctacatgg cta                                                       73
```

<210> SEQ ID NO 52
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 52

```
atggcgaagg cagatggcag tttgctctac tataatcctc acaatccacc cagaaggtat    60
tacttctaca tggcta                                                    76
```

<210> SEQ ID NO 53
<211> LENGTH: 10742
<212> TYPE: DNA
<213> ORGANISM: Artificial Sequence
<220> FEATURE:
<223> OTHER INFORMATION: Synthetic Oligonucleotide

<400> SEQUENCE: 53

```
aacgtcaaag acagcaatgg agtcaatatt gataacacca ctggcagagc ggttcgtacg     60
tcgttttgga gccgatatga ggctcagcgt gctaacagca cgattgacaa gaagactctc    120
gagtgacagt aggttgagta agtattcgc ttagattccc aaccttcgtt ttattctttc     180
gtagacaaag aagctgcatg cgaacatagg gacaactttt ataaatccaa ttgtcaaacc    240
aacgtaaaac cctctggcac cattttcaac atatatttgt gaagcagtac gcaatatcga    300
taaatactca ccgttgtttg taacagcccc aacttgcata cgccttctaa tgacctcaaa    360
tggataagcc gcagcttgtg ctaacatacc agcagcaccg cccgcggtca gctgcgccca    420
cacatataaa ggcaatctac gatcatggga ggaattagtt ttgaccgtca ggtcttcaag    480
agttttgaac tcttcttctt gaactgtgta acctttttaaa tgacgggatc taaatacgtc    540
atggatgaga tcatgtgtgt aaaaactgac tccagcatat ggaatcattc caaagattgt    600
aggagcgaac ccacgataaa agtttcccaa ccttgccaaa gtgtctaatg ctgtgacttg    660
aaatctgggt tcctcgttga agaccctgcg tactatgccc aaaaactttc ctccacgagc    720
cctattaact tctctatgag tttcaaatgc caaacggaca cggattaggt ccaatgggta    780
agtgaaaaac acagagcaaa ccccagctaa tgagccggcc agtaaccgtc ttggagctgt    840
ttcataagag tcattaggga tcaataacgt tctaatctgt tcataacata caaatttat     900 ggctgcatag ggaaaaattc tcaacagggt agccgaatga ccctgatata gacctgcgac    960
accatcatac cctagatct gcctgacagc cttaaagagc ccgctaaaag acccggaaaa     1020
ccgagagaac tctggattag cagtctgaaa aagaatcttc actctgtcta gtggagcaat    1080
```

```
taatgtctta gcggcacttc ctgctactcc gccagctact cctgaataga tcacatactg   1140
caaagactgc ttgtcgatga ccttggggtt atttagcttc aagggcaatt tttgggacat   1200
tttggacaca ggagactcag aaacagacac agagcgttct gagtcctggt gctcctgacg   1260
taggcctaga acaggaatta ttggctttat ttgtttgtcc atttcatagg cttggggtaa   1320
tagatagatg acagagaaat agagaagacc taatatttt tgttcatggc aaatcgcggg   1380
ttcgcggtcg ggtcacacac ggagaagtaa tgagaagagc tggtaatctg ggtaaaagg   1440 gttcaaaaga aggtcgcctg gtagggatgc aatacaaggt tgtcttggag tttacattga   1500
ccagatgatt tggcttttc tctgttcaat tcacatttt cagcgagaat cggattgacg   1560
gagaaatggc ggggtgtggg gtggatagat ggcagaaatg ctcgcaatca ccgcgaaaga   1620
aagactttat ggaatagaac tactgggtgg tgtaaggatt acatagctag tccaatggag   1680
tccgttggaa aggtaagaag aagctaaaac cggctaagta actaggaag aatgatcaga    1740 ctttgatttg atgaggtctg aaaatactct gctgctttt cagttgcttt ttccctgcaa   1800
cctatcattt tccttttcat aagcctgcct tttctgtttt cacttatatg agttccgccg   1860
agacttcccc aaattctctc ctggaacatt ctctatcgct ctccttccaa gttgcgcccc   1920
ctggcactgc ctagtaatat taccacgcga cttatattca gttccacaat ttccagtgtt   1980
cgtagcaaat atcatcagcc atggcgaagg cagatggcag tttgctctac tataatcctc   2040
acaatccacc cagaaggtat tacttctaca tggctatatt cgccgtttct gtcatttgcg   2100
ttttgtacgg accctcacaa caattatcat ctccaaaaat agactatgat ccattgacgc   2160
tccgatcact tgatttgaag actttggaag ctccttcaca gttgagtcca ggcaccgtag   2220
aagataatct tcgaagacaa ttggagtttc attttcctta ccgcagttac gaaccttttc   2280
cccaacatat ttggcaaacg tggaaagttt ctccctctga tagttccttt ccgaaaaact   2340
tcaaagactt aggtgaaagt tggctgcaaa ggtccccaaa ttatgatcat tttgtgatac   2400
ccgatgatgc agcatgggaa cttattcacc atgaatacga acgtgtacca gaagtcttgg   2460
aagctctaga tgctcaccgc aatgctgtta aggttcgtat ggagaaactg ggacttattt   2520
aattatttag agatttaac ttacatttag attcgataga tccacaggac gggtgtggtc   2580
gccatgatcg cgtagtcgat agtggctcca agtagcgaag cgagcaggac tgggcggcgg   2640
ccaaagcggt cggacagtgc tccgagaacg ggtgcgcata gaaattgcat caacgcatat   2700
agcgctagca gcacgccata gtgactggcg atgctgtcgg aatggacgat atcccgcaag   2760
aggcccggca gtaccggcat aaccaagcct atgcctacag catccagggt gacggtgccg   2820
aggatgacga tgagcgcatt gttagatttc atacacggtg cctgactgcg ttagcaattt   2880
aactgtgata aactaccgca ttaaagctga tcttttttgt agaaatgtct tggtgtcctc   2940
gtccaatcag gtagccatct ctgaaatatc tggctccgtt gcaactccga acgacctgct   3000
ggcaacgtaa aattctccgg ggtaaaactt aaatgtggag taatgaaacc agaaacgtct   3060
cttcccttct ctctccttcc accgcccgtt accgtcccta ggaaatttta ctctgctgga   3120
gagcttcttc tacggccccc ttgcagcaat gctcttccca gcattacgtt gcgggtaaaa   3180
cggaggtcgt gtacccgacc tagcagccca gggatgaaa agtcccggcc gtcgctggca    3240
ataatagcgg gcggacgcat gtcatgagat tattggaaac caccagaatc gaatataaaa   3300
ggcgaacacc tttcccaatt ttggtttctc ctgacccaaa gactttaaat ttaatttatt   3360
tgtccctatt tcaatcaatt gaacaactat ttcgcgaaac gatgagattt ccttcaattt   3420
```

```
ttactgctgt tttattcgca gcatcctccg cattagctgc tccagtcaac actacaacag    3480
aagatgaaac ggcacaaatt ccggctgaag ctgtcatcgg ttactcagat ttagaagggg    3540
atttcgatgt tgctgttttg ccattttcca acagcacaaa taacgggtta ttgtttataa    3600
atactactat tgccagcatt gctgctaaag aagaaggggt atctctcgag aaaagagagg    3660
ctgaagctga attcgccaca aaacgtggat ctcccaaccc tacgagggcg gcagcagtca    3720
aggccgcatt ccagacgtcg tggaacgctt accaccattt tgccttccc catgacgacc     3780 tccacccggt cagcaacagc tttgatgatg agagaaacgg ctggggctcg tcggcaatcg    3840
atggcttgga cacggctatc ctcatggggg atgccgacat tgtgaacacg atccttcagt    3900
atgtaccgca gatcaacttc accacgactg cggttgccaa ccaaggatcc tccgtgttcg    3960
agaccaacat tcggtacctc ggtggcctgc tttctgccta tgacctgttg cgaggtcctt    4020
tcagctcctt ggcgacaaac cagaccctgg taaacagcct tctgaggcag gctcaaacac    4080
tggccaacgg cctcaaggtt gcgttcacca ctcccagcgg tgtcccggac cctaccgtct    4140
tcttcaaccc tactgtccgg agaagtggtg catctagcaa caacgtcgct gaaattggaa    4200
gcctggtgct cgagtggaca cggttgagcg acctgacggg aaacccgcag tatgcccagc    4260
ttgcgcagaa gggcgagtcg tatctcctga tccaaagggg aagcccggag gcatggcctg    4320
gcctgattgg aacgtttgtc agcacgagca acggtacctt tcaggatagc agcggcagct    4380
ggtccggcct catggacagc ttctacgagt acctgatcaa gatgtacctg tacgacccgg    4440
ttgcgtttgc acactacaag gatcgctggg tccttggtgc cgactcgacc attgggcatc    4500
tcggctctca cccgtcgacg cgcaaggact tgacctttt gtcttcgtac aacgacagt     4560 ctacgtcgcc aaactcagga catttggcca gttttggcgg tggcaacttc atcttgggag    4620
gcattctcct gaacgagcaa aagtacattg actttggaat caagcttgcc agctcgtact    4680
ttggcacgta cacccagacg gcttctggaa tcggccccga aggcttcgcg tgggtggaca    4740
gcgtgacggg cgccggcggc tcgccgccct cgtcccagtc cgggttctac tcgtcggcag    4800
gattctgggt gacggcaccg tattacatcc tgcggccgga gacgctggag agcttgtact    4860
acgcataccg cgtcacgggc gactccaagt ggcaggacct ggcgtgggaa gcgttgagtg    4920
ccattgagga cgcatgccgc gccggcagcg cgtactcgtc catcaacgac gtgacgcagg    4980
ccaacggcgg gggtgcctct gacgatatgg agagcttctg gtttgccgag gcgctcaagt    5040
atgcgtacct gatctttgcg gaggagtcgg atgtgcaggt gcaggccacc ggcgggaaca    5100
aatttgtctt taacacggag gcgcacccct ttagcatccg ttcatcatca cgacggggcg    5160
gccaccttgc tcacgacgag ttgtaatcta gggcggccgc cagcttgggc ccgaacaaaa    5220
actcatctca gaagaggatc tgaatagcgc cgtcgaccat catcatcatc atcattgagt    5280
tttagcctta gacatgactg ttcctcagtt caagttgggc acttacgaga agaccggtct    5340
tgctagattc taatcaagag gatgtcagaa tgccatttgc ctgagagatg caggcttcat    5400
ttttgatact ttttatttg taacctatat agtataggat tttttttgtc attttgtttc    5460
ttctcgtacg agcttgctcc tgatcagcct atctcgcagc tgatgaatat cttgtggtag    5520
gggtttggga aaatcattcg agtttgatgt ttttcttggt atttcccact cctcttcaga    5580
gtacagaaga ttaagtgaga ccttcgtttg tgcggatccc ccacacacca tagcttcaaa    5640
atgtttctac tcctttttta ctcttccaga ttttctcgga ctccgcgcat cgccgtacca    5700
cttcaaaaca cccaagcaca gcatactaaa tttcccctct ttcttcctct agggtgtcgt    5760
taattacccg tactaaaggt ttggaaaaga aaaagagac cgcctcgttt cttttttcttc     5820
```

```
gtcgaaaaag gcaataaaaa ttttatcac gtttctttt cttgaaaatt tttttttg    5880
attttttct ctttcgatga cctcccattg atatttaagt taataaacgg tcttcaattt  5940
ctcaagtttc agtttcattt ttcttgttct attacaactt tttttacttc ttgctcatta  6000
gaaagaaagc atagcaatct aatctaaggg cggtgttgac aattaatcat cggcatagta  6060
tatcggcata gtataatacg acaaggtgag gaactaaacc atggccaagc ctttgtctca  6120
agaagaatcc accctcattg aaagagcaac ggctacaatc aacagcatcc ccatctctga  6180
agactacagc gtcgccagcg cagctctctc tagcgacggc cgcatcttca ctggtgtcaa  6240
tgtatatcat tttactgggg gaccttgtgc agaactcgtg gtgctgggca ctgctgctgc  6300
tgcggcagct ggcaacctga cttgtatcgt cgcgatcgga aatgagaaca ggggcatctt  6360
gagcccctgc ggacggtgcc gacaggtgct tctcgatctg catcctggga tcaaagccat  6420
agtgaaggac agtgatggac agccgacggc agttgggatt cgtgaattgc tgccctctgg  6480
ttatgtgtgg gagggctaag cacttcgtgg ccgaggagca ggactgacac gtccgacgcg  6540
gcccgacggg tccgaggcct cggagatccg tccccctttt cctttgtcga tatcatgtaa  6600
ttagttatgt cacgcttaca ttcacgccct cccccacat ccgctctaac cgaaaaggaa    6660
ggagttagac aacctgaagt ctaggtccct atttatttt ttatagttat gttagtatta    6720
agaacgttat ttatatttca aattttctt ttttttctgt acagacgcgt gtacgcatgt    6780
aacattatac tgaaaacctt gcttgagaag gttttgggac gctcgaaggc tttaatttgc  6840
aagctggaga ccaacatgtg agcaaaaggc cagcaaaagg ccaggaaccg taaaaaggcc  6900
gcgttgctgg cgttttcca taggctccgc ccccctgacg agcatcacaa aaatcgacgc    6960
tcaagtcaga ggtggcgaaa cccgacagga ctataaagat accaggcgtt ccccctgga    7020
agctccctcg tgcgctctcc tgttccgacc ctgccgctta ccggatacct gtccgccttt   7080
ctcccttcgg gaagcgtggc gctttctcaa tgctcacgct gtaggtatct cagttcggtg    7140
taggtcgttc gctccaagct gggctgtgtg cacgaacccc ccgttcagcc cgaccgctgc    7200
gccttatccg gtaactatcg tcttgagtcc aacccggtaa gacacgactt atcgccactg    7260
gcagcagcca ctggtaacag gattagcaga gcgaggtatg taggcggtgc tacagagttc    7320
ttgaagtggt ggcctaacta cggctacact agaaggacag tatttggtat ctgcgctctg    7380
ctgaagccag ttaccttcgg aaaaagagtt ggtagctctt gatccggcaa acaaaccacc    7440
gctggtagcg gtggtttttt tgtttgcaag cagcagatta cgcgcagaaa aaaaggatct    7500
caagaagatc ctttgatctt ttctacgggg tctgacgctc agtggaacga aaactcacgt    7560
taagggattt tggtcatgag atcagatcta acatccataa tcgtattcgc cgtttctgtc    7620
atttgcgttt tgtacggacc ctcacaacaa ttatcatctc caaaaataga ctatgatcca    7680
ttgacgctcc gatcacttga tttgaagact ttggaagctc cttcacagtt gagtccaggc    7740
accgtagaag ataatcttcg aagacaattg gagtttcatt ttccttaccg cagttacgaa    7800
ccttttcccc aacatatttg gcaaacgtgg aaagtttctc cctctgatag ttccttttccg   7860
aaaaacttca aagacttagg tgaaagttgg ctgcaaaggt ccccaaatta tgatcatttt    7920
gtgatacccg atgatgcagc atgggaactt attcaccatg aatacgaacg tgtaccagaa    7980
gtcttggaag ctttccacct gctaccagag cccattctaa aggccgattt tttcaggtat    8040
ttgattcttt ttgcccgtgg aggactgtat gctgacatgg acactatgtt attaaaacca    8100
atagaatcgt ggctgacttt caatgaaact attggtggag taaaaaacaa tgctgggttg    8160
```

```
gtcattggta ttgaggctga tcctgataga cctgattggc acgactggta tgctagaagg   8220
atacaatttt gccaatgggc aattcagtcc aaacgaggac acccagcact gcgtgaactg   8280
attgtaagag ttgtcagcac gactttacgg aaagagaaaa gcggttactt gaacatggtg   8340
gaaggaaagg atcgtggaag tgatgtgatg gactggacgg gtccaggaat atttacagac   8400
actctatttg attatatgac taatgtcaat acaacaggcc actcaggcca aggaattgga   8460
gctggctcag cgtattacaa tgccttatcg ttggaagaac gtgatgccct ctctgcccgc   8520
ccgaacggag agatgttaaa agagaaagtc ccaggtaaat atgcacagca ggttgtttta   8580
tgggaacaat ttaccaacct cgcctccccc aaattaatcg acgatattct tattcttccg   8640
atcaccagct tcagtccagg gattggccac agtggagctg gagatttgaa ccatcacctt   8700
gcatatatta ggcatacatt tgaaggaagt tggaaggact aaagaaagct agagtaaaat   8760
agatatagcg agattagaga atgaatacct tcttctaagc gatcgtccgt catcatagaa   8820
tatcatggac tgtatagttt ttttttttgta catataatga ttaaacggtc atccaacatc   8880
tcgttgacag atctctcagt acgcgaaatc cctgactatc aaagcaagaa ccgatgaaga   8940
aaaaaacaac agtaacccaa acaccacaac aaacacttta tcttctcccc cccaacacca   9000
atcatcaaag agatgtcgga accaaacacc aagaagcaaa aactaacccc atataaaaac   9060
atcctggtag ataatgctgg taacccgctc tccttccata ttctgggcta cttcacgaag   9120
tctgaccggt ctcagttgat caacatgatc ctcgaaatgg gtggcaagat cgttccagac   9180
ctgcctcctc tggtagatgg agtgttgttt ttgacagggg attacaagtc tattgatgaa   9240 gatacccctaa agcaactggg ggacgttcca atatacagag actccttcat ctaccagtgt   9300
tttgtgcaca agacatctct tcccattgac actttccgaa ttgacaagaa cgtcgacttg   9360
gctcaagatt tgatcaatag ggcccttcaa gagtctgtgg atcatgtcac ttctgccagc   9420
acagctgcag ctgctgctgt tgttgtcgct accaacggcc tgtcttctaa accagacgct   9480
cgtactagca aaatacagtt cactcccgaa gaagatcgtt ttattcttga ctttgttagg   9540
agaaatccta acgaagaaa cacacatcaa ctgtacactg agctcgctca gcacatgaaa   9600
aaccatacga atcattctat ccgccacaga tttcgtcgta atctttccgc tcaacttgat   9660
tgggtttatg atatcgatcc attgaccaac caacctcgaa aagatgaaaa cgggaactac   9720
atcaaggtac aagatcttcc acaaggaatt cgtggtcatt attctgccca agatgattac   9780
aatttgtgtt tatcggttca acctttcatt gaatctgtag atgagacaac aggccaagaa   9840
tttttcaaac ctctgaaagg tgtatttgat gacttggaat ctcgctttcc tcaccataca   9900
aagacttcct ggagagacag attcagaaag tttgcctcta aatacggtgt tcgtcagtac   9960
atcgcgtatt atgaaaagac tgttgaactc aatggtgttc ctaatccgat gacgaacttt  10020
acctcaaagg cttccattga aaaatttaga gaaagacgcg ggacttcacg taacagtggc  10080
cttccaggcc cggttggtgt agaagctgta agctctttgg accacatatc cccattggtc  10140
acatctaatt ccaattctgc agctgctgca gctgctgccg cagcagttgc agcctctgcc  10200
tctgcttctt cagctcctaa tacttcaact accaatttct tgaacagga gaatattgcc  10260 caagttctct ctgcacataa caacgagcag tctattgcag aagttattga gtccgcacag  10320
aatgtcaaca cccatgaaag tgaacctata gctgatcatg ttcgaaaaaa tcttacagac  10380
gatgaattgc ttgacaaaat ggatgatatt ttaagctcca gaagtctagg cggactagat  10440
gacttgataa agatcctcta cactgagctg ggatttgctc atcgttatac cgaatttctt  10500
tttacctcat gttctggtga tgtgattttc ttccgaccat tagtggaaca tttccttctt  10560
```

```
actggtgagt gggagctgga gaatactcgt ggcatctgga ccggtcgtca agacgaaatg    10620
ctacgtgcta gcaatctaga tgacctgcac aagttaattg acctgcatgg gaagaaacgt    10680
gttgagacca aagaaaagc catcaaggga gaatgatcat aagaaatgaa aaacgtataa    10740
gt                                                                  10742
```

<210> SEQ ID NO 54
<211> LENGTH: 173
<212> TYPE: PRT
<213> ORGANISM: Artificial Sequence
<220> FEATURE:
<223> OTHER INFORMATION: Synthetic Peptide

<400> SEQUENCE: 54

```
Met Ala Lys Ala Asp Gly Ser Leu Leu Tyr Tyr Asn Pro His Asn Pro
1               5                   10                  15

Pro Arg Arg Tyr Tyr Phe Tyr Met Ala Ile Phe Ala Val Ser Val Ile
                20                  25                  30

Cys Val Leu Tyr Gly Pro Ser Gln Gln Leu Ser Ser Pro Lys Ile Asp
            35                  40                  45

Tyr Asp Pro Leu Thr Leu Arg Ser Leu Asp Leu Lys Thr Leu Glu Ala
        50                  55                  60

Pro Ser Gln Leu Ser Pro Gly Thr Val Glu Asp Asn Leu Arg Arg Gln
65                  70                  75                  80

Leu Glu Phe His Phe Pro Tyr Arg Ser Tyr Glu Pro Phe Pro Gln His
                85                  90                  95

Ile Trp Gln Thr Trp Lys Val Ser Pro Ser Asp Ser Ser Phe Pro Lys
                100                 105                 110

Asn Phe Lys Asp Leu Gly Glu Ser Trp Leu Gln Arg Ser Pro Asn Tyr
            115                 120                 125

Asp His Phe Val Ile Pro Asp Asp Ala Ala Trp Glu Leu Ile His His
        130                 135                 140

Glu Tyr Glu Arg Val Pro Glu Val Leu Glu Ala Leu Asp Ala His Arg
145                 150                 155                 160

Asn Ala Val Lys Val Arg Met Glu Lys Leu Gly Leu Ile
                165                 170
```

<210> SEQ ID NO 55
<211> LENGTH: 522
<212> TYPE: DNA
<213> ORGANISM: Artificial Sequence
<220> FEATURE:
<223> OTHER INFORMATION: Synthetic Oligonucleotide

<400> SEQUENCE: 55

```
atggcgaagg cagatggcag tttgctctac tataatcctc acaatccacc cagaaggtat      60
tacttctaca tggctatatt cgccgtttct gtcatttgcg ttttgtacgg accctcacaa     120
caattatcat ctccaaaaat agactatgat ccattgacgc tccgatcact tgatttgaag     180
actttggaag ctccttcaca gttgagtcca ggcaccgtag aagataatct tcgaagacaa     240
ttggagtttc attttcctta ccgcagttac gaaccttttc cccaacatat ttggcaaacg     300
tggaaagttt ctccctctga tagttccttt ccgaaaaact tcaaagactt aggtgaaagt     360
tggctgcaaa ggtccccaaa ttatgatcat tttgtgatac ccgatgatgc agcatgggaa     420
cttattcacc atgaatacga acgtgtacca gaagtcttgg aagctctaga tgctcaccgc     480
aatgctgtta aggttcgtat ggagaaactg ggacttattt aa                        522
```

<210> SEQ ID NO 56
<211> LENGTH: 388
<212> TYPE: PRT
<213> ORGANISM: Artificial Sequence
<220> FEATURE:
<223> OTHER INFORMATION: Synthetic Peptide

<400> SEQUENCE: 56

```
Met Arg Ser Asp Leu Thr Ser Ile Ile Val Phe Ala Val Ser Val Ile
1               5                   10                  15

Cys Val Leu Tyr Gly Pro Ser Gln Gln Leu Ser Ser Pro Lys Ile Asp
                20                  25                  30

Tyr Asp Pro Leu Thr Leu Arg Ser Leu Asp Leu Lys Thr Leu Glu Ala
            35                  40                  45

Pro Ser Gln Leu Ser Pro Gly Thr Val Glu Asp Asn Leu Arg Arg Gln
        50                  55                  60

Leu Glu Phe His Phe Pro Tyr Arg Ser Tyr Glu Pro Phe Pro Gln His
65                  70                  75                  80

Ile Trp Gln Thr Trp Lys Val Ser Pro Ser Asp Ser Ser Phe Pro Lys
                85                  90                  95

Asn Phe Lys Asp Leu Gly Glu Ser Trp Leu Gln Arg Ser Pro Asn Tyr
                100                 105                 110

Asp His Phe Val Ile Pro Asp Asp Ala Ala Trp Glu Leu Ile His His
            115                 120                 125

Glu Tyr Glu Arg Val Pro Glu Val Leu Glu Ala Phe His Leu Leu Pro
        130                 135                 140

Glu Pro Ile Leu Lys Ala Asp Phe Phe Arg Tyr Leu Ile Leu Phe Ala
145                 150                 155                 160

Arg Gly Gly Leu Tyr Ala Asp Met Asp Thr Met Leu Leu Lys Pro Ile
                165                 170                 175

Glu Ser Trp Leu Thr Phe Asn Glu Thr Ile Gly Gly Val Lys Asn Asn
                180                 185                 190

Ala Gly Leu Val Ile Gly Ile Glu Ala Asp Pro Asp Arg Pro Asp Trp
            195                 200                 205

His Asp Trp Tyr Ala Arg Arg Ile Gln Phe Cys Gln Trp Ala Ile Gln
        210                 215                 220

Ser Lys Arg Gly His Pro Ala Leu Arg Glu Leu Ile Val Arg Val Val
225                 230                 235                 240

Ser Thr Thr Leu Arg Lys Glu Lys Ser Gly Tyr Leu Asn Met Val Glu
                245                 250                 255

Gly Lys Asp Arg Gly Ser Asp Val Met Asp Trp Thr Gly Pro Gly Ile
                260                 265                 270

Phe Thr Asp Thr Leu Phe Asp Tyr Met Thr Asn Val Asn Thr Thr Gly
            275                 280                 285

His Ser Gly Gln Gly Ile Gly Ala Gly Ser Ala Tyr Tyr Asn Ala Leu
        290                 295                 300

Ser Leu Glu Glu Arg Asp Ala Leu Ser Ala Arg Pro Asn Gly Glu Met
305                 310                 315                 320

Leu Lys Glu Lys Val Pro Gly Lys Tyr Ala Gln Gln Val Val Leu Trp
                325                 330                 335

Glu Gln Phe Thr Asn Leu Arg Ser Pro Lys Leu Ile Asp Asp Ile Leu
                340                 345                 350

Ile Leu Pro Ile Thr Ser Phe Ser Pro Gly Ile Gly His Ser Gly Ala
            355                 360                 365
```

Gly Asp Leu Asn His His Leu Ala Tyr Ile Arg His Thr Phe Glu Gly
    370                 375                 380

Ser Trp Lys Asp
385

<210> SEQ ID NO 57
<211> LENGTH: 1167
<212> TYPE: DNA
<213> ORGANISM: Artificial Sequence
<220> FEATURE:
<223> OTHER INFORMATION: Synthetic Oligonucleotide

<400> SEQUENCE: 57

| | | | | | |
|---|---|---|---|---|---|
| atgagatcag | atctaacatc | cataatcgta | ttcgccgttt | ctgtcatttg | cgttttgtac | 60 |
| ggaccctcac | aacaattatc | atctccaaaa | atagactatg | atccattgac | gctccgatca | 120 |
| cttgatttga | agactttgga | agctccttca | cagttgagtc | caggcaccgt | agaagataat | 180 |
| cttcgaagac | aattggagtt | tcattttcct | taccgcagtt | acgaaccttt | tccccaacat | 240 |
| atttggcaaa | cgtggaaagt | ttctccctct | gatagttcct | ttccgaaaaa | cttcaaagac | 300 |
| ttaggtgaaa | gttggctgca | aaggtcccca | aattatgatc | attttgtgat | acccgatgat | 360 |
| gcagcatggg | aacttattca | ccatgaatac | gaacgtgtac | cagaagtctt | ggaagctttc | 420 |
| cacctgctac | cagagcccat | tctaaaggcc | gatttttttca | ggtatttgat | tcttttttgcc | 480 |
| cgtggaggac | tgtatgctga | catggacact | atgttattaa | aaccaataga | atcgtggctg | 540 |
| actttcaatg | aaactattgg | tggagtaaaa | acaatgctgg | ggttggtcat | tggtattgag | 600 |
| gctgatcctg | atagacctga | ttggcacgac | tggtatgcta | gaaggataca | attttgccaa | 660 |
| tgggcaattc | agtccaaacg | aggacaccca | gcactgcgtg | aactgattgt | aagagttgtc | 720 |
| agcacgactt | tacggaaaga | gaaaagcggt | tacttgaaca | tggtggaagg | aaaggatcgt | 780 |
| ggaagtgatg | tgatggactg | gacgggtcca | ggaatatttta | cagacactct | atttgattat | 840 |
| atgactaatg | tcaatacaac | aggccactca | ggccaaggaa | ttggagctgg | ctcagcgtat | 900 |
| tacaatgcct | tatcgttgga | gaacgtgat | gccctctctg | cccgcccgaa | cggagagatg | 960 |
| ttaaaagaga | agtcccagg | taaatatgca | cagcaggttt | ttttatggga | caatttttacc | 1020 |
| aacctgcgct | ccccccaaatt | aatcgacgat | attcttattc | ttccgatcac | cagcttcagt | 1080 |
| ccagggattg | gccacagtgg | agctggagat | ttgaaccatc | accttgcata | tattaggcat | 1140 |
| acatttgaag | gaagttggaa | ggactaa | | | | 1167 |

<210> SEQ ID NO 58
<211> LENGTH: 4311
<212> TYPE: DNA
<213> ORGANISM: Artificial Sequence
<220> FEATURE:
<223> OTHER INFORMATION: Synthetic Oligonucleotide

<400> SEQUENCE: 58

| | | | | | |
|---|---|---|---|---|---|
| ttcgcggtcg | ggtcacacac | ggagaagtaa | tgagaagagc | tggtaatctg | ggtaaaagg | 60 |
| gttcaaaaga | aggtcgcctg | gtagggatgc | aatacaaggt | tgtcttggag | tttacattga | 120 |
| ccagatgatt | tggcttttttc | tctgttcaat | tcacattttt | cagcgagaat | cggattgacg | 180 |
| gagaaatggc | ggggtgtggg | gtggatagat | ggcagaaatg | ctcgcaatca | ccgcgaaaga | 240 |
| aagactttat | ggaatagaac | tactgggtgg | tgtaaggatt | acatagctag | tccaatggag | 300 |
| tccgttggaa | aggtaagaag | aagctaaaac | cggctaagta | actagggaag | aatgatcaga | 360 |

```
ctttgatttg atgaggtctg aaaatactct gctgcttttt cagttgcttt ttccctgcaa    420
cctatcattt tccttttcat aagcctgcct tttctgtttt cacttatatg agttccgccg    480
agacttcccc aaattctctc ctggaacatt ctctatcgct ctccttccaa gttgcgcccc    540
ctggcactgc ctagtaatat taccacgcga cttatattca gttccacaat ttccagtgtt    600
cgtagcaaat atcatcagcc taccgttcgt atagcataca ttatacgaag ttatggatct    660
aacatccaaa gacgaaaggt tgaatgaaac cttttttgcca tccgacatcc acaggtccat    720
tctcacacat aagtgccaaa cgcaacagga ggggatacac tagcagcaga ccgttgcaaa    780
cgcaggacct ccactcctct tctcctcaac acccacttt  gccatcgaaa accagccca    840 gttattgggc ttgattggag ctcgctcatt ccaattcctt ctattaggct actaacacca    900
tgactttatt agcctgtcta tcctggcccc cctggcgagg ttcatgtttg tttatttccg    960
aatgcaacaa gctccgcatt acacccgaac atcactccag atgagggctt tctgagtgtg   1020
gggtcaaata gtttcatgtt ccccaaatgg cccaaaactg acagtttaaa cgctgtcttg   1080
gaacctaata tgacaaaagc gtgatctcat ccaagatgaa ctaagtttgg ttcgttgaaa   1140
tgctaacggc cagttggtca aaagaaact tccaaaagtc ggcataccgt ttgtcttgtt    1200
tggtattgat tgacgaatgc tcaaaaataa tctcattaat gcttagcgca gtctctctat   1260
cgcttctgaa ccccggtgca cctgtgccga aacgcaaatg gggaaacacc cgcttttgg    1320 atgattatgc attgtctcca cattgtatgc ttccaagatt ctggtgggaa tactgctgat   1380
agcctaacgt tcatgatcaa aatttaactg ttctaacccc tacttgacag caatatataa   1440
acagaaggaa gctgccctgt cttaaacctt tttttttatc atcattatta gcttactttc   1500
ataattgcga ctggttccaa ttgacaagct tttgatttta acgactttta acgacaactt   1560
gagaagatca aaaacaact aattattcga acgatggta agccgatacg tacccgatat    1620
gggcgatctg atttggttg atttgaccc gacaaaaggt agcgagcaag ctggacatcg    1680
tccagctgtt gtcctgagtc ctttcatgta caacaacaaa acaggtatgt gtctgtgtgt   1740
tccttgtaca acgcaatcaa aaggatatcc gttcgaagtt gttttatccg gtcaggaacg   1800
tgatggcgta gcgttagctg atcaggtaaa aagtatcgcc tggcgggcaa gaggagcaac   1860
gaagaaagga acagttgccc cagaggaatt acaactcatt aaagccaaaa ttaacgtact   1920
gattgggtaa tcaagaggat gtcagaatgc catttgcctg agatgcag  gcttcatttt    1980 tgatacttt  ttatttgtaa cctatatagt ataggatttt ttttgtcatt ttgtttcttc   2040
tcgtacgagc ttgctcctga tcagcctatc tcgcagctga tgaatatctt gtggtagggg   2100
tttgggaaaa tcattcgagt ttgatgtttt tcttggtatt tcccactcct cttcagagta   2160
cagaagatta agtgacacgt tcgtttgtgc aagcttcaac gatgccaaaa gggtataata   2220
agcgtcattt gcagcattgt gaagaaaact atgtggcaag ccaagcctgc gaagaatgta   2280
gtcgagaatt gagcttgcct cgtccccgcc gggtcacccg gccagcgaca tggaggccca   2340 gaatacccctc cttgacagtc ttgacgtgcg cagctcaggg gcatgatgtg actgtcgccc   2400
gtacatttag cccatacatc cccatgtata atcatttgca tccatacatt ttgatggccg   2460
cacggcgcga agcaaaaatt acggctcctc gctgcagacc tgcgagcagg gaaacgctcc   2520
cctcacagac gcgttgaatt gtcccacgc cgcgcccctg tagagaaata taaaaggtta   2580
ggatttgcca ctgaggttct tctttcatat acttccttt  aaaatcttgc taggatacag   2640
ttctcacatc acatccgaac ataaacaaaa atgaccactt ggatgatac tgcttacaga   2700 tacagaactt ctgttccagg tgatgctgaa gctattgaag ctttggatgg atctttcacc   2760
```

```
actgatactg ttttcagagt cactgctact ggtgatggat tcactttgag agaagttcct    2820
gttgatcctc ctttgaccaa agttttttcct gatgatgaat ctgatgatga atctgatgct   2880
ggtgaagatg gtgatccaga ttctagaact tttgttgctt atggtgatga tggtgatttg    2940
gctggatttg ttgttgtttc ttattctgga tggaacagaa gattgactgt tgaagatatt    3000
gaagttgctc cagaacatag aggtcatggt gttggaagag ctttgatggg attggcaact    3060
gagtttgcca gagaaagagg tgctggtcat ctttggttgg aagtcaccaa tgtcaatgct    3120
ccagctattc atgcttacag aagaatggga ttcactcttt gtggattgga tactgctttg    3180
tatgatggaa ctgcttctga tggagaacaa gctttgtaca tgtccatgcc atgtccttaa    3240
agtaactgac aataaaaaga ttcttgtttt caagaacttg tcatttgtat agttttttta    3300
tattgtagtt gttctatttt aatcaaatgt tagcgtgatt tatattttt ttcgcctcga     3360 catcatctgc ccagatgcga agttaagtgc gcagaaagta atatcatgcg tcaatcgtat    3420
gtgaatgctg gtcgctatac tgctgtcgat tcgatactaa cgccgccatc cagtgtcata    3480
acttcgtata gcatacatta tacgaacggt acttttttgt agaaatgtct tggtgtcctc    3540
gtccaatcag gtagccatct ctgaaatatc tggctccgtt gcaactccga acgacctgct    3600
ggcaacgtaa aattctccgg ggtaaaactt aaatgtggag taatggaacc agaaacgtct    3660
cttcccttct ctctccttcc accgcccgtt accgtcccta ggaaatttta ctctgctgga    3720
gagcttcttc tacggccccc ttgcagcaat gctcttccca gcattacgtt gcgggtaaaa    3780
cggaggtcgt gtacccgacc tagcagccca gggatggaaa agtcccggcc gtcgctggca    3840
ataatagcgg gcggacgcat gtcatgagat tattggaaac caccagaatc gaatataaaa    3900
ggcgaacacc tttcccaatt ttggtttctc ctgacccaaa gactttaaat ttaatttatt    3960
tgtccctatt tcaatcaatt gaacaactat ttcgcgaaac gatgagattt ccttcaatt     4020 ttactgctgt tttattcgca gcatcctccg cattagctgc tccagtcaac actacaacag    4080
aagatgaaac ggcacaaatt ccggctgaag ctgtcatcgg ttactcagat ttagaagggg    4140
atttcgatgt tgctgttttg ccattttcca acagcacaaa taacgggtta ttgtttataa    4200
atactactat tgccagcatt gctgctaaag aagaagggt atctctcgag aaaagagagg    4260
ctgaagctga attcgccaca aaacgtggat ctcccaaccc tacgagggcg g             4311
```

<210> SEQ ID NO 59
<211> LENGTH: 12722
<212> TYPE: DNA
<213> ORGANISM: Artificial Sequence
<220> FEATURE:
<223> OTHER INFORMATION: Synthetic Oligonucleotide

<400> SEQUENCE: 59

```
aacgtcaaag acagcaatgg agtcaatatt gataacacca ctggcagagc ggttcgtacg     60
tcgttttgga gccgatatga ggctcagcgt gctaacagca cgattgacaa gaagactctc    120
gagtgacagt aggttgagta aagtattcgc ttagattccc aaccttcgtt ttattctttc    180
gtagacaaag aagctgcatg cgaacatagg gacaactttt ataaatccaa ttgtcaaacc    240
aacgtaaaac cctctggcac cattttcaac atatatttgt gaagcagtac gcaatatcga    300
taaatactca ccgttgtttg taacagcccc aacttgcata cgccttctaa tgacctcaaa    360
tggataagcc gcagcttgtg ctaacatacc agcagcaccg cccgcggtca gctgcgccca    420
cacatataaa ggcaatctac gatcatggga ggaattagtt ttgaccgtca ggtcttcaag    480
```

```
agttttgaac tcttcttctt gaactgtgta acctttaaaa tgacgggatc taaatacgtc    540
atggatgaga tcatgtgtgt aaaaactgac tccagcatat ggaatcattc caaagattgt    600
aggagcgaac ccacgataaa agtttcccaa ccttgccaaa gtgtctaatg ctgtgacttg    660
aaatctgggt tcctcgttga agaccctgcg tactatgccc aaaaactttc ctccacgagc    720
cctattaact tctctatgag tttcaaatgc caaacggaca cggattaggt ccaatgggta    780
agtgaaaaac acagagcaaa ccccagctaa tgagccggcc agtaaccgtc ttggagctgt    840
ttcataagag tcattaggga tcaataacgt tctaatctgt tcataacata caaattttat    900
ggctgcatag ggaaaaattc tcaacagggt agccgaatga ccctgatata gacctgcgac    960
accatcatac ccatagatct gcctgacagc cttaaagagc ccgctaaaag acccggaaaa   1020
ccgagagaac tctggattag cagtctgaaa aagaatcttc actctgtcta gtggagcaat   1080
taatgtctta gcggcacttc ctgctactcc gccagctact cctgaataga tcacatactg   1140
caaagactgc ttgtcgatga ccttggggtt atttagcttc aagggcaatt tttgggacat   1200
tttggacaca ggagactcag aaacagacac agagcgttct gagtcctggt gctcctgacg   1260
taggcctaga acaggaatta ttggctttat ttgtttgtcc atttcatagg cttggggtaa   1320
tagatagatg acagagaaat agagaagacc taatattttt tgttcatggc aaatcgcggg   1380
ttcgcggtcg ggtcacacac ggagaagtaa tgagaagagc tggtaatctg gggtaaaagg   1440
gttcaaaaga aggtcgcctg gtagggatgc aatacaaggt tgtcttggag tttacattga   1500
ccagatgatt tggctttttc tctgttcaat tcacattttt cagcgagaat cggattgacg   1560
gagaaatggc ggggtgtggg gtggatagat ggcagaaatg ctcgcaatca ccgcgaaaga   1620
aagactttat ggaatagaac tactgggtgg tgtaaggatt acatagctag tccaatggag   1680
tccgttggaa aggtaagaag aagctaaaac cggctaagta actagggaag aatgatcaga   1740
ctttgatttg atgaggtctg aaaatactct gctgcttttt cagttgcttt ttccctgcaa   1800
cctatcattt tccttttcat aagcctgcct tttctgtttt cacttatatg agttccgccg   1860
agacttcccc aaattctctc ctggaacatt ctctatcgct ctccttccaa gttgcgcccc   1920
ctggcactgc ctagtaatat taccacgcga cttatattca gttccacaat ttccagtgtt   1980
cgtagcaaat atcatcagcc taccgttcgt atagcataca ttatacgaag ttatggatct   2040
aacatccaaa gacgaaaggt tgaatgaaac ctttttgcca tccgacatcc acaggtccat   2100
tctcacacat aagtgccaaa cgcaacagga ggggatacac tagcagcaga ccgttgcaaa   2160
cgcaggacct ccactcctct tctcctcaac acccacttt t gccatcgaaa accagcccat   2220
gttattgggc ttgattggag ctcgctcatt ccaattcctt ctattaggct actaacacca   2280
tgactttatt agcctgtcta tcctggcccc cctggcgagg ttcatgtttg tttatttccg   2340
aatgcaacaa gctccgcatt acacccgaac atcactccag atgagggctt tctgagtgtg   2400
gggtcaaata gtttcatgtt ccccaaatgg cccaaaactg acagtttaaa cgctgtcttg   2460
gaacctaata tgacaaaagc gtgatctcat ccaagatgaa ctaagtttgg ttcgttgaaa   2520
tgctaacggc cagttggtca aaagaaact tccaaaagtc ggcataccgt tgtcttgtt    2580 tggtattgat tgacgaatgc tcaaaaataa tctcattaat gcttagcgca gtctctctat   2640
cgcttctgaa ccccggtgca cctgtgccga aacgcaaatg gggaaacacc cgctttttgg   2700
atgattatgc attgtctcca cattgtatgc ttccaagatt ctggtgggaa tactgctgat   2760
agcctaacgt tcatgatcaa aatttaactg ttctaacccc tacttgacag caatatataa   2820
acagaaggaa gctgccctgt cttaaacctt tttttttatc atcattatta gcttactttc   2880
```

```
ataattgcga ctggttccaa ttgacaagct tttgatttta acgacttttt acgacaactt    2940
gagaagatca aaaacaact aattattcga acgatggta agccgatacg tacccgatat      3000
gggcgatctg atttggggtg attttgaccc gacaaaaggt agcgagcaag ctggacatcg    3060
tccagctgtt gtcctgagtc ctttcatgta caacaacaaa acaggtatgt gtctgtgtgt    3120
tccttgtaca acgcaatcaa aaggatatcc gttcgaagtt gttttatccg gtcaggaacg    3180
tgatggcgta gcgttagctg atcaggtaaa aagtatcgcc tggcgggcaa gaggagcaac    3240
gaagaaagga acagttgccc cagaggaatt acaactcatt aaagccaaaa ttaacgtact    3300
gattgggtaa tcaagaggat gtcagaatgc catttgcctg agatgcag gcttcattt      3360 tgatactttt ttatttgtaa cctatatagt ataggatttt ttttgtcatt ttgtttcttc    3420
tcgtacgagc ttgctcctga tcagcctatc tcgcagctga tgaatatctt gtggtagggg    3480
tttgggaaaa tcattcgagt ttgatgtttt tcttggtatt tcccactcct cttcagagta    3540
cagaagatta agtgacacgt tcgtttgtgc aagcttcaac gatgccaaaa gggtataata    3600
agcgtcattt gcagcattgt gaagaaaact atgtggcaag ccaagcctgc gaagaatgta    3660
gtcgagaatt gagcttgcct cgtccccgcc gggtcacccg ccagcgaca tggaggccca    3720 gaatacccctc cttgacagtc ttgacgtgcg cagctcaggg gcatgatgtg actgtcgccc    3780
gtacatttag cccatacatc cccatgtata atcatttgca tccatacatt ttgatggccg    3840
cacggcgcga agcaaaaatt acggctcctc gctgcagacc tgcgagcagg gaaacgctcc    3900
cctcacagac gcgttgaatt gtccccacgc gcgcccctg tagagaaata taaaaggtta    3960
ggatttgcca ctgaggttct tctttcatat acttcctttt aaaatcttgc taggatacag    4020
ttctcacatc acatccgaac ataaacaaaa atgaccactt tggatgatac tgcttacaga    4080
tacagaactt ctgttccagg tgatgctgaa gctattgaag ctttggatgg atctttcacc    4140
actgatactg ttttcagagt cactgctact ggtgatggat tcactttgag agaagttcct    4200
gttgatcctc ctttgaccaa agttttttcct gatgatgaat ctgatgatga atctgatgct    4260
ggtgaagatg gtgatccaga ttctagaact tttgttgctt atggtgatga tggtgatttg    4320
gctggatttg ttgttgtttc ttattctgga tggaacagaa gattgactgt tgaagatatt    4380
gaagttgctc cagaacatag aggtcatggt gttggaagag ctttgatggg attggcaact    4440
gagtttgcca gagaaagagg tgctggtcat ctttggttgg aagtcaccaa tgtcaatgct    4500
ccagctattc atgcttacag aagaatggga ttcactcttt gtggattgga tactgctttg    4560
tatgatggaa ctgcttctga tggagaacaa gctttgtaca tgtccatgcc atgtccttaa    4620
agtaactgac aataaaaaga ttcttgtttt caagaacttg tcatttgtat agttttttta    4680
tattgtagtt gttctatttt aatcaaatgt tagcgtgatt tatatttttt ttcgcctcga    4740
catcatctgc ccagatgcga agttaagtgc gcagaaagta atatcatgcg tcaatcgtat    4800
gtgaatgctg gtcgctatac tgctgtcgat tcgatactaa cgccgccatc cagtgtcata    4860
acttcgtata gcatacatta tacgaacggt acttttttgt agaaatgtct tggtgtcctc    4920
gtccaatcag gtagccatct ctgaaatatc tggctccgtt gcaactccga acgacctgct    4980
ggcaacgtaa aattctccgg ggtaaaactt aaatgtggag taatggaacc agaaacgtct    5040
cttcccttct ctctccttcc accgcccgtt accgtcccta ggaaatttta ctctgctgga    5100
gagcttcttc tacggccccc ttgcagcaat gctcttccca gcattacgtt gcgggtaaaa    5160
cggaggtcgt gtacccgacc tagcagccca gggatggaaa agtcccggcc gtcgctggca    5220
```

```
ataatagcgg gcggacgcat gtcatgagat tattggaaac caccagaatc gaatataaaa    5280
ggcgaacacc tttcccaatt ttggtttctc ctgacccaaa gactttaaat ttaatttatt    5340
tgtccctatt tcaatcaatt gaacaactat ttcgcgaaac gatgagattt ccttcaattt    5400
ttactgctgt tttattcgca gcatcctccg cattagctgc tccagtcaac actacaacag    5460
aagatgaaac ggcacaaatt ccggctgaag ctgtcatcgg ttactcagat ttagaagggg    5520
atttcgatgt tgctgttttg ccattttcca acagcacaaa taacgggtta ttgtttataa    5580
atactactat tgccagcatt gctgctaaag aagaaggggt atctctcgag aaaagagagg    5640
ctgaagctga attcgccaca aaacgtggat ctcccaaccc tacgagggcg gcagcagtca    5700
aggccgcatt ccagacgtcg tggaacgctt accaccattt tgccttttcc catgacgacc    5760 tccaccggt cagcaacagc tttgatgatg agagaaacgg ctggggctcg tcggcaatcg    5820
atggcttgga cacggctatc ctcatggggg atgccgacat tgtgaacacg atccttcagt    5880
atgtaccgca gatcaacttc accacgactg cggttgccaa ccaaggatcc tccgtgttcg    5940
agaccaacat tcggtacctc ggtggcctgc tttctgccta tgacctgttg cgaggtcctt    6000
tcagctcctt ggcgacaaac cagaccctgg taaacagcct tctgaggcag gctcaaacac    6060
tggccaacgg cctcaaggtt gcgttcacca ctcccagcgg tgtcccggac cctaccgtct    6120
tcttcaaccc tactgtccgg agaagtggtg catctagcaa caacgtcgct gaaattggaa    6180
gcctggtgct cgagtggaca cggttgagcg acctgacggg aaaaccgcag tatgcccagc    6240
ttgcgcagaa gggcgagtcg tatctcctga atccaaaggg aagcccggag gcatggcctg    6300
gcctgattgg aacgtttgtc agcacgagca acggtacctt tcaggatagc agcggcagct    6360
ggtccggcct catggacagc ttctacgagt acctgatcaa gatgtacctg tacgacccgg    6420
ttgcgtttgc acactacaag gatcgctggg tccttggtgc cgactcgacc attgggcatc    6480
tcggctctca cccgtcgacg cgcaaggact tgacctttt gtcttcgtac aacggacagt    6540
ctacgtcgcc aaactcagga catttggcca gttttggcgg tggcaacttc atcttgggag    6600
gcattctcct gaacgagcaa aagtacattg actttggaat caagcttgcc agctcgtact    6660
ttggcacgta cacccagacg gcttctggaa tcggccccga aggcttcgcg tgggtggaca    6720
gcgtgacggg cgccggcggc tcgccgccct cgtcccagtc cgggttctac tcgtcggcag    6780
gattctgggt gacggcaccg tattacatcc tgcggccgga gacgctggag agcttgtact    6840
acgcataccg cgtcacgggc gactccaagt ggcaggacct ggcgtgggaa gcgttgagtg    6900
ccattgagga cgcatgccgc gccggcagcg cgtactcgtc catcaacgac gtgacgcagg    6960
ccaacggcgg gggtgcctct gacgatatgg agagcttctg gtttgccgag gcgctcaagt    7020
atgcgtacct gatcttttgcg gaggagtcgg atgtgcaggt gcaggccacc ggcgggaaca    7080
aatttgtctt taacacggag gcgcacccct ttagcatccg ttcatcatca cgacggggcg    7140
gccaccttgc tcacgacgag ttgtaatcta gggcggccgc cagcttgggc ccgaacaaaa    7200
actcatctca gaagaggatc tgaatagcgc cgtcgaccat catcatcatc atcattgagt    7260
tttagcctta gacatgactg ttcctcagtt caagttgggc acttacgaga agaccggtct    7320
tgctagattc taatcaagag gatgtcagaa tgccatttgc ctgagagatg caggcttcat    7380
ttttgatact ttttttatttg taacctatat agtataggat ttttttttgtc attttgttc    7440 ttctcgtacg agcttgctcc tgatcagcct atctcgcagc tgatgaatat cttgtggtag    7500
gggtttggga aaatcattcg agtttgatgt ttttcttggt atttcccact cctcttcaga    7560
gtacagaaga ttaagtgaga ccttcgtttg tgcggatccc ccacacacca tagcttcaaa    7620
```

```
atgtttctac tcctttttta ctcttccaga ttttctcgga ctccgcgcat cgccgtacca    7680
cttcaaaaca cccaagcaca gcatactaaa tttccctct ttcttcctct agggtgtcgt    7740
taattacccg tactaaaggt ttggaaaaga aaaagagac cgcctcgttt cttttcttc    7800 gtcgaaaaag gcaataaaaa ttttatcac gtttctttt cttgaaaatt ttttttttg    7860 atttttttct ctttcgatga cctcccattg atatttaagt taataaacgg tcttcaattt    7920
ctcaagtttc agtttcattt tcttgttct attacaactt ttttacttc ttgctcatta    7980 gaaagaaagc atagcaatct aatctaaggg cggtgttgac aattaatcat cggcatagta    8040
tatcggcata gtataatacg acaaggtgag gaactaaacc atggccaagc ctttgtctca    8100
agaagaatcc accctcattg aaagagcaac ggctacaatc aacagcatcc ccatctctga    8160
agactacagc gtcgccagcg cagctctctc tagcgacggc cgcatcttca ctggtgtcaa    8220
tgtatatcat tttactgggg gaccttgtgc agaactcgtg gtgctgggca ctgctgctgc    8280
tgcggcagct ggcaacctga cttgtatcgt cgcgatcgga aatgagaaca ggggcatctt    8340
gagcccctgc ggacggtgcc gacaggtgct tctcgatctg catcctggga tcaaagccat    8400
agtgaaggac agtgatggac agccgacggc agttgggatt cgtgaattgc tgccctctgg    8460
ttatgtgtgg gagggctaag cacttcgtgg ccgaggagca ggactgacac gtccgacgcg    8520
gcccgacggg tccgaggcct cggagatccg tccccctttt cctttgtcga tatcatgtaa    8580
ttagttatgt cacgcttaca ttcacgccct cccccacat ccgctctaac cgaaaaggaa    8640
ggagttagac aacctgaagt ctaggtccct atttatttt ttatagttat gttagtatta    8700
agaacgttat ttatatttca aatttttctt ttttttctgt acagacgcgt gtacgcatgt    8760
aacattatac tgaaaacctt gcttgagaag gttttgggac gctcgaaggc tttaatttgc    8820
aagctggaga ccaacatgtg agcaaaaggc cagcaaaagg ccaggaaccg taaaaaggcc    8880
gcgttgctgg cgttttcca taggctccgc cccctgacg agcatcacaa aaatcgacgc    8940
tcaagtcaga ggtggcgaaa cccgacagga ctataaagat accaggcgtt ccccctgga    9000 agctccctcg tgcgctctcc tgttccgacc ctgccgctta ccggatacct gtccgccttt    9060
ctcccttcgg gaagcgtggc gctttctcaa tgctcacgct gtaggtatct cagttcggtg    9120
taggtcgttc gctccaagct gggctgtgtg cacgaacccc ccgttcagcc cgaccgctgc    9180
gccttatccg gtaactatcg tcttgagtcc aacccggtaa gacacgactt atcgccactg    9240
gcagcagcca ctggtaacag gattagcaga gcgaggtatg taggcggtgc tacagagttc    9300
ttgaagtggt ggcctaacta cggctacact agaaggacag tatttggtat ctgcgctctg    9360
ctgaagccag ttaccttcgg aaaaagagtt ggtagctctt gatccggcaa acaaaccacc    9420
gctggtagcg gtggtttttt tgtttgcaag cagcagatta cgcgcagaaa aaaggatct    9480 caagaagatc ctttgatctt ttctacgggg tctgacgctc agtggaacga aaactcacgt    9540
taagggattt tggtcatgag atcagatcta acatccataa tcgtattcgc cgtttctgtc    9600
atttgcgttt tgtacggacc ctcacaacaa ttatcatctc caaaaataga ctatgatcca    9660
ttgacgctcc gatcacttga tttgaagact ttggaagctc cttcacagtt gagtccaggc    9720
accgtagaag ataatcttcg aagacaattg gagtttcatt ttccttaccg cagttacgaa    9780
ccttttcccc aacatatttg gcaaacgtgg aaagtttctc cctctgatag ttcctttccg    9840
aaaaacttca aagacttagg tgaaagttgg ctgcaaaggt ccccaaatta tgatcatttt    9900 gtgataccg atgatgcagc atgggaactt attcaccatg aatacgaacg tgtaccagaa    9960
```

-continued

| | | | | | |
|---|---|---|---|---|---|
| gtcttggaag | ctttccacct | gctaccagag | cccattctaa | aggccgattt | tttcaggtat | 10020 |
| ttgattcttt | ttgcccgtgg | aggactgtat | gctgacatgg | acactatgtt | attaaaacca | 10080 |
| atagaatcgt | ggctgacttt | caatgaaact | attggtggag | taaaaaacaa | tgctgggttg | 10140 |
| gtcattggta | ttgaggctga | tcctgataga | cctgattggc | acgactggta | tgctagaagg | 10200 |
| atacaatttt | gccaatgggc | aattcagtcc | aaacgaggac | acccagcact | gcgtgaactg | 10260 |
| attgtaagag | ttgtcagcac | gactttacgg | aaagagaaaa | gcggttactt | gaacatggtg | 10320 |
| gaaggaaagg | atcgtggaag | tgatgtgatg | gactggacgg | gtccaggaat | atttacagac | 10380 |
| actctatttg | attatatgac | taatgtcaat | acaacaggcc | actcaggcca | aggaattgga | 10440 |
| gctggctcag | cgtattacaa | tgccttatcg | ttggaagaac | gtgatgccct | ctctgcccgc | 10500 |
| ccgaacggag | agatgttaaa | agagaaagtc | ccaggtaaat | atgcacagca | ggttgtttta | 10560 |
| tgggaacaat | ttaccaacct | gcgctccccc | aaattaatcg | acgatattct | tattcttccg | 10620 |
| atcaccagct | tcagtccagg | gattggccac | agtggagctg | gagatttgaa | ccatcacctt | 10680 |
| gcatatatta | ggcatacatt | tgaaggaagt | tggaaggact | aaagaaagct | agagtaaaat | 10740 |
| agatatagcg | agattagaga | atgaatacct | tcttctaagc | gatcgtccgt | catcatagaa | 10800 |
| tatcatggac | tgtatagttt | tttttttgta | catataatga | ttaaacgtc | atccaacatc | 10860 |
| tcgttgacag | atctctcagt | acgcgaaatc | cctgactatc | aaagcaagaa | ccgatgaaga | 10920 |
| aaaaaacaac | agtaacccaa | acaccacaac | aaacacttta | tcttctcccc | cccaacacca | 10980 |
| atcatcaaag | agatgtcgga | accaaacacc | aagaagcaaa | aactaaccccc | atataaaaac | 11040 |
| atcctggtag | ataatgctgg | taacccgctc | tccttccata | ttctgggcta | cttcacgaag | 11100 |
| tctgaccggt | ctcagttgat | caacatgatc | ctcgaaatgg | gtggcaagat | cgttccagac | 11160 |
| ctgcctcctc | tggtagatgg | agtgttgttt | ttgacagggg | attacaagtc | tattgatgaa | 11220 |
| gataccctaa | agcaactggg | ggacgttcca | atatacagag | actccttcat | ctaccagtgt | 11280 |
| tttgtgcaca | agacatctct | tcccattgac | actttccgaa | ttgacaagaa | cgtcgacttg | 11340 |
| gctcaagatt | tgatcaatag | ggcccttcaa | gagtctgtgg | atcatgtcac | ttctgccagc | 11400 |
| acagctgcag | ctgctgctgt | tgttgtcgct | accaacggcc | tgtcttctaa | accagacgct | 11460 |
| cgtactagca | aaatacagtt | cactcccgaa | gaagatcgtt | ttattcttga | ctttgttagg | 11520 |
| agaaatccta | acgaagaaa | cacacatcaa | ctgtacactg | agctcgctca | gcacatgaaa | 11580 |
| aaccatacga | atcattctat | ccgccacaga | tttcgtcgta | atctttccgc | tcaacttgat | 11640 |
| tgggtttatg | atatcgatcc | attgaccaac | caacctcgaa | aagatgaaaa | cgggaactac | 11700 |
| atcaaggtac | aagatcttcc | acaaggaatt | cgtggtcatt | attctgccca | agatgattac | 11760 |
| aatttgtgtt | tatcggttca | acctttcatt | gaatctgtag | atgagacaac | aggccaagaa | 11820 |
| tttttcaaac | ctctgaaagg | tgtatttgat | gacttggaat | ctcgctttcc | tcaccataca | 11880 |
| aagacttcct | ggagagacag | attcagaaag | tttgcctcta | aatacggtgt | tcgtcagtac | 11940 |
| atcgcgtatt | atgaaaagac | tgttgaactc | aatggtgttc | ctaatccgat | gacgaacttt | 12000 |
| acctcaaagg | cttccattga | aaaatttaga | gaaagacgcg | ggacttcacg | taacagtggc | 12060 |
| cttccaggcc | cggttggtgt | agaagctgta | agctctttgg | accacatatc | cccattggtc | 12120 |
| acatctaatt | ccaattctgc | agctgctgca | gctgctgccg | cagcagttgc | agcctctgcc | 12180 |
| tctgcttctt | cagctcctaa | tacttcaact | accaatttct | ttgaacagga | gaatattgcc | 12240 |
| caagttctct | ctgcacataa | caacgagcag | tctattgcag | aagttattga | gtccgcacag | 12300 |
| aatgtcaaca | cccatgaaag | tgaacctata | gctgatcatg | ttcgaaaaaa | tcttacagac | 12360 |

-continued

```
gatgaattgc ttgacaaaat ggatgatatt ttaagctcca gaagtctagg cggactagat    12420
gacttgataa agatcctcta cactgagctg ggatttgctc atcgttatac cgaatttctt    12480
tttacctcat gttctggtga tgtgattttc ttccgaccat tagtggaaca tttccttctt    12540
actggtgagt gggagctgga gaatactcgt ggcatctgga ccggtcgtca agacgaaatg    12600
ctacgtgcta gcaatctaga tgacctgcac aagttaattg acctgcatgg gaaagaacgt    12660
gttgagacca gaagaaaagc catcaaggga gaatgatcat aagaaatgaa aaacgtataa    12720
gt                                                                  12722
```

<210> SEQ ID NO 60
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 60
caagttgcgc cccctggca                                                19

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 61
tggagcagct aatgcggagg a                                             21

<210> SEQ ID NO 62
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 62
agttccgccg agacttcccc a                                             21

<210> SEQ ID NO 63
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 63
ttcagccgga atttgtgccg t                                             21

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
atccagggtg acggtgccga                                               20

<210> SEQ ID NO 65
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 65
gcaagaggcc cggcagtacc                                                    20

<210> SEQ ID NO 66
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 66
ccgccctcgt agggttggga g                                                  21

<210> SEQ ID NO 67
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 67
ttcgcggtcg ggtcacaca                                                     19

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
aactgccatc tgccttcgcc                                                    20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
caaatcgcgg gttcgcggtc                                                    20

<210> SEQ ID NO 70
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 70
gagcaaactg ccatctgcct tcg                                                23

<210> SEQ ID NO 71
<211> LENGTH: 75
<212> TYPE: DNA
<213> ORGANISM: Artificial Sequence
<220> FEATURE:
<223> OTHER INFORMATION: Synthetic Oligonucelotide

<400> SEQUENCE: 71
gtgttcgtag caaatatcat cagcctaccg ttcgtatagc atacattata cgaagttatg        60
```
gatctaacat ccaaa                                                          75

<210> SEQ ID NO 72
<211> LENGTH: 75
<212> TYPE: DNA
<213> ORGANISM: Artificial Sequence
<220> FEATURE:
<223> OTHER INFORMATION: Synthetic Oligonucelotide

<400> SEQUENCE: 72
tttggatgtt agatccataa cttcgtataa tgtatgctat acgaacggta ggctgatgat        60
atttgctacg aacac                                                          75

<210> SEQ ID NO 73
<211> LENGTH: 75
<212> TYPE: DNA
<213> ORGANISM: Artificial Sequence
<220> FEATURE:
<223> OTHER INFORMATION: Synthetic Oligonucelotide

<400> SEQUENCE: 73
gccgccatcc agtgtcataa cttcgtatag catacattat acgaacggta cttttttgta        60
gaaatgtctt ggtgt                                                          75

<210> SEQ ID NO 74
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 74
acaccaagac atttctacaa aaaagtaccg ttcgtataat gtatgctata cgaagttatg        60
acactggatg gcggc                                                          75

<210> SEQ ID NO 75
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 75
gtgttcgtag caaatatcat cagcctaccg                                          30

<210> SEQ ID NO 76
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 76
acaccaagac atttctacaa aaaagtaccg t                                        31

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
ttcgcggtcg ggtcacacac                                              20

<210> SEQ ID NO 78
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 78
ggagcagcta atgcggagga tgc                                          23

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
cggtcgggtc acacacggag                                              20

<210> SEQ ID NO 80
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 80
tggagcagct aatgcggagg a                                            21

<210> SEQ ID NO 81
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 81
tgagtcctgg tgctcctgac g                                            21

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
cccctcctgt tgcgtttggc                                              20

<210> SEQ ID NO 83
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 83
agcgttctga gtcctggtgc t                                            21

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
ggtcctgcgt ttgcaacggt                                                20

<210> SEQ ID NO 85
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 85
actaacgccg ccatccagtg tc                                             22

<210> SEQ ID NO 86
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 86
gcttcagccg gaatttgtgc cg                                             22

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
cgcctcgaca tcatctgccc                                                20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
tcagccggaa tttgtgccgt                                                20

<210> SEQ ID NO 89
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 89

Phe Tyr Met Ala Ile Phe Ala Val Ser Val Ile Cys Val Leu Tyr Gly
1               5                   10                  15

Pro Ser Gln Gln Leu Ser Ser
            20

<210> SEQ ID NO 90
<211> LENGTH: 5
<212> TYPE: PRT
<213> ORGANISM: Artificial Sequence
<220> FEATURE:
<223> OTHER INFORMATION: Synthetic Peptide

```
<400> SEQUENCE: 90

Phe Tyr Met Ala Ile
1               5

<210> SEQ ID NO 91
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 91

His Asp Glu Leu
1

<210> SEQ ID NO 92
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 92

Leu Phe Ala Arg Gly Gly Leu Tyr Ala Asp Met Asp Thr Met
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 93

Gly Lys Pro Ile Pro Asn Pro Leu Leu Gly Leu Asp Ser Thr
1               5                   10
```

PICHIA PASTORIS STRAINS FOR PRODUCING PREDOMINANTLY HOMOGENEOUS GLYCAN STRUCTURE

CROSS REFERENCE TO RELATED APPLICATION

This application is a continuation of U.S. patent application Ser. No. 16/404,838, filed May 7, 2019, which is a continuation of U.S. patent application Ser. No. 15/444,870, filed Feb. 28, 2017, now U.S. Pat. No. 10,329,572, which is a continuation of U.S. patent application Ser. No. 14/437,683, filed Apr. 22, 2015, now U.S. Pat. No. 9,617,550, which is a 371 of international application having Serial No. PCT/US2013/066335, filed on Oct. 23, 2013, which claims the benefit of priority from U.S. Provisional Application No. 61/717,423, filed Oct. 23, 2012, the entire contents of which are incorporated herein by reference.

INCORPORATION BY REFERENCE OF SEQUENCE LISTING

The Sequence Listing in an ASCII text file, named 30272_Sequence_Listing.txt of 81 KB, created on Apr. 21, 2015, and submitted to the United States Patent and Trademark Office via EFS-Web, is incorporated herein by reference.

BACKGROUND OF THE INVENTION

*Pichia pastoris* is a highly successful system for production of a wide variety of recombinant proteins. Several factors have contributed to its rapid acceptance, including: (1) a promoter derived from the alcohol oxidase I (AOX1) gene of *P. pastoris* that is uniquely suited for the controlled expression of foreign genes; (2) the similarity of techniques needed for the molecular genetic manipulation of *P. pastoris* to those of *Saccharomyces cerevisiae*; and (3) the strong preference of *P. pastoris* for respiratory growth, a physiological trait that facilitates its culturing at high-cell densities relative to fermentative yeasts.

As a yeast, *P. pastoris* is a single-celled microorganism that is easy to manipulate and culture. However, it is also a eukaryote and capable of many of the post-translational modifications performed by higher eukaryotic cells such as proteolytic processing, folding, disulfide bond formation and glycosylation. Thus, many proteins that would end up as inactive inclusion bodies in bacterial systems are produced as biologically active molecules in *P. pastoris*. The *P. pastoris* system is also generally regarded as being faster, easier, and less expensive to use than expression systems derived from higher eukaryotes such as insect and mammalian tissue culture cell systems and usually gives higher expression levels.

*P. pastoris* has the potential of performing many of the posttranslational modifications typically associated with higher eukaryotes. These include processing of signal sequences (both pre- and prepro-type), folding, disulfide bridge formation, and both O- and N-linked glycosylation. Glycosylation of secreted foreign (higher) eukaryotic proteins by *P. pastoris* and other fungi can be problematic. In mammals, O-linked oligosaccharides are composed of a variety of sugars including N-acetylgalactosamine, galactose and sialic acid. In contrast, lower eukaryotes, including *P. pastoris*, may add O-oligosaccharides solely composed of mannose (Man) residues.

N-glycosylation in *P. pastoris* is also different than in higher eukaryotes. In all eukaryotes, it begins in the ER with the transfer of a lipid-linked oligosaccharide unit, Glc3Man9GlcNAc2 ((Glc=glucose; GlcNAc=N-acetylglucosamine), to asparagine at the recognition sequence Asn-X-Ser/Thr. This oligosaccharide core unit is subsequently trimmed to Man8GlcNAc2. It is at this point that lower and higher eukaryotic glycosylation patterns begin to differ. The mammalian Golgi apparatus performs a series of trimming and addition reactions that generate oligosaccharides composed of either Man5-6GlcNAc2 (high-mannose type), a mixture of several different sugars (complex type) or a combination of both (hybrid type). Two distinct patterns of N-glycosylation have been observed on foreign proteins secreted by *P. pastoris*. Some proteins are secreted with carbohydrate structures similar in size and structure to the core unit (Man8-11GlcNAc2). Other foreign proteins secreted from *P. pastoris* receive much more carbohydrate and appear to be hyperglycosylated.

N-linked high mannose oligosaccharides added to proteins by yeasts represent a problem in the use of foreign secreted proteins by the pharmaceutical industry. For example, they can be exceedingly antigenic when introduced intravenously into mammals and furthermore may cause rapid clearance of the protein from the blood by the liver.

In an attempt to modify the N-glycosylation pathway of *Pichia pastoris*, a strain (hereinafter referred to as "M5-Blast") was created, as described in Jacobs et al., 2009, *Nature Protocols* 4:58-70. M5-Blast is a modification of the *P. pastoris* GS115 strain wherein the endogenous mannosyltransferase gene OCH1 is disrupted by the introduction of a cassette comprising an $\alpha$-1,2 mannosidase gene. However, the M5-Blast strain is subject to genomic rearrangements that regenerate the endogenous OCH1 gene and in parallel remove the $\alpha$-1,2 mannosidase gene after rounds of freezing and thawing, growth under various temperatures and conditions, and from subsequent transformations with other plasmids to introduce exogenous genes.

SUMMARY OF THE DISCLOSURE

Disclosed herein are novel *Pichia pastoris* strains for expression of exogenous proteins with substantially homogeneous N-glycans. More specifically, the strains are genetically engineered to include a mutant OCH1 allele which is transcribed into an mRNA coding for a mutant OCH1 gene product (i.e., $\alpha$-1,6-mannosyltransferase, or "OCH1 protein"). The mutant OCH1 protein contains a catalytic domain substantially identical to that of the wild type OCH1 protein, but has an N-terminal sequence that alters the localization of the OCH1 protein to or in the Golgi apparatus. The strains do not include any other OCH1 allele that produces an mRNA coding for a functional OCH1 protein. Such strains are robust, stable, and transformable, and the mutant OCH1 allele and the associated phenotype (i.e., ability to produce substantially homogeneous N-glycans) are maintained for generations, after rounds of freezing and thawing, and after subsequent transformations.

This disclosure also features methods of constructing the strains, as well as methods of expressing proteins via the strains.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 4. Addition of M5-Blast genomic DNA extensions onto existing lox71-MazF-Nat$^R$-lox66 cassette.

FIG. 5. Overlap assembly and amplification of the final sequence for generating the double crossover fragment for M5-Blast *Pichia* transformation. This final construct has >500 bp of homology arms flanking the selection/counter-selection cassette.

Figure 1:
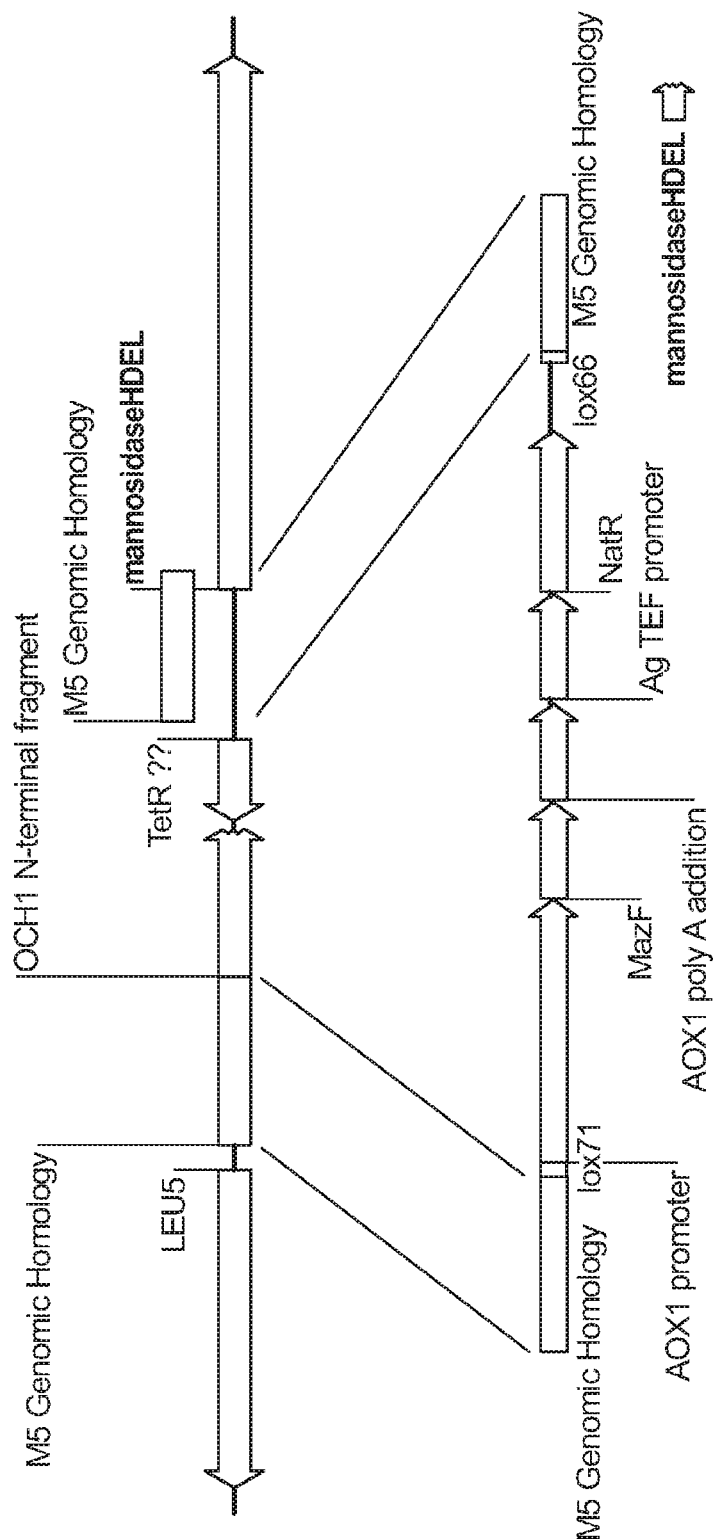
FIG. 1. Diagram of deletion strategy for removing the OCH1 N-terminal fragment homology from M5-Blast *Pichia* genome. Homology arms flanking the OCH1 N-terminal fragment are used to create a double crossover construct containing lox71-lox66 recombination sites. The intervening sequences can be removed by cre mediated recombination.

Tables 1-6 are set forth on pages 36-49. Tables 7-8 are found on page 32 (Example 7).

Table 1 lists the DNA sequence (SEQ ID NO: 1) of the OCH1 locus in a SuperM5 strain described in Example 1.

Table 2 lists the amino acid sequence for wild type OCH1 (SEQ II) NO: 2) in *Pichia pastoris*.

Table 3 lists nucleotides that may be deleted from the Upstream OCH1 segment.

Table 4 lists the DNA sequence for the OCH1 locus (+/−2 kb) for the M5-Blast *Pichia pastoris* strain.

Table 5 lists the amino acid sequence and nucleotide sequence for the Upstream OCH1 segment.

Table 6 lists the amino acid sequence and nucleotide sequence for the Downstream OCH1 segment.

Table 7. N-glycan analysis of trastuzumab obtained from Study 2 (Example 6).

Table 8. Kinetic parameters of trastuzumab analyzed on BIAcore (Example 6).

DETAILED DESCRIPTION

Genetically Engineered *Pichia pastoris* Strains

This disclosure features novel genetically engineered *Pichia pastoris* strains which are robust, stable, and transformable, and which produce proteins with substantially homogeneous N-glycan structures.

As further described herein, the strains are genetically engineered to include a mutant OCH1 allele which is transcribed into an mRNA coding for a mutant OCH1 gene product (i.e., α-1,6-mannosyltransferase, or "OCH1 protein"). The mutant OCH1 protein contains a catalytic domain substantially identical to that of the wild type OCH1 protein, but has an N-terminal sequence that alters the localization of the OCH1 protein to or in the Golgi apparatus. The strains do not include any other OCH1 allele that produces an mRNA coding for a functional OCH1 protein.

The strains can be additionally genetically engineered to contain a nucleic acid coding for and expressing an α-1,2-mannosidase which converts the M8 N-glycan, Man8GlcNAc2, to the M5 N-glycan, Man5GlcNAc2.

As a result of the genetic modifications, the strains disclosed herein produce substantially homogeneous N-glycans.

By "substantially homogeneous" N-glycans it is meant that given a preparation containing a population of a particular glycoprotein of interest, at least 50%, 60%, 75%, 80%, 85%, 90% or even 95% of the N-glycans on the protein molecules within the population are the same.

By "predominant N-glycan structure" or "predominant glycoform" it is meant a specific N-glycan structure or glycoform of (i.e., attached to) a protein constitutes the greatest percentage of all N-glycan structures or glycoforms of the protein. In certain specific embodiments, a predominant glycoform accounts for at least 40%, 50%, 60%, 70%, 80%, 90% or 95% or greater of the population of all glycoforms on the protein. Examples of desirable N-glycan structures include, e.g., Man8GlcNAc2 (or "M8") or Man5GlcNAc2("M5"). Additional desirable N-glycan structures include, GnM5 (GlcNAcMan$_5$GlcNAc$_2$), GalGnM5 (GalGlcNAcMan$_5$GlcNAc$_2$), GalGnM3 (GalGlcNAcMan$_3$GlcNAc$_2$), GnM3 (GlcNAcMan$_3$GlcNAc$_2$), Gn2M3 (GlcNAc$_2$Man$_3$GlcNAc$_2$), and Gal2Gn2M3 (Gal$_2$GlcNAc$_2$Man$_3$GlcNAc$_2$). The structures of these N-glycans have been described, e.g., in Jacobs et al., 2009, *Nature Protocols* 4:58-70, incorporated herein by reference.

In a specific embodiment, the strains of this invention include both a mutant OCH1 allele and a nucleic acid coding for and expressing an α-1,2-mannosidase, such that the strains produce homogeneous N-glycans with M5 being the predominant glycoform. These strains are also referred to herein as SuperM5 or SuperMan5 strains. An example of a SuperM5 strain is described in the Example section below.

The strains of this invention are "robust", which means that the strains (unless noted otherwise as an auxotroph or deficient strain, e.g., protease deficient, AOX1 mutant, etc.) have approximately the same growth rate and the same growth conditions as unmodified *Pichia pastoris* strains such as strain GS11.5. For example, the strains of this invention can grow at elevated temperatures (e.g., 30° C., 37° C. or even 42° C.) and are not temperature sensitive. For example, the SuperM5 strains disclosed herein are robust and are not temperature sensitive.

The strains of this invention are also stable, which means that the genetic modifications and the phenotype as a result of the genetic modifications (i.e., producing homogeneous N-glycans) are maintained through generations, e.g., at least 10, 20, 30, 40 or 50 generations (cell divisions), after rounds of freezing and thawing, and after subsequent transformations. For example, the SuperM5 strains disclosed herein maintain the mutant OCH1 allele through generations and are able to continue making substantially homogeneous M8 (or other downstream N-glycans), without reversion.

Genetic Engineering—Mutant OCH1 Allele

The strains of this invention are genetically engineered to include a mutant OCH1 allele which is transcribed into an mRNA coding for a mutant OCH1 gene product (i.e., α-1,6-mannosyltransferase, or the "OCH1 protein"). The mutant OCH1 protein contains a catalytic domain substantially identical to that of the wild type OCH1 protein but has an N-terminal sequence that alters the localization of the OCH1 protein to or in the Golgi apparatus.

The wild type OCH1 gene of *Pichia pastoris* has an open reading frame that encodes a protein of 404 amino acids (SEQ ID NO: 2). Like other fungal Golgi glycosyltransferases, the *Pichia pastoris* OCH1 protein is a type II membrane protein, has a short cytoplasmic tail (Met1 to Tyr21 (SEQ ID NO: 25), or Ala2 to Tyr21), a membrane anchor domain (Phe22 to Ser44, i.e., FYMAIFAVSVICVLYGP-SQQLSS (SEQ ID NO: 89)), a stem region, and a large C-terminal region containing the catalytic domain. See, e.g., Kim et al., *J. Biol. Chem.* 281:6261-6272 (2006); Nakayama et al., *EMBO* 11(7): 2511-2519 (1992); and Tu et al., *Cell. Mol. Life Sci.* 67:29-41 (2010).

The wild type OCH1 protein is generally localized in cis-Golgi. Golgi localization of the wild type OCH1 protein is believed to be dictated by the N-terminal region consisting of the cytoplasmic tail, the membrane anchor domain, and the stem region. In particular, the membrane anchor domain, including its amino acid constituents and length, plays an important role in the Golgi targeting of the protein. See, e.g., Tu et al. (supra).

The mutant OCH1 protein of this disclosure has an N-terminal sequence that alters the Golgi localization of the mutant OCH1 protein, as compared to the wild type OCH1 protein. As a result of this altered N-terminal sequence, the mutant OCH1 protein is either not properly targeted to or retained within the Golgi apparatus, or not properly targeted to or retained within the correct compartment within Golgi. The term "targeting" is meant the biological mechanisms by which proteins are transported to the appropriate destinations in the cell or outside of the cell. In specific embodiments, the mutant OCH1 protein of this disclosure lacks an N-terminal sequence that allows the Golgi targeting of the mutant OCH1 protein, such that the mutant OCH1 protein is not targeted the Golgi apparatus and is transported to another cellular location or secreted to outside of the cell.

In some embodiments, the alteration in the N-terminal sequence is a result of a mutation, i.e., addition, deletion or substitution, of one or more amino acids in the membrane anchor domain of the OCH1 protein. In specific embodiments, one or more amino acids in the membrane anchor domain have been deleted. In particular embodiments, at least 2, 3, 4, 5, 6, 7 or more amino acids, contiguous or otherwise, of the membrane anchor domain have been deleted. For example, some or all of the first 5 amino acids (FYMAI, SEQ NO: 90) of the membrane anchor domain are deleted.

In other embodiments, the alteration in the N-terminal sequence is a result of a mutation, i.e., addition, deletion or substitution, of one or more amino acids in the cytoplasmic tail of the OCH1 protein. In specific embodiments, one or more amino acids in the cytoplasmic tail have been deleted; for example, at least 2, 3, 4, 5, 6, 7 or more amino acids, contiguous or otherwise, of the cytoplasmic tail have been deleted. Examples of deletions in the cytoplasmic tail are found in Table 3. In other embodiments, deletion of one or more amino acids is combined with addition of one or more amino acids in the cytoplasmic tail.

In still other embodiments, the alteration in the N-terminal sequence is a result of a mutation of one or more amino acids in the stem region of the OCH1 protein; for example a deletion of one or more amino acids in the first 10, 20, 30, 40, 50, or 60 amino acids immediately following the membrane anchor domain.

In certain embodiments, the alteration in the N-terminal sequence is a result of a combination of mutations in the cytoplasmic tail, the membrane anchor domain, and/or the stem region of the OCH1 protein.

In specific embodiments, the alteration in the N-terminal sequence is a result of a combination of mutations in the cytoplasmic tail and the membrane anchor domain. For example, one or more amino acids in the cytoplasmic tail and one or more amino acids in the membrane anchor domain have been deleted. Examples of deletions in the N-terminal region of the OCH1 protein are listed in Table 3.

In other embodiments, in addition to deletions in one or more domains, one or more amino acids are added to the N-terminus of the protein, as long as the resulting mutant N-terminal sequence still fails to properly target or localize the OCH1 protein in Golgi. For example, the resulting mutant N-terminal sequence still lacks a functional membrane anchor domain. Whether a mutant sequence includes a membrane anchor domain can be readily determined based on the amino acid compositions and length. The membrane anchor domain of Golgi glycosyltransferases typically consists of 16-20 amino acids, which are hydrophobic and often contain aromatic amino acids, and has hydrophilic, often positively charged amino acids immediately outside both ends of the membrane span. See, e.g., Nakayama et al. (1992), supra. One example of a mutant OCH1 protein is set forth in SEQ ID NO: 3, which has its first 10 amino acids in place of the first 26 amino acids of the wild type OCH1 protein.

The mutant OCH1 protein disclosed herein contains a catalytic domain substantially identical to that of the wild type OCH1 protein.

The catalytic domain of the wild type OCH1 protein is located within the C-terminal fragment of 360 amino acids (i.e., within amino acids 45 to 404 of SEQ ID NO: 2). In some embodiments, the mutant OCH1 protein comprises a C-terminal fragment that is substantially identical to amino acids 45-404, 55-404, 65-404, 75-404, 85-404, 95-404, or 105-404 of SEQ ID NO: 2. By "substantially identical" it is meant that the sequences, when aligned in their full lengths, are at least 90%, 95%, 98%, 99%, or greater, identical. In most embodiments, the catalytic domain of the mutant OCH1 protein does not differ from the wild type domain by more than 10 amino acids, 8 amino acids, 5 amino acids, 3 amino acids, or 2 amino acids. In specific embodiments, the catalytic domain of the mutant OCH1 protein is identical with that of the wild type OCH1 protein. When one or more amino acids are different, it is preferable that the differences represent conservative amino acid substitutions. Examples of conservative substitutions include the substitution of a non-polar (hydrophobic) residue such as I, V, L or M for another; the substitution of one polar (hydrophilic) residue for another polar residue, such as R for K, Q for N, G for S, or vice versa; and the substitution of a basic residue such as K, R or H for another or the substitution of one acidic residue such as D or E for another.

The mutant OCH1 protein also substantially retains the catalytic activity of the wild type OCH1 protein, i.e., at least about 75%, 80%, 85%, 90%, 95% or more, of the α-1,6-mannosyltransferase activity of the wild type OCH1 protein. The activity of a particular OCH1 mutant protein can also be readily determined using in vitro or in vivo assays known in the art. See, Nakayama (1992), supra.

As described above, the strains of this invention include a mutant OCH1 allele which is transcribed into an mRNA coding for a mutant OCH1 protein, and do not include any other OCH1 allele that produces an mRNA coding for a functional OCH1 protein. Such strains can be engineered by a variety of means.

In some embodiments, the wild type OCH1 allele at the OCH1 locus on the chromosome of a *Pichia pastoris* strain has been modified or mutated to provide a mutant OCH1 allele (as illustrated in the Examples hereinbelow), or has been replaced by a mutant OCH1 allele (e.g., through homologous recombination). The modifications should be such that the resulting strain is stable with respect to the mutant OCH1 allele. That is, the mutant allele is maintained in the strain through generations (e.g., at least 10, 20, 30, 40, 50 or more cell divisions) suitable for both small volume flask culture and industrial size bioreactor culture, without reverting to an OCH1 allele coding for a functional OCH1 protein.

In other embodiments, a mutant OCH1 allele is introduced through an expression vector into a *Pichia pastoris* strain whose wild type OCH1 allele(s) (wild type OCH1 "allele" if haploid, or wild type OCH1 "alleles" if diploid) has already been disrupted hence no functional OCH1 protein is produced from the native OCH1 allele or native OCH1 locus. The expression vector can be an integrative vector designed to integrate the mutant OCH1 allele into the host genome; or a replicative vector (e.g., a plasmid) which replicates in the strain independent of the chromosomes.

Whether the mutant OCH1 allele is created at the native OCH1 locus by mutating or replacing the wild type OCH1 allele, or is provided via an expression vector in a strain whose wild type OCH1 allele(s) (wild type OCH1 "allele" if haploid, or wild type OCH1 "alleles" if diploid) has already been disrupted, it is important that the resulting mutant strain does not produce functional OCH1 protein through generations (e.g., at least 10, 20, 30, 40, 50 or more cell divisions). By "functional OCH1 protein" it is meant the wild type OCH1 protein or a functional equivalent of the wild type OCH1 protein, i.e., a protein that is targeted to Golgi and substantially retains the catalytic activity of the wild type OCH1 protein at least about 80%, 85%, 90%, 95% or more, of the α-1,6-mannosyltransferase activity of the wild type OCH1 protein). To avoid reversion, homologous sequences in the strain should be removed to avoid homologous recombination which generates a wild type OCH1 allele.

The mutant OCH1 allele, whether present on the host chromosome or on an extra chromosomal vector, is transcribed into mRNA. In other words, the strain is engineered such that the coding sequence of the mutant OCH1 allele is operably linked to a promoter to effect transcription. The promoter can be an endogenous promoter, such as the endogenous OCH1 promoter, a promoter heterologous to the OCH1 allele (e.g., an AOX1 promoter, a GAP promoter), and the like; or can be an exogenous promoter functional in *Pichia pastoris*. The level of transcription can be the same as, higher or lower than, the level of transcription of the wild type OCH1 allele in an unmodified *Pichia pastoris* strain (such as GS115).

*Pichia pastoris* strains having the genetic modifications to the OCH1 allele(s) described above include both haploid strains and diploid strains. For diploid strains having an OCH1 mutant allele integrated into a host chromosome, the strains can be either homozygous or heterozygous for the OCH1 mutant allele.

*Pichia pastoris* strains having the genetic modifications to the OCH1 allele(s) described above are robust and stable, and produce proteins with substantially homogeneous N-glycan structures with Man8GlcNAc2 being the predominant N-glycan.

Genetic Engineering—A Nucleic Acid Coding for and Expressing an α-1,2-Mannosidase In addition to the genetic modifications to the OCH1 allele(s) described above, the strains can be engineered to include a nucleic acid molecule which codes for and is capable of expressing an α-1,2-mannosidase or a functional fragment thereof which converts $Man_8GlcNA_{c2}$ to $Man_5GlcNA_{c2}$, thereby providing $Man_5GlcNA_{c2}$ as the predominant N-glycan form.

α-1,2-mannosidase (MS-I) is a well characterized family of enzymes. Most MS-I enzymes are known to be localized in the Golgi or endoplasmic reticulum, although a few are secreted and have extracellular activity. See, Gonzalez et al., *Mol Biol Evolution* 17:292-300 (2000). The topology of those enzymes that localize to the ER and the Golgi generally includes a luminal catalytic domain and an N-terminal transmembrane region. See, Herscovics, *Biochimie* 8: 757-62 (2001). The N-terminal region is composed of a stem region (closest to the luminal catalytic domain), a transmembrane domain, and a cytoplasmic tail. In the secreted MS-I enzymes, the extra-catalytic transmembrane region is also known as a leader sequence, serving as a signal for secretion of the enzyme. Detailed characterizations of various α-1,2-mannosidases can be found in Becker et al. (*European J. Cell Biol* 79: 986-992 (2000)) which studied the MS-I enzymes from mouse and *S. cerevisiae* and their catalytic domains; Schneikert and Herscovics (*Glycobiology* 4: 445-450 (1994)) which characterized the catalytic activity of a murine MS-I and its catalytic domain; Gonzalez et al. (*J. Biol Chem* 274: 21375-86 (1999)) which examined the activities and domains of several MS-I enzymes, including two enzymes from *C. elegans*, a human MS-I and the *S. cerevisiae* MS-I (from the ER); and Maras et al. (*J. Biotechnology* 77:255-263 (2000)), which characterizes the *T. reesei* α-1,2-mannosidase as belonging to the category of secretory MS-I's, which are composed of a catalytic domain and an N-terminal leader sequence.

The nucleic acid molecule encoding an α-1,2-mannosidase or a functional fragment thereof can derive from any species for use in this invention, including but not limited to mammalian genes encoding, e.g., murine α-1,2-mannosidase (Herscovics et al. *J. Biol. Chem.* 269: 9864-9871, 1994), rabbit α-1,2-mannosidase (Lal et al. *J. Biol. Chem.* 269: 9872-9881, 1994), or human α-1,2-mannosidase (Tremblay et al. *Glycobiology* 8: 585-595, 1998), fungal genes encoding, e.g., *Aspergillus* α-1,2-mannosidase (msdS gene), *Trichoderma reesei* α-1,2-mannosidase (Maras et al., *J. Biotechnol.* 77: 255-263, 2000), or a *Saccharomyces cerevisiae* α-1,2-mannosidase, as well as other genes such as those from *C. elegans* (GenBank Accession Nos. CAA98114 and CAB01415) and *Drosophila melanogaster* (GenBank Accession No. AAF46570) (see, e.g., Nett et al., *Yeast* 28:237-252, 2011, incorporated herein by reference).

By "functional part" or "enzymatically active fragment" of an α-1,2-mannosidase, it is meant a polypeptide fragment of a naturally occurring or wild type α-1,2-mannosidase which substantially retains the enzymatic activity of the full-length protein. By "substantially" in this context it is meant at least about 75%, 80%, 85%, 90%, 95% or more, of the enzymatic activity of the full-length protein is retained. For example, the catalytic domain of an α-1,2-mannosidase, absent of any N-terminal transmembrane or signal sequence, constitutes a "functional fragment" of the α-1,2-mannosidase. Those skilled in the art can readily identify and make functional fragments of an α-1,2-mannosidase based on information available in the art and a combination of techniques known in the art. The activity of a particular polypeptide fragment can also be verified using in vitro or in vivo assays known in the art.

In some embodiments, the nucleotide sequence coding for an α-1,2-mannosidase or a functional fragment is derived from the *Trichoderma reesei* α-1,2-mannosidase coding sequence. In specific embodiments, the nucleotide sequence codes for the *Trichoderma reesei* α-1,2-mannosidase described by Maras et al. *J. Biotechnol.* 77: 255-63 (2000), or a functional fragment thereof (such as the C-terminal catalytic domain of the full length protein).

In most embodiments, the strains are engineered such that the α-1,2-mannosidase or a functional fragment are targeted to the ER. In specific embodiments, the ER-targeting is achieved by including an ER-targeting sequence in the α-1,2-mannosidase or a functional fragment. Examples of ER-targeting sequences, i.e., sequences that target a protein to the ER so that the protein is localized or retained in the ER, include an N-terminal fragment of *S. cerevisiae* SEC12, an N-terminal sequence of *S. cerevisiae* α-glucosidase I encoded by GLS1, and an N-terminal fragment of *S. cerevisiae* α-1,2-mannosidase encoded by MNS1. See, also, Nett et al. (2011), supra. In a specific embodiment, the α-1,2-mannosidase or a functional fragment is targeted to the ER by including an ER-retention signal, HDEL (SEQ ID NO: 91), at the C-terminal of the α-1,2-mannosidase or its functional fragment.

The nucleic acid coding for an α-1,2-mannosidase or a functional fragment can be introduced through an expression vector into a *Pichia pastoris* strain. The expression vector can be an integrative vector designed to integrate α-1,2-mannosidase coding sequence into the host genome; or a replicative vector (e.g., a plasmid) which replicates in the strain independent of the chromosomes. In cases of an integrative vector, the vector can be designed to achieve integration of the nucleic acid into the wild type OCH1 allele (e.g., through single or double cross over homologous recombination) and simultaneous disruption of the wild type OCH1 allele.

SuperM5 Strains

This disclosure provides *Pichia pastoris* strains that are robust, stable, and transformable, and produce proteins with substantially homogeneous Man5GlcNAc2 N-glycans. These strains are also referred to herein as SuperM5 or SuperMan5 strains.

SuperM5 strains are genetically engineered to include a mutant OCH1 allele which is transcribed into an mRNA coding for a mutant OCH1 protein that contains a catalytic domain substantially identical to that of the wild type OCH1 protein, but lacks an N-terminal sequence necessary to target the OCH1 protein to the Golgi apparatus. The strains do not include any other OCH1 allele that produces an mRNA coding for a functional OCH1 protein. The strains are additionally genetically engineered to contain a nucleic acid coding for and expressing an α-1,2-mannosidase or a functional fragment thereof, which is targeted to the ER and converts Man8GlcNAc2 to Man5GlcNAc2.

An example of a SuperM5 strain is described in Example 1. The nucleotide sequence of the OCH1 locus of this strain is set forth in Table 1 and SEQ ID NO: 1. Constructed using the M5-Blast strain described in Jacobs et al. (2009), the SuperM5 strain is superior over M5-Blast in terms of robust growth, stability, and homogeneity of the M5 glycans produced.

Genetic Engineering—Introduction of Additional Enzymes

The strains can be additionally modified to express other, downstream enzymes (or functional fragments thereof) in the glycosylation pathway towards making hybrid- and complex-type N-glycans. Such additional enzymes include, e.g., one or more of GlcNAc transferase I (GnT-I), β-1,4-galactosyltransferase 1 (GalT), mannosidase II (Man-II), and GnT-II, among others. See Jacobs et al. (2009); U.S. Pat. No. 7,029,872 to Gerngross.

GnT-I catalyzes the addition of a β-1,2-linked GlcNAc residue to the α-1,3-mannose of the trimannosyl core in Man5GlcNAc2. Introduction of the GnT-I activity can be achieved by transforming with a vector comprising a nucleic acid sequence coding for a GlcNAc-transferase I (GnT-I) for use in this invention. Such nucleic acid sequence can derive from any species, e.g., rabbit, rat, human, plants, insects, nematodes and protozoa such as *Leishmania tarentolae*. In specific embodiments, the nucleotide sequence encodes a human GnT-I. The GnT-I or a functional part thereof is targeted to the Golgi apparatus, which can be achieved by including a yeast Golgi localization signal in the GnT-I protein or a functional part thereof. In certain embodiments, the catalytic domain of human GnT-I is fused to the N-terminal domain of *S. cerevisiae* Kre2p, a glycosyltransferase with a known cis/medial Golgi localization.

GalT catalyzes the addition of a galactose residue in β-1,4-linkage to the β-1,2-GlcNAc, using UDP-Gal as donor substrate. Introduction of the GalT activity can be achieved by transforming with a vector comprising a nucleic acid sequence coding for a GalT or a functional fragment thereof, which can derive from human, plants (e.g. *Arabidopsis thaliana*), insects (e.g. *Drosophila melanogaster*). The GalT or a functional part thereof is genetically engineered to contain a Golgi-retention signal and is targeted to the Golgi apparatus. An exemplary Golgi-retention signal is composed of the first 100 amino acids of the *Saccharomyces cerevisiae* Kre2 protein.

Man-II acts to remove both terminal α-1,3- and α-1,6-mannoses from GlcNAcMan5GlcNAc2 N-glycans. The presence of a terminal β-1,2-linked GlcNAc residue on the α-1,3-arm is essential for this activity. Introduction of the Man-II activity can be achieved by transforming a strain with a nucleic acid vector coding for a Man-II protein or a functional fragment thereof, engineered to contain a Golgi-localization signal. As an example, a suitable nucleic acid can encode the catalytic domain of *Drosophila melanogaster* Man-II, fused in frame to the Golgi-localization domain of *S. cerevisiae* Mnn2p.

GnT-II catalyzes the addition of a second β-1,2-linked GlcNAc residue to the free α-1,6-mannose of the trimannosyl core. Introduction of the GnT-II activity can be achieved by transforming with a vector which contains a nucleotide sequence coding for a GnT-II protein or a functional fragment thereof. GnT-II genes have been cloned from a number of species including mammalian species and can be used in the present invention. As an example, a suitable nucleotide sequence codes for the catalytic domain of rat GnT-II fused to the N-terminal part of *S. cerevisiae* Mnn2p.

Other Manipulations to the Strains

The strains disclose herein can include additional features, achieved by various suitable manipulations (such as cross or recombinant engineering), including, e.g., having a mutant auxotroph gene (e.g., his−) to facilitate cloning and selection, having protease deficiency for limiting product degradation (e.g., pep4−, prb1−, and/or sub2−), having a slow methanol utilization phenotype (e.g., mutS).

In specific embodiments, this disclosure provides the following strains:
SuperMan5, *P. pastoris*, och1−, blasticidin resistant, Mannosidase I from *T. reesei* (=His+);
SuperMan5 (his−), *P. pastoris*, och1−, his4−, blasticidin resistant, Mannosidase I from *T. reesei;*
SuperMan5 (mutS), *P. pastoris*, och1−, blasticidin resistant, Mannosidase I from *T. reesei* (slow methanol utilization);
SuperMan5 (pep4−), *P. pastoris*, och1−, blasticidin resistant, Mannosidase I from *T. reesei* (protease deficient);
SuperMan5 (prb1−), *P. pastoris*, och1−, blasticidin resistant, Mannosidase I from *T. reesei* (protease deficient);
SuperMan5 (pep4−, sub2−), *P. pastoris*, och1−, blasticidin resistant, Mannosidase I from *T. reesei* (protease deficient);
SuperMan5 (pep4−, prb1−), *P. pastoris*, och1−, blasticidin resistant, Mannosidase I from *T. ressei* (protease deficient).

Use of the Strains

A heterologous protein with one or more N-glycosylation sites can be expressed in the strains of this invention by transforming a strain of this invention with an expression vector coding for the heterologous protein, to obtain a preparation of the heterologous protein substantially homogeneous in its N-glycan structures.

Example 1

Generation of a SuperM5 Strain

This Example describes the creation of a SuperM5 strain from a M5-Blast strain described in Jacobs et al, (2009), *Nature Protocols* 4:58-70 (incorporated herein by reference).

The M5-Blast strain is a modification of the *P. pastoris* GS115 strain wherein the endogenous mannosyltransferase gene OCH1 is disrupted by the insertion of a vector comprising an α-1,2 mannosidase gene (pGlycoSwitchM5-Blast vector) through single crossover homologous recombination. As a result of the single crossover homologous recombination, the integrated mannosidase expression cassette is flanked by approximately 450 bp of homologous sequences from the OCH1 ORF. The sequence of the OCH1 genomic locus of this M5-Blast strain is set forth in SEQ ID NO: 53. Sequencing revealed the loss of 10 bp at the junction between the pGlycoSwitchM5-Blast vector sequence and the OCH1 ORF 3' fragment, resulting in the loss of one of the three desired stop codons from pGlycoSwitchM5-Blast vector upstream of the OCH1 C-terminal fragment, and frame shifted the second and third stop codons to a different reading frame than the fragment. As a result, the actual ORF was extended 28 bp upstream to an in-frame ATG codon in the vector backbone. Phe27 of the wild type protein became Phe11 of the new ORF, and the new predicted signal sequence consists partially of the old signal anchor and new, fused sequence from the vector backbone. The amino acid sequence of this new ORF is set forth in SEQ ID NO: 3 (with the first 25 amino acids being the predicted new signal sequence).

The N-terminal region of the OCH1 genomic locus after the single crossover homologous recombination event is diagrammed in FIG. 1, along with the construct used to remove this N-terminal region by double crossover homologous recombination. The construct contained both selection and counter-selection markers flanked by a lox71-lox66 pair, allowing for subsequent removal of the selection/counter-selection cassette by cre mediated recombination. The sequence of the double crossover selection/counter-selection cassette with homology arms is set forth in SEQ ID NO: 58, and its creation is described below in this Example.

In order to confirm the sequence of the targeted region prior to creating the crossover construct, PCR primers were designed to amplify ~1650 bp of DNA encompassing the region upstream of the mannosidase ORF. Using Phusion polymerase (NEB), PCR primers 80670918 and 80670919 amplified an appropriate sized fragment from M5-Blast genomic DNA. The PCR product was TOPO cloned and sequence verified. The DNA sequence demonstrated that the mannosidase expression vector had integrated into the GS115 genome correctly at this end of the insertion.

Figure 2:
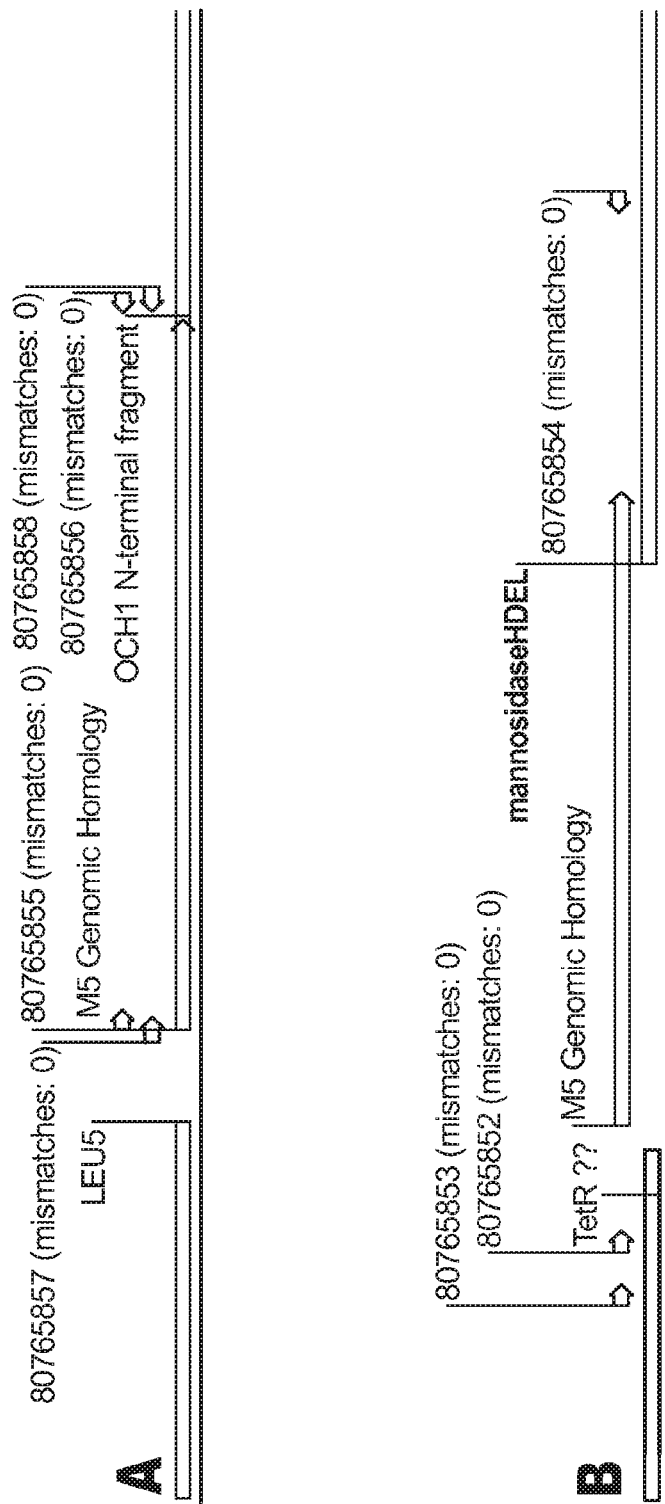
FIG. 2. PCR primers for amplification of flanking arms of double crossover construct from M5-Blast genomic DNA.

Flanking PCR primers were designed to amplify the homology regions shown in FIG. 1 from M5-Blast genomic DNA. The alignment of these PCR primers is shown in FIG. 2. Use of Phusion polymerase resulted in successful PCR reactions from M5-Blast genomic DNA.

PCR products for the following primer pair combinations were gel isolated and used as templates for the addition of lox71 and lox66 recombination sites:
80765855-80765856 (642 bp, FIG. 2A)
80765857-80765858 (658 bp, FIG. 2A)
80765852-80765854 (910 bp, FIG. 2B)
80765853-80765854 (956 bp, FIG. 2B)

Figure 3:
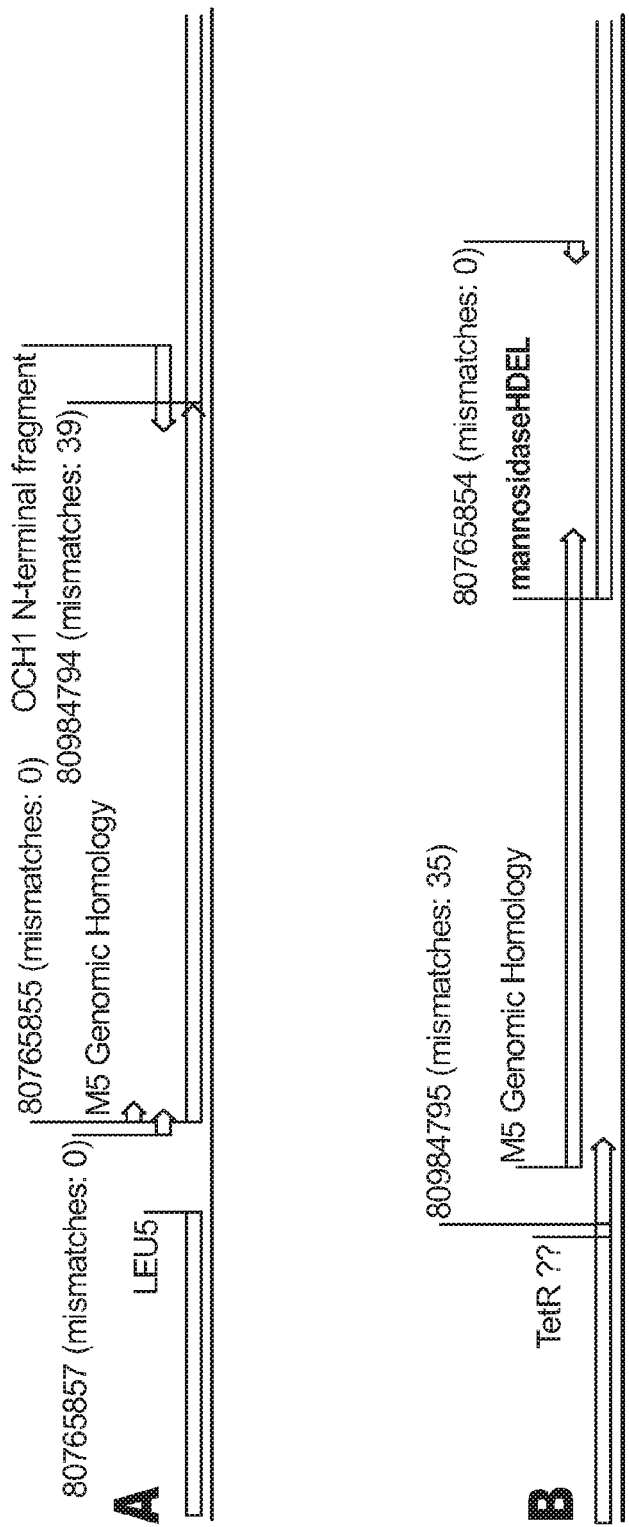
FIG. 3. PCR reactions for the addition of lox sites to the ends of the homology arms.

Mismatch PCR primers were designed to add the lox sites at the appropriate ends of the two homology arms. These mismatch primers are diagrammed in FIG. 3. PCR reactions with Phusion polymerase were successful in generating the correct sized DNA products from each of the 3 reactions:
80765855-80984794 (670 bp, FIG. 3A)
80765857-80984794 (681 bp, FIG. 3A)
80984795-80765854 (850 bp, FIG. 3B)

In addition to adding lox sites to the arms, PCR primers were designed to add appropriate M5-Blast *Pichia* genomic DNA extensions onto an existing lox71-MazF-Nat$^R$-lox66 cassette. Again, Phusion polymerase was used to generate the correct PCR product, as shown in FIG. 4. The primer pair used:
80984793-80984796 (2941 bp, FIG. 4)

The PCR product of the selection/counter-selection cassette was gel purified and a three piece overlap PCR was performed to attach the homology arms to the cassette.

Briefly, the three pieces were cycled 20× in the absence of primers to anneal and extend the overlap at the ends of the fragments. The cycled mix was then diluted and cycled 35× in the presence of the primers diagrammed in FIG. 5.

The PCR reaction was performed with Phusion polymerase, using an extension time of 3 min. Primers are detailed below:

80765855-80765854 (4311 bp, FIG. 5)

This PCR product was gel isolated and TOPO cloned. Selection of the TOPO cloning was performed on LB-Nat plates to ensure the inclusion of the selection cassette. DNA sequencing was performed on multiple isolates to determine the homology arm sequences. The final isolate contained a functional Nat$^R$ expression cassette, the lox71 and lox66 recombination sites and the correct homology arms.

Figure 6:
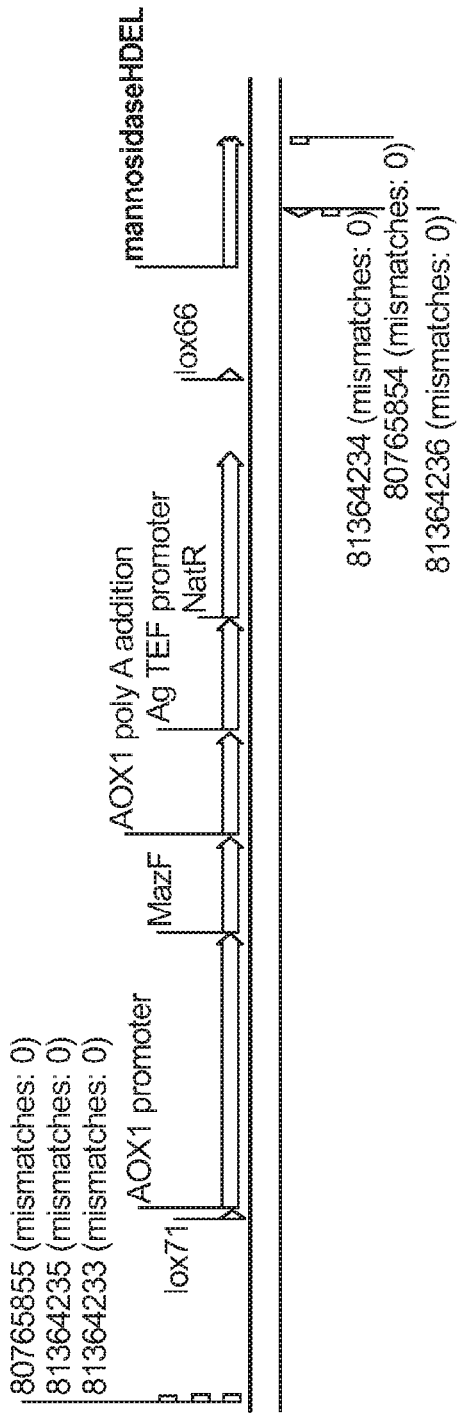
FIG. 6. PCR primer pairs used to generate DNA fragment for double crossover recombination event.

PCR primers internal to the cloned fragment detailed in FIG. 5 were used to generate linear DNA for *Pichia pastoris* transformation. Two independent sets of primers were designed:

81364233-81364234 (4063 bp, FIG. 6)
81364235-81364236 (4060 bp, FIG. 6)

PCR reactions were performed using Phusion polymerase with an extension time of 100 sec.

The PCR products were purified by agarose gel electrophoresis and eluted from the binding matrix with water. The M5-Blast *Pichia pastoris* strain was made competent for electroporation using a standard DTT/sorbitol treatment. Electroporation was performed using 1 mm cuvettes containing 20 μl competent cells and 1-2 μl of purified linear DNA. Transformation mixtures were plated on YPD-Nat agar.

Figure 7:
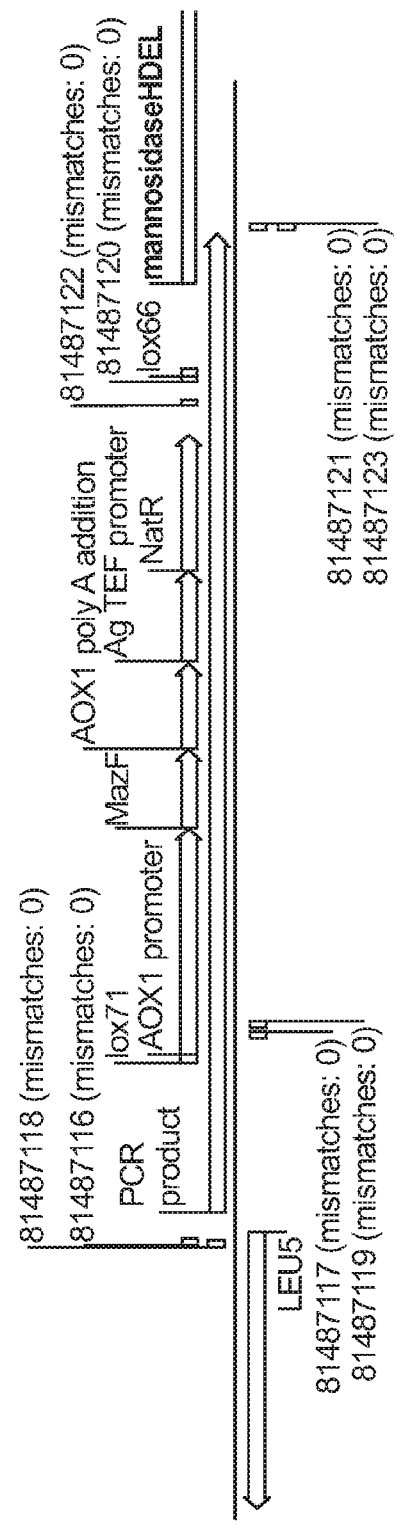
FIG. 7. Theoretical arrangement of LEU5-mannosidaseHDEL region of the M5-Blast genome after double crossover recombination event.

After electroporation, cells were grown out at 30° C. for 3 days. Individual transformants were patched to YPD-Nat for storage and analysis. FIG. 7 shows the theoretical arrangement of the OCH1 locus after proper double crossover integration of the PCR product(s) into the M5-Blast genome. PCR primer pairs were designed to check that the nourseothricin-resistant isolates were the result of homologous recombination, rather than random integration of the PCR product(s) into the genome. These PCR primer pairs are diagrammed on FIG. 7.

81487116-81487117 (895 bp, FIG. 7)
81487118-81487119 (937 bp, FIG. 7)
81487120-81487121 (656 bp, FIG. 7)
81487122-81487123 (756 bp, FIG. 7)

A total of 24 independent isolates were screened by PCR and 2 isolates that appeared correct were further characterized by DNA sequencing of the PCR products. The two isolates were struck to single colonies on YPD medium and retested on YPD-Nat. Small scale genomic DNA preparations were made using phenol/chloroform glass bead lysis. Based on the sequencing results of the 81487116-81487117, 81487118-81487119, 81487120-81487121 and 81487122-81487123 primer pairs on these genomic extracts, both isolates contained the lox71-lox66 selection/counter-selection cassette at the proper location in the M5-Blast genome. There were no mutations introduced by the initial PCR reaction to generate the transformation fragment, the recombination junctions at both ends were identical to M5-Blast "wild-type" DNA sequence, and both the lox71 and lox66 sites were intact. The DNA sequence of the OCH1 locus after double cross over recombination is set forth in SEQ ID NO: 59.

The two isolates (A1-2 and A4-3) were transformed with a plasmid constitutively expressing cre recombinase. Briefly, both strains were made electro-competent using a DTT/sorbitol procedure, electroporated with circular plasmid and plated on YPD-G418. Transformants were grown out at 30° C. for several days and colonies picked. Colonies were either transferred directly to methanol plates to induce the MazF counter-selection or patched to YPD to allow loss of the cre-ARS plasmid prior to MazF induction. Methanol induction was carried out on both BMMY (1% methanol) and CSM (complete synthetic medium, 0.5% methanol). Plates were supplemented with methanol daily by adding 100 μl methanol to the inverted plate lid. Incubation was carried out at 30° C. There was significant colony formation under all conditions tested; growth on methanol appeared independent of whether the transformant came directly from YPD-G418 or had undergone an intermediate patching on YPD without G418.

Figure 8:
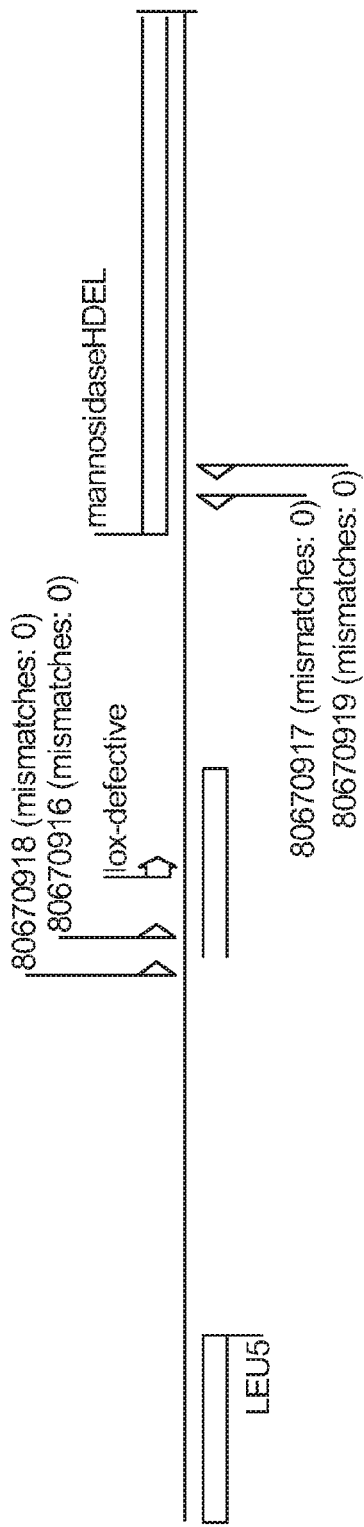
FIG. 8. Theoretical arrangement of genomic DNA between LEU5 and mannosidaseHDEL after cre recombination.

Cre recombination should remove the DNA sequences between the lox71 and lox66 sites, leaving only a defective lox site scar in the genome. The theoretical result of this recombination event is shown in FIG. 8. PCR primers were designed to amplify the region containing the detective lox scar. Twenty colonies that grew on methanol were screened by PCR to determine the loss of the selection/counter-selection cassette. PCR primers used were:

80670916-80670917 (680 bp, FIG. 8)
80670918-80670919 (782 bp, FIG. 8)

Seventeen of twenty isolates generated the appropriate PCR product with the first primer pair. Most, but not all, of the 17 also showed an appropriate product with the second primer pair. Each of the 17 isolates was patched to YPD, YPD-Blast, YPD-Nat and YPD-G418 to test for the presence or absence of the drug selection markers. If the cre plasmid had properly removed the selection/counter-selection cassette and subsequently been lost, the resulting strain should be blasticidin resistant and sensitive to both G418 and nourseothricin. All isolates were blasticidin resistant and nourseothricin sensitive. A few retained G418 resistance (still contained the cre plasmid, perhaps integrated) and were discarded. Of the remainder, 4 were picked for DNA sequencing of the LEU5-mannosidaseHDEL intergenic region.

Existing PCR primers were used to amplify the genomic region spanning LEU5 and the mannosidaseHDEL ORF.

Figure 9:
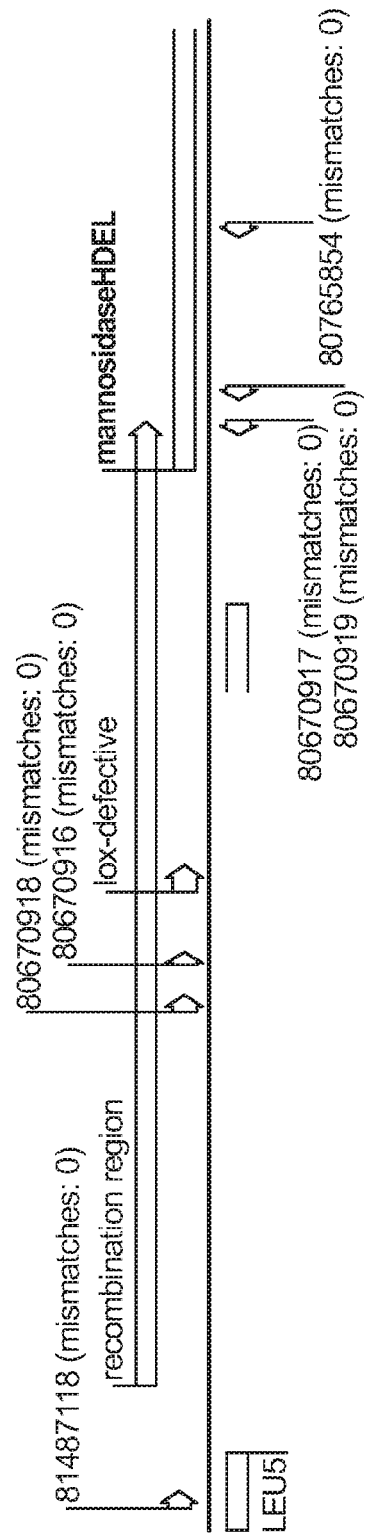
FIG. 9. PCR primers 81487118-80765854 used to verify DNA sequence of region that could have been derived from PCR products transformed into the M5-Blast strain.

81487118-80765854 (1602 bp, FIG. 9)

PCR amplification was performed using Phusion polymerase on genomic DNA that had been prepared by phenol/chloroform glass bead extraction. Multiple internal sequencing primers were used to verify the entire sequence of the 1602 bp PCR product. All 4 of the sequenced PCR products were correct, and contained a defective lox site at the proper location between the LEU5 gene and the mannosidaseHDEL ORF. Both the LEU5 promoter and the GAP promoter driving mannosidaseHDEL expression were intact and identical to the promoters present in the starting M5-Blast strain. The DNA sequence of the OCH1 locus after double crossover recombination and cre recombination is set forth in SEQ ID NO: 1.

Glycerol stocks of each of the 4 isolates (and 2 parental strains prior cre recombination) were prepared.

bG yeast-100015 A1-2 (pre-recombination)
    bG yeast-100016 A4-3 (pre-recombination)
    bG yeast-100017 isolate 1 (post-recombination)
    bG yeast-100018 isolate 2 (post-recombination)
    bG yeast-100019 isolate 3 (post-recombination)
    bG yeast-100020 isolate 4 (post-recombination)

Each glycerol stock was streaked and retested for the appropriate markers:

bG yeast-100015 his⁻, blasticidin$^R$, nourseothricin$^R$
    bG yeast-100016 his⁻, blasticidin$^R$, nourseothricin$^R$ bG yeast-100017 his⁻, blasticidin^R, nourseothricin^S
bG yeast-100018 his⁻, blasticidin^R, nourseothricin^S
bG yeast-100019 his⁻, blasticidin^R, nourseothricin^S
bG yeast-100020 his⁻, blasticidin^R, nourseothricin^S All glycerol stocks tested as expected.

YPD stabs of all 6 isolates were generated and subjected to glycoanalysis. Glycerol stock bG yeast-100017 was used to generate a large genomic DNA preparation for genomic sequencing. In addition, samples were prepared from wild-type GS115 and the M5-Blast strain. Briefly, cell pellets from 100 ml yeast cultures (YPD, 30° C. growth) were resuspended in 1 M sorbitol/100 mM citrate (pH 6.0) and treated with Zymolyase (Zymo Research) containing RNase for 2 h at 37° C. SDS was added to 0.5% to lyse spheroplasts. Proteinase K was then added and the mixture incubated at 50° C. overnight. An equal volume of phenol/chloroform was added and the mixture gently rocked for 30 min. After centrifugation, the upper aqueous layer was removed and DNA precipitated with isopropanol. The threaded DNA was spooled from the solution and resuspended in TE. The DNA was reprecipitated with ethanol and then washed with 70% ethanol, air-dried and resuspended a final time in TE.

DNA was distributed in multiple tubes:
bG DNA-100215 GS115 genomic DNA
bG DNA-100216 GS115 genomic DNA
bG DNA-100217 GS115 genomic DNA
bG DNA-100221 bG yeast-100017 genomic DNA
bG DNA-100222 bG yeast-100017 genomic DNA
bG DNA-100223 M5-Blast genomic DNA
bG DNA-100224 M5-Blast genomic DNA In order to test the genomic DNA isolates and verify that the manipulations performed in creating the bG yeast-100017 strain had not altered the mutant form of the OCH1 ORF, the N-terminal region of the OCH1 ORF was isolated from bG DNA-100221 (new strain) and bG DNA-100223 (M5-Blast strain) by PCR and resequenced. Both DNA preparations were identical at the OCH1 ORF locus, and contained the 10 bp deletion as described above.

Primers used in this Example are listed below:

| SEQ ID | | |
|---|---|---|
| 60 | 80670916 | CAAGTTGCGCCCCCTGGCA |
| 61 | 80670917 | TGGAGCAGCTAATGCGGAGGA |
| 62 | 80670918 | AGTTCCGCCGAGACTTCCCCA |
| 63 | 80670919 | TTCAGCCGGAATTTGTGCCGT |
| 64 | 80765852 | ATCCAGGGTGACGGTGCCGA |
| 65 | 80765853 | GCAAGAGGCCCGGCAGTACC |
| 66 | 80765354 | CCGCCCTCGTAGGGTTGGGAG |
| 67 | 80765855 | TTCGCGGTCGGGTCACACA |
| 68 | 80765856 | AACTGCCATCTGCCTTCGCC |
| 69 | 80765357 | CAAATCGCGGGTTCGCGGTC |
| 70 | 80765858 | GAGCAAACTGCCATCTGCCTTCG |
| 71 | 80984793 | GTGTTCGTAGCAAATATCATCAGCCTACCGTTCG TATAGCATACATTATACGAAGTTATGGATCTAAC ATCCAAA |
| 72 | 80984794 | TTTGGATGTTAGATCCATAACTTCGTATAATGTA TGCTATACGAACGGTAGGCTGATGATATTTGCTA CGAACAC |
| 73 | 80984795 | GCCGCCATCCAGTGTCATAACTTCGTATAGCATA CATTATACGAACGGTACTTTTTTGTAGAAAT GTCTTGGTGT |
| 74 | 80984796 | ACACCAAGACATTTCTACAAAAAAGTACCGTTCG TATAATGTATGCTATACGAAGTTATGACACTGGA TGGCGGC |
| 75 | 81364231 | GTGTTCGTAGCAAATATCATCAGCCTACCG |
| 76 | 81364232 | ACACCAAGACATTTCTACAAAAAAGTACCGT |
| 77 | 81364233 | TTCGCGGTCGGGTCACACAC |
| 78 | 81364234 | GGAGCAGCTAATGCGGAGGATGC |
| 79 | 81364235 | CGGTCGGGTCACACACGGAG |
| 80 | 81364236 | TGGAGCAGCTAATGCGGAGGA |
| 81 | 81487116 | TGAGTCCTGGTGCTCCTGACG |
| 82 | 81487117 | CCCCTCCTGTTGCGTTTGGC |
| 83 | 81487118 | AGCGTTCTGAGTCCTGGTGCT |
| 84 | 81487119 | GGTCCTGCGTTTGCAACGGT |
| 85 | 81487120 | ACTAACGCCGCCATCCAGTGTC |
| 86 | 81487121 | GCTTCAGCCGGAATTTGTGCCG |
| 87 | 81487122 | CGCCTCGACATCATCTGCCC |
| 88 | 81487123 | TCAGCCGGAATTTGTGCCGT |

Example 2

Storage and Handling

SuperM5 was stored in different conditions at −80° C., −4° C., 20° C. and at room temperature. Strains were stored as frozen glycerol stocks and as stab cultures. Different cultures were stored and thawed for different experiments and for shipping to collaborators for testing. In all cases the strains recovered, plated and cultured similar to the parent Pichia pastoris GS115 strain and grew in both complex and defined media similar to the parent strains. The SuperM5 strains transformed similarly as the parent strain and proteins were expressed with the mannose-5 glycosylation as the predominate glycoform, or the only glycoform. Strains have been repeatedly stored and regrown to establish robustness of the SuperM5 strains.

Example 3

Analysis of Test Proteins in P. pastoris Strains

The genes for Candida antartica lipases A and B, human transferrin, and the human CH2 domain from IgG were integrated into the SuperM5 genome using standard transformation methods. In all cases significant amounts of protein were produced and secreted into the medium. Transformed strains and media-containing protein were tested for glycan analysis using previously published methods. In all cases, the glycan profiles for the test proteins and for the strain glycoproteins demonstrated a mannose-5 glycan structure with no other higher mannose structures detected by the methods used.

Example 4

Analysis of Cell Wall Mannoproteins in *P. pastoris* Strains

Twelve *Pichia pastoris* strains and the Man5-Blast strain were started in a 24-well plate containing 2 ml YPD and grown overnight at 28° C. while shaking (250 rpm). After growth, cells were harvested by centrifugation (3000 g for 5 min at room temperature) and cell wall mannoproteins were extracted according to the protocol by Jacobs et al. (see Jacobs et al., 2009, *Nature Protocols* 4(1):58-70). The extracted mannoproteins (in 100 μl ddH20) were diluted to 300 μl with RCM buffer (8 M urea, 3.2 mM EDTA, 360 mM Tris-HCL, PH 8.6), N-glycans were prepared from these samples following the 96-well on-membrane deglycosylation procedure as published by Laroy et al. (Laroy et al., 2006, *Nature Protocols*, 1: 397-405).

Figure 10:
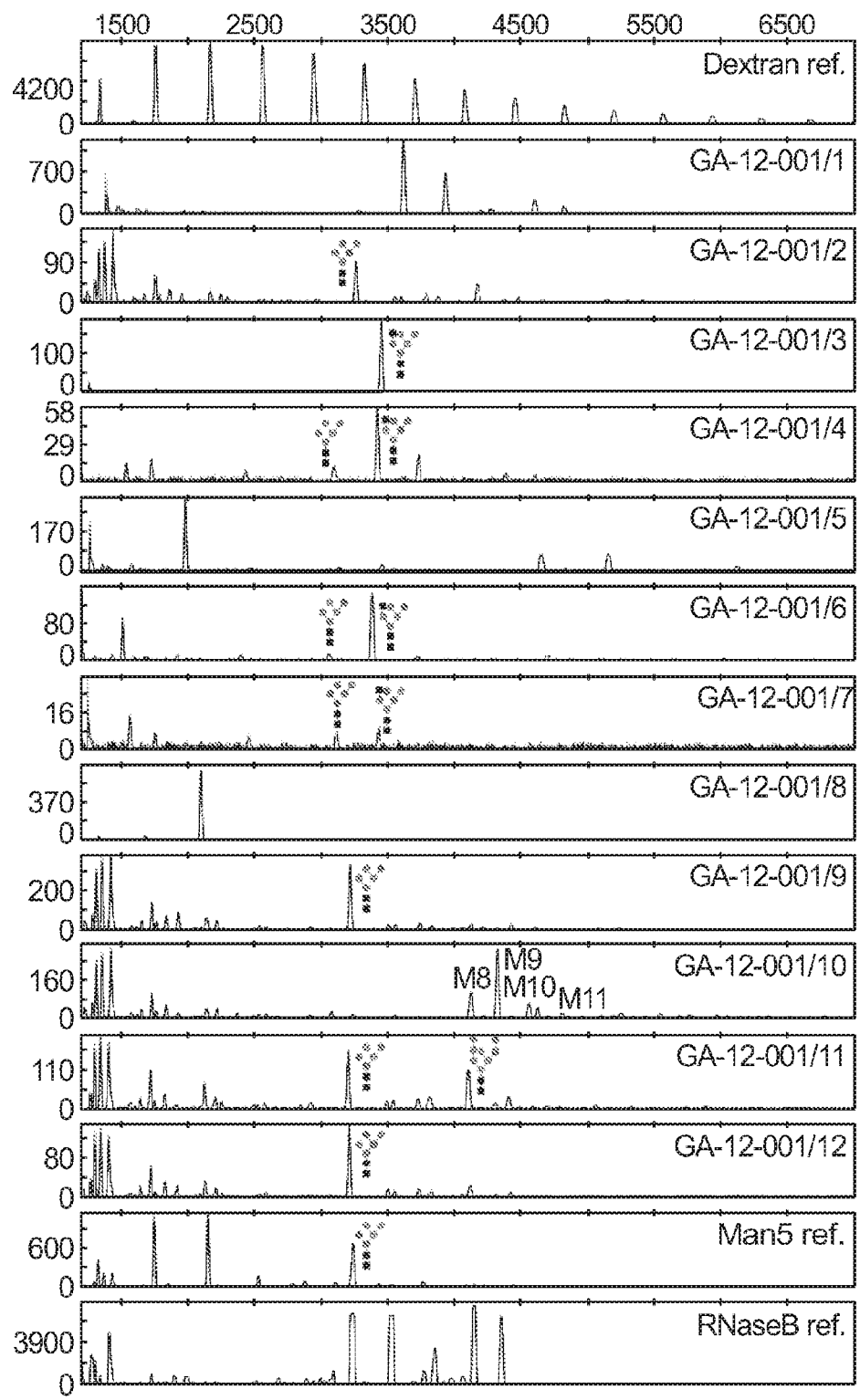
FIG. 10. N-glycan analysis of a recombinant protein expressed in various *P. pastoris* strains.

After labeling the dried N-glycans with 8-aminopyrene-1,3,6-trisulphonic acid2, the excess of label was removed using size exclusion chromatography (Sephadex G-10 resin2). The samples were finally reconstituted in 10 μl of ultrapure water and diluted 10× prior to their injection (80" at 1.2 kV) in the capillaries (e.l. 36 cm; i.d, 50 μm) of an ABI 3130 DNA sequencer. The following settings were applied: Oven temperature: 60° C. Run voltage: 15 kV; Prerun voltage: 180" Run time: 1000"; Prerun time: 15 kV. The Genemapper v3.7 was used to analyze the obtained data and structures were assigned to the peaks (see FIG. 10).

Example 5

Materials and Methods

Below describes non-limiting examples of materials and methods for the present invention.

Plasmids and strains: *Pichia pastoris* expression vector pPICZαA was purchased from Invitrogen Corporation; pUC19/GM-CSF plasmid (containing GM-CSF Gene sequence) was synthesized by Shanghai Qing-Lan Biotech Co., Ltd.; *Saccharomyces cerevisia* expression vector pYES2, *Pichia pastoris* X-33 (wild Type), *E. coli* JM109 were from the inventors' laboratory.

Reagents and instruments: Taq DNA polymerase, Pfu DNA polymerase, restriction enzymes, T4 ligase, 5-fluoroorotic acid (5-FOA) was purchased from Shanghai Biological Engineering Technology Services Co., Ltd.; Zymolyase was purchased from Sigmag company (USA); N-glycosidase F (PNGase F) was purchased from New England Biolabs, Inc. (USA); peptone, yeast extract, yeast nitrogen base without amino acids (YNB) were purchased from BIO BASIC INC (Canada). PCR machine (PTC100) was from MJ Research, Inc. (USA); electrophoresis systems, gel imaging system were from Bio-Rad (USA); AKTA purification system purchased from GE (USA).

Primers: based on the reported *Pichia* URA3 (orotidine-5'-Phosphate decarboxylase) gene sequence (GenBank: AF321098), two pairs of extension amplification primers based on homologous fragment were designed: URA5F, URA5R and URA3F, URA3R; based on *Saccharomyces cerevisiae* expression vector pYES2 sequence, primers pYES2F and pYES2R were designed; based on the GenBank (E12456) reported *Pichia* OCH1 gene sequence, two pairs of amplification primers based homologous sequence were designed: OCH5F, OCH5R and OCH3F, OCH3R. The internal identification primers (in) 5F, (in) 3R were also based on the same sequence; universal primers 5' AOX1, 3' AOX1 sequences were based on references. Primers were synthesized by Shanghai Biological Engineering Technology Services Co., Ltd.

Yeast cell culture, genomic extraction and PCR conditions were performed based on known protocols.

The construction of URA3 homologous replacement DNA sequence: using the X-33 strain genome as a template and primer pairs URA5F, URA5R and URA3F, URA3R, the homologous fragments of both sides of URA3 genes, URA5' and URA3', a 700 bp and a 600 bp, respectively, were PCR amplified. Then using URA5' and URA3' as templates and URA5F and URA3R as a primer pair, the URA5-3, the target homologous replacement DNA fragment for URA3 gene was PCR amplified, which was about 1300 bp in size.

The construction of pYXZ plasmid: using plasmid pYES2 as a template and primer pair pYES2F and pYES2R, the sequence that contains URA3 gene was PCR amplified. The PCR product was purified and digested with Sal I and followed with ligation reaction. The self-ligased plasmid pYXZ was transformed into *E. coli* JM109, and plated on LB plates containing ampicillin to select positive clones.

The cloning of OCH1 homologous arm: using the X-33 strain genome as a template and primer pairs OCH5F, OCH5R and OCH3F, OCH3R, to PCR amplify the 5' and 3' ends of the OCH1 gene homologous arms, OCH5' and OCH3' and its fusion fragment OCH3-5. The method used was similar to what has been described above. The fragment sizes were 1000 bp, 700 bp and 1700 bp, respectively.

The construction of Knockout plasmid pYXZ-OCH1: the inventors digested the OCH1 gene 5' and 3' homologous fusion fragment OCH3-5 with Nhe I and Sal I and cloned the fragment into pYXZ plasmid digested with Sal I and Nhe I to make the knockout plasmid pYXZ-OCH1.

Knockout the URA3 gene from *Pichia pastoris* X-33 to construct auxotrophic selection marker: X-33 competent cells were shock transformed using the fusion fragment URA5-3 arm that has homologous sequence to both ends of the URA3 gene; the transformed cells were spread on MD medium containing 5-FOA and uracil (YNB 1. 34%, glucose 2%, agar 1.5%, uracil 100 μg/mL, 5-FOA 1 mg/mL), and incubated at 30 degrees Celsius for 3-5 days. Single colonies grown on the medium were selected and seeded with a toothpick, respectively, to MD medium (YNB 1. 34%, glucose 2%, agar 1.5%) and MDU medium (YNB 1. 34%, glucose 2%, agar 1.5%, uracil 100 μg/mL), and incubated at 30 degrees Celsius for 3-5 days. Then, strains that grew well on the MDU medium but could not grow on the MD medium were selected. The selection process was repeated for 3 rounds to get stable traits and the final strains were confirmed by PCR reaction using URA5F, URA3R as primers and genomic DNA as template.

OCH1 gene knockout of *Pichia pastoris* X-33: the knockout plasmid pYXZ-OCH1 was linearized at Mlu I site that is located between the two homologous arms and electric shock transformed into the X-33 (ura3−) competent cells, and spread on MD medium, and incubated at 25 degrees Celsius for about a week. Single colonies were picked with a toothpick and seeded to the same coordination on two plates with YPD medium (peptone 2%, yeast extract 1%, glucose 2%, agar 1.5%), and incubated at 25 degrees Celsius and 37 degrees Celsius, respectively for a few days. The colonies that grew well at 25 degrees Celsius but could not grow at 37 degrees Celsius were extracted to obtain genomic DNA. OCH1 gene external primers OCH5F, OCH3R and internal primers (in) 5F, (in) 3R were used for PCR identification.

Construction of expression vector: the plasmid pUC19/GM-CSF from the inventors' own laboratory was double digested with EcoRI and Not I. The GM-CSF gene fragment was extracted (a 6×His tag sequence was introduced), and cloned into *Pichia pastoris* expression vector pPICZαA digested with the same restriction enzymes to make the expression vector pPICZαA/GM-CSF. Positive clones were selected and confirmed with restriction enzyme digestion and sequencing.

The expression and analysis of GM-CSF in *Pichia pastoris* X-33 and X-33 (och1-): linearize the expression vector pPICZαA/GM-CSF with Sal I and electrically shock transformed the plasmid into X-33 and X-33 (och1-) competent cells. Shock mixture was spread to culture cloth coated with YPDZ medium (each containing 100 μg/mL, 300 μg/mL, or 500 μg/mL Zeocin), the X-33 transformants were grown at 30 degrees Celsius for 3-5 days, and X-33 (och1-) transformants were cultured at 25 degrees Celsius for about a week. Single colonies that grew well were picked to extract genomic DNA and identified with PCR reaction using primers 5'AOX, 3' AOX1 to select positive transformants. Positive X-33/PICZαA/GM-CSF cells were inoculated into 2 mL of YPD medium (2% peptone, 1% yeast extract, 2% glucose), incubated at 30 degrees Celsius for 24 h. The culture was used to inoculate (5% inoculation ratio) into 10 mL of BMGY medium (2% peptone, yeast extract 1%, YNB 1.34%, glycerol 2%, 100 mmol/L phosphate buffer, pH 6.0). After incubation at 30 degrees Celsius for 36 h, the culture was centrifuged to remove the supernatant and the pellet was resuspended to 3 mL of BMMY medium (yeast extract 1%, YNB 1.34%, peptone 2%, 100 mmol/L phosphate buffer, PH 6. 0), 2% methanol was added to induced expression: X-33 (och1-)/pPICZαA/GM-CSF positive cells were cultured in the YPD medium at 25 degrees Celsius for 48 h, BMGY at 25 degrees Celsius for 48 h, and induced expression at 25 degrees Celsius. Expression induction condition was same as that used in X-33 cells, methanol was added every 24 h and the induction was for 72 h. Once it was finished, the cell cultures were centrifuged and supernatant was collected for protein analysis.

Example 6

Transcriptome Analysis of M5-Blast and SuperM5 Strains

Strain Growth For RNA Isolation. BG10, GS115, M5 Blast and SuperM5 (described in Example 1) strains were maintained on YPD Agar plates as patches. For transcriptome analysis, a 50 ml culture of each strain was inoculated from a patch and grown in BMGY at 30° C., 200 min for approximately 16 hours. The stationary culture was diluted 100-fold into fresh BMGY medium and grown at 30° C., 200 rpm for 6 hours. This time point was considered exponential growth with glycerol as the carbon source. Aliquots were spun down in 15 ml tubes, supernatants discarded and the cell pellets rapidly frozen in liquid nitrogen. Cell pellets were stored at −80° C. for subsequent total RNA isolation.

Total RNA Isolation. FastRNA SPIN kits (MP Bio) were used to isolate total RNA. Cell lysis was per-formed using a BioSpec Mini-Beadbeater 96. Total RNA was eluted from the spin column in 15 μl of RNase/DNase-free water, frozen in liquid nitrogen and stored at −80° C. RNA samples were shipped on dry ice for RNA-Seq analysis on an Illumina HiSeq machine. RNA samples were analyzed using an Agilent BioAnalyzer, and all showed intact yeast ribosomal RNA peaks.

RNA Library Generation and Sequencing. mRNA libraries were prepared using Illumina reagents. A TruSeq RNA Sample Preparation Kit was used to selectively generate bar-coded cDNA from polyA RNA. After bar-coding and amplification, a total of 12 samples were pooled (4 samples for this study) for analysis. Fifty base, single end reads were performed. Data was supplied to BioGrammatics in standard FASTQ format. Reads were trimmed based on ambiguous bases and quality score and then filtered to eliminate all trimmed reads that were less than 40 bases in length. Approximately 0.3% of reads were removed from each data set.

The RNA-Seq algorithm of CLC Genomics Workbench was used to map the reads from each data set to the BG10 wild type annotated sequence. Note that the BG10 genome does not contain the expression cassettes for the mannosidase and blasticidin resistance gene present in the Man5 and SuperM5 strains.

Gene Expression Profiling. Expression profiles from each of the 4 strains were plotted and clustered. Scatter plots (with R-values) were evaluated for strain to strain comparisons of overall expression profiles. The BG10 and GS115 strains show the tightest correlation (R-value=0.98), followed by the Man5 and SuperM5 strains (R-value=0.95). A slight general upregulation was observed in the OCH1 mutant strains vs. GS115 (R-values of 0.92 and 0.84 for Man5 and SuperM5 respectively). Overall, gene expression patterns are similar amongst the 3 strains (GS115, M5 and SuperM5) when grown on glycerol.

From each of the RNA-Seq data sets mapping to the BG10 strain, the OCH1 mapping was extracted. In the BG10 and GS115 strains, the coverage scale was from 0 to about 75. The expression levels of OCH1 were approximately equal. Sequencing reads were distributed approximately equally across the open reading frame. The expression levels of OCH1 in these two strains were approximately 0.2% that of the most highly expressed genes.

For the SuperM5 strain, the coverage scale was from 0-47. The expression level dropped to approximately half that of the BG10 and GS115 strains. Also, there was no coverage of the N-terminus of the open reading frame. This lack of coverage was the result of the complete deletion of these DNA sequences from the SuperM5 strain.

For the Man5 strain, the coverage scale was from 0-502. There was significantly more coverage of the N-terminal portion of the open reading frame than the C-terminal portion. This disjointed coverage was the result of the duplication of most of the N-terminal portion of the open reading frame in the Man5 strain. The N-terminal portion of the ORF is expressed from DNA upstream of the mannosidase ORF and the mutant form of the C-terminal portion of the ORF was expressed downstream of the mannosidase and blasticidin resistance ORFs. Based on read coverage, the C-terminal portion of the ORF appears to be slightly less abundant in Man5 than in SuperM5.

Mapping of the Man5 and SuperM5 data to the mutant form of the OCH1 ORF shows complete coverage of the mutant OCH1 ORF in both strains, indicating gene expression. The $Man_5$ strain shows extra coverage in the N-terminal portion of the ORF, for the same reasons described above for the wild type OCH1 ORF mapping.

Mapping of the Man5 and SuperM5 data to the mannosidase ORF shows similar expression levels in the two strains.

Conclusion

Transcriptome analysis has been performed on the GS115, Man$_5$ and SuperM5 strains. The strains show similar overall gene expression patterns. In the Man and SuperM5 strains, a mutant form of the OCH1 ORF is expressed (polyadenylated mRNA is present). The mannosidaseHDEL ORF is expressed in both strains at approximately the same level.

Example 7

Trastuzumab Expression in a M5-Blast Like and SuperM5 Strains

In Study 1, the SuperM5 strain described in Example 1 was transformed with an expression vector coding for trastuzumab by electroporation. Zeocin-resistant colonies were screened by the genome PCR using AOX1 primers and Herceptin specific primers. Positive clones of the genome PCR was cultivated and Man5-type trastuzumab expression to the culture supernatants was evaluated by SDS-PAGE.

In Study 2, Pichia strains transformed with an expression vector coding for trastuzumab were screened to select a strain that expressed high levels of trastuzumab. The selected strain was transformed with GlycoSwitch® plasmid (pGlycoSwitch-M5/2 (GAP, BSD), provided by Gent University) by eletroporation. Blasticidin S-resistant colonies were screened by the genome PCR for detecting the pGlycoSwitch-M5 insertion into the OCH1 locus and MDS1 gene presence. Positive clones of the genome PCR was cultivated and Man5-type trastuzumab expression to the culture supernatants was evaluated by SDS-PAGE.

In Study 3, the positive clones obtained in Study 1 (clone 46) and Study 2 (clone 11) were cultivated in a 1 L baffled flask. Trastuzumab expression was induced by replacing with methanol containing medium. 72 hours after methanol induction, trastuzumab was purified using Protein A-affinity resin from the culture supernatants. Productivity of trastuzumab from clone 46 and clone 11 was 3 mg/L and 1.3 mg/L culture, respectively.

Figure 11:
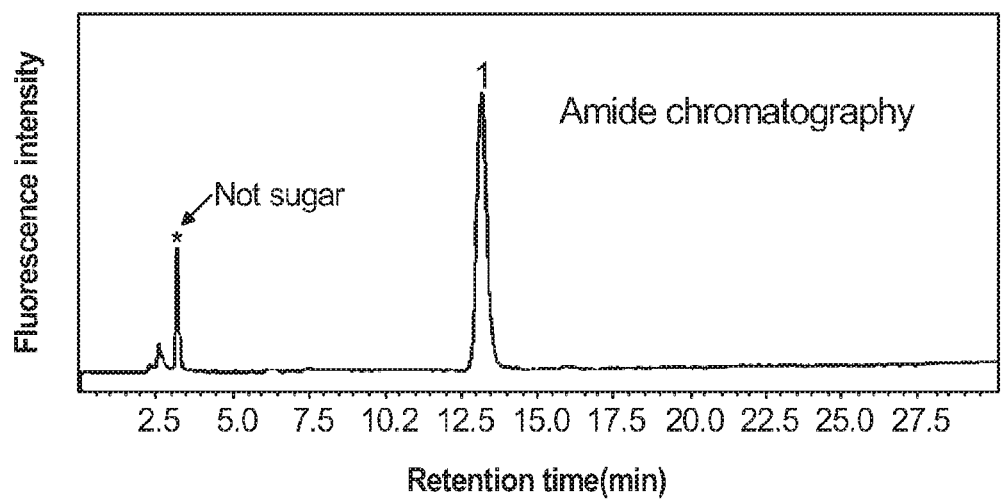
FIG. 11. N-glycan analysis of trastuzumab obtained in Study 1 described in Example 6.

In Study 4, the N-glycan structures of trastuzumab produced in clone 46 (Study 1) and clone 11 (Study 2) were analyzed. The homogeneity of N-glycan structures was assessed in the primary analysis, and the N-glycan structures were identified in the secondary analysis according to searching N-glycan database and HPLC injection along with the standard sample. From these analyses, the N-glycans of trastuzumab obtained from clone 46 (Study 1) were virtually homogeneous and the predominant (or essentially the only) N-glycan was estimated as Man5GlcNac2 from MALDI-TOF mass analysis (FIG. 11). The N-glycan structures of trastuzumab obtained from clone 11 (Study 2) were found to be a mixture of Man5GlcNAc2 to Man8GlcNAc2.

TABLE 7

N-glycan analysis of trastuzumab obtained from Study 2

| N-glycan | ODS (GU) | Amide (GU) | MW (Da) | Composition (%) | Quantitative value (pmol/mg) | Estimated N-glycan structure |
|---|---|---|---|---|---|---|
| N1-1 | 4.7 | 9.7 | 1962 | 7.4 | 161 | (Hexose)$_9$(HexNAc)$_2$ |
| N1-2 | | 10.7 | 2124 | 4.6 | 101 | (Hexose)$_{10}$(HexNAc)$_2$ |
| N2-1 | 5.0 | 8.8 | 1800 | 22.3 | 487 | Man$_8$GlcNAc$_2$ |
| N2-2 | | 10.1 | 2124 | 7.1 | 154 | (Hexose)$_{10}$(HexNAc)$_2$ |
| N3 | 5.2 | 7.9 | 1638 | 7.4 | 161 | Man$_7$GlcNAc$_2$ |
| N4-1 | 6.1 | 7.0 | 1475 | 16.9 | 370 | Man$_6$GlcNAc$_2$ |
| N4-2 | | 7.9 | 1638 | 11.1 | 241 | (Hexose)$_7$(HexNAc)$_2$ |
| N5 | 7.3 | 6.0 | 1313 | 22.1 | 481 | Man$_5$GlcNAc$_2$ |
| Others | | | | 1.1 | | |
| Total | | | | 100 | | |

Figure 12:
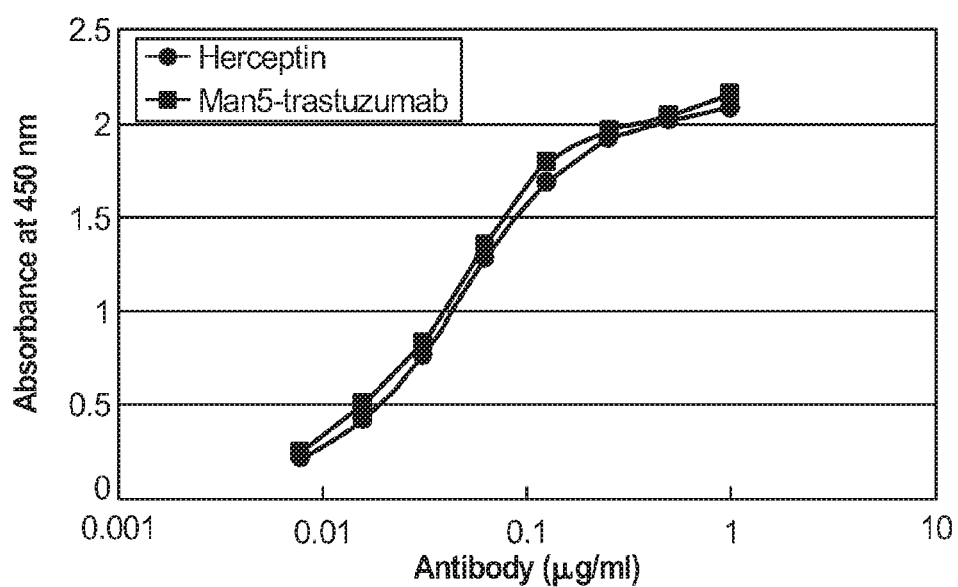
FIG. 12. Comparison of Her2 binding affinity of Man5-type trastuzumab (Study 1) and commercial Herceptin by ELISA.

Her2 binding affinity of Man5-type trastuzumab obtained from clone 46 was analyzed in parallel with commercial Herceptin by ELISA and BIAcore assays, was found to have similar HER2-binding activity to the commercial Herceptin. See FIG. 12 and Table 8.

TABLE 8

Kinetic parameters of trastuzumab analyzed on BIAcore

| mAb | $k_a$ (M$^{-1}$ s$^{-1}$) | $k_d$ (s$^{-1}$) | $K_A$ (M$^{-1}$) | $K_D$ (nM) |
|---|---|---|---|---|
| Man5-trastuzumab | 2.29 × 10$^5$ | 2.43 × 10$^{-5}$ | 1.20 × 10$^{10}$ | 0.083 |
| CHO Herceptin | 4.25 × 10$^5$ | 5.21 × 10$^{-5}$ | 8.17 × 10$^9$ | 0.12 |
| Pichia trastuzumab | 4.65 × 10$^5$ | 8.72 × 10$^{-5}$ | 5.33 × 10$^9$ | 0.19 |

Example 8

Analysis of Additional Glycosylated Proteins Expressed in M5-Blast and SuperM5

Genes for Candida antarctica lipases A and B (CalA, 2 N-glycosylation motifs and CalB, 1 N-glycosylation motif) as well as for human serum transferrin (2 N-glycosylation motifs), driven by an AOX1 promoter, were integrated into the genome of the M5-Blast strain as well as the SuperM5 strain, both described in Example 1, via homologous recombination at the AOX1 locus (selection by Zeocin). A plasmid harboring a complementation cassette for histidine auxotrophy next to a synthetic gene coding for native Pichia PDI that is driven by an AOX1 promoter, was co-transformed. Selection was done on solid minimal media with Zeocin.

47 transformants of each combination described above were cultivated and screened for protein abundance and quality with respect to obvious changes in the migration behavior of the secreted proteins on microCE (capillary electrophoresis, GXII, CaliperLS). Mock strain supernatant (GS115) was applied as negative control.

All 3 proteins secreted from the SuperM5 strain showed comparable expression levels as compared to the M5-Blast strain. Furthermore, target protein signals from the SuperM5 supernatants on microCE exhibited a lowered migration time as those from M5-Blast supernatants, shifting to lower apparent molecular weights. It is believed that altered N-glycosylation of secreted proteins from SuperM5 resulted in a lower molecular mass in microscale.

Samples of the supernatants from microscale cultures and those from cultures in a bioreactor were analyzed for its N-glycan compositions. From the samples obtained from microscale culture, 0.5 ml of the medium was diluted with two times the volume of RCM buffer (8 M urea, 3.2 mM EDTA, 360 mM Tris-HCL, PH 8.6). From the bioreactor samples, 0.2 ml medium was used. N-glycans were prepared from these samples following the 96-well on-membrane deglycosylation procedure as published by Laroy et al. (supra). After labeling the dried N-glycans with 8-aminopyrene-1,3,6-trisulphonic acid, the excess of label was removed using size exclusion chromatography (Sephadex G-10 resin). The samples were finally reconstituted in 10 µl of ultrapure water and diluted 10× prior to their injection (80" at 1.2 kV) in the capillaries (e.l. 36 cm; i.d. 50 µm) of an ABI 3730 DNA sequencer. The following settings were applied:

Oven temperature: 60° C. Run voltage: 15 kV
Prerun voltage: 180" Run time: 1000"
Prerun time: 15 kV The Genemapper v3.7 was used to analyze the obtained data and structures were assigned to the peaks.

Figure 13:
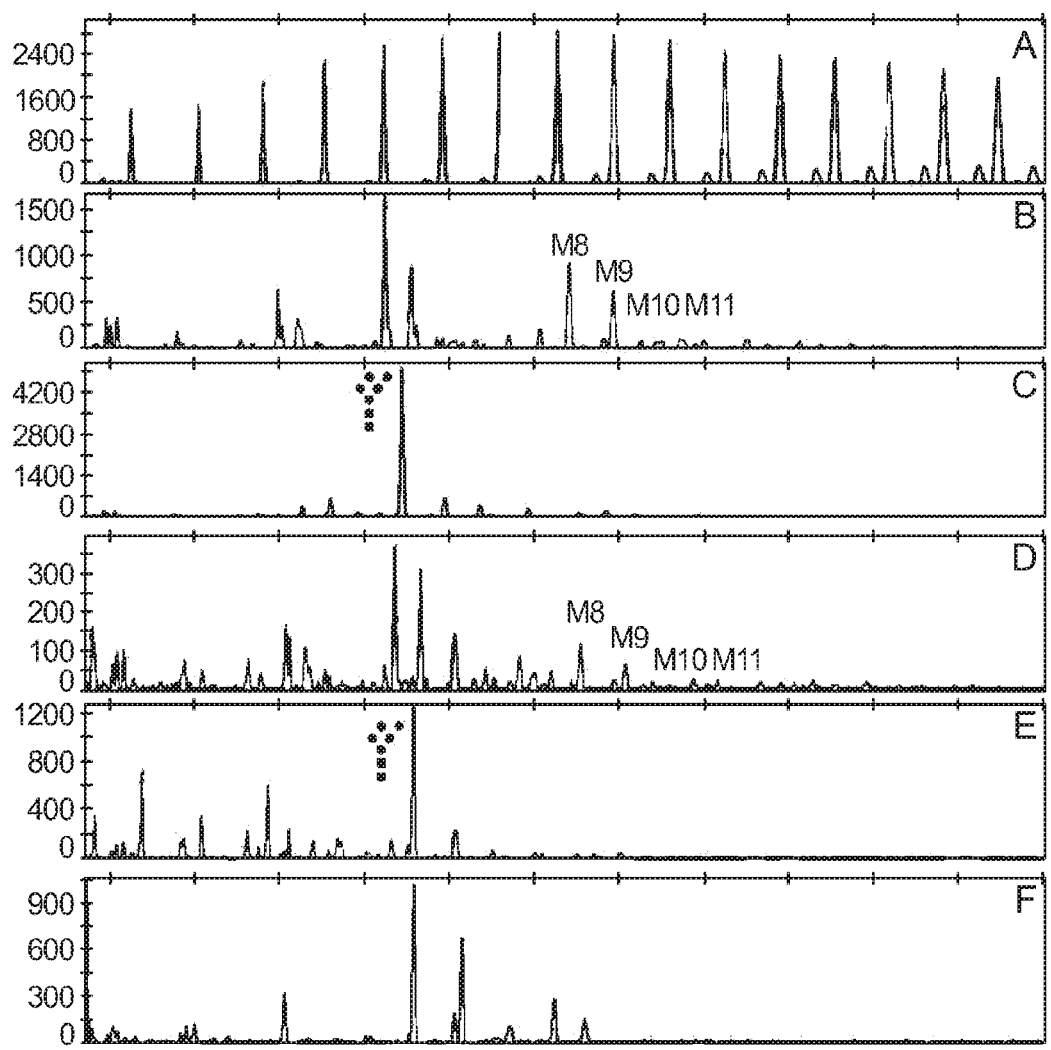
FIG. 13. DSA-FACE analysis of the total N-glycan pool on medium proteins from 'Trans' strains. A. result for a malto-dextrose reference. Panel B to F show results for N-glycans, as follows: B. GS Trans strain in microscale; C. M5 Trans strain in microscale; D. GS Trans strain in bioreactor; E. M5 Trans strain in bioreactor; F. reference N-glycans from bovine RNase B.
Figure 14:
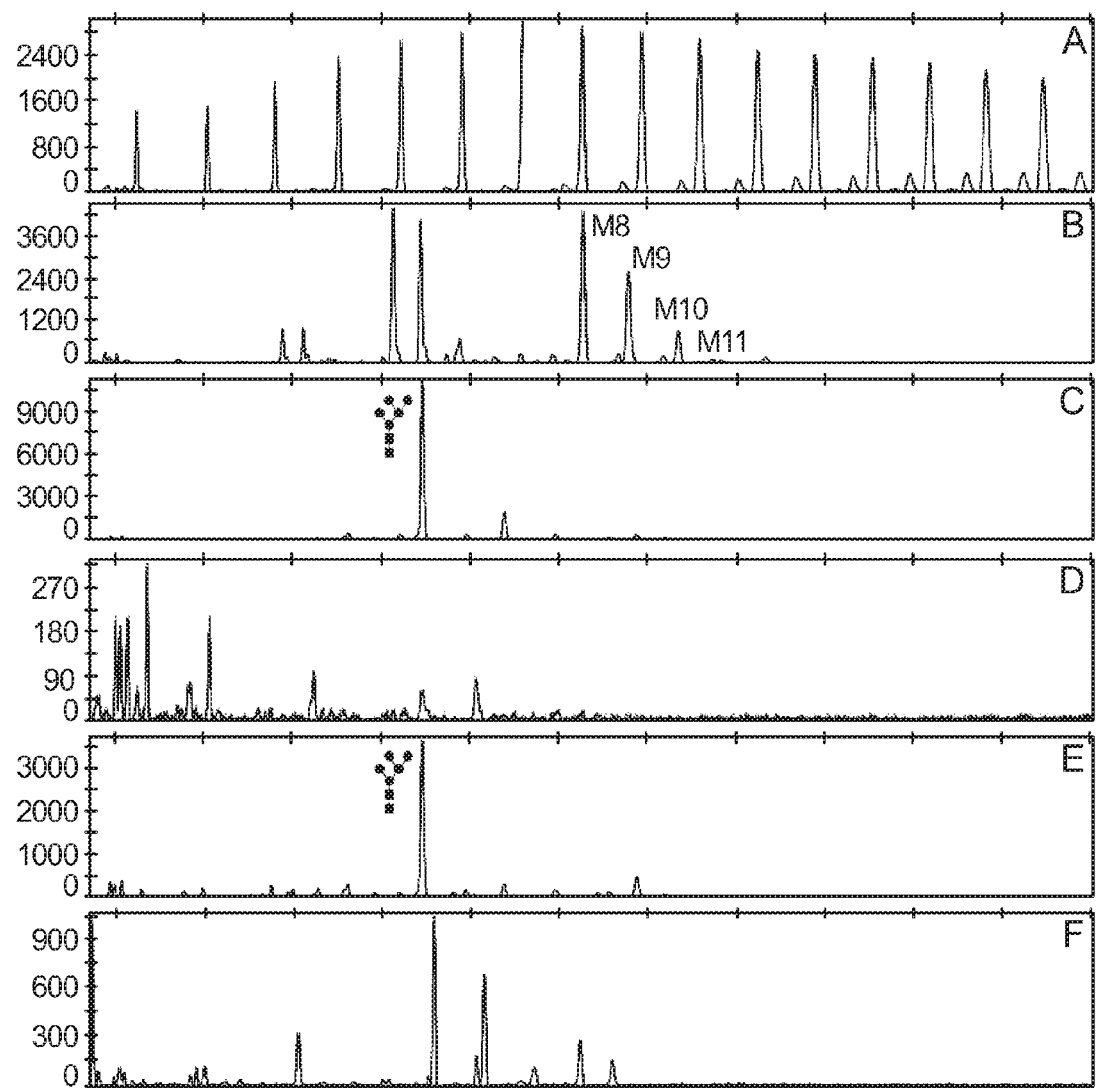
FIG. 14. DSA-FACE analysis of the total N-glycan pool on medium proteins from 'CalB' strains. A. result for a malto-dextrose reference. Panel B to F show results for N-glycans, as follows: B. GS CalB strain in microscale; C. M5 CalB strain in microscale; D. GS CalB strain in bioreactor; E. M5 CalB strain in bioreactor; F. reference N-glycans from bovine RNase B.
Figure 15:
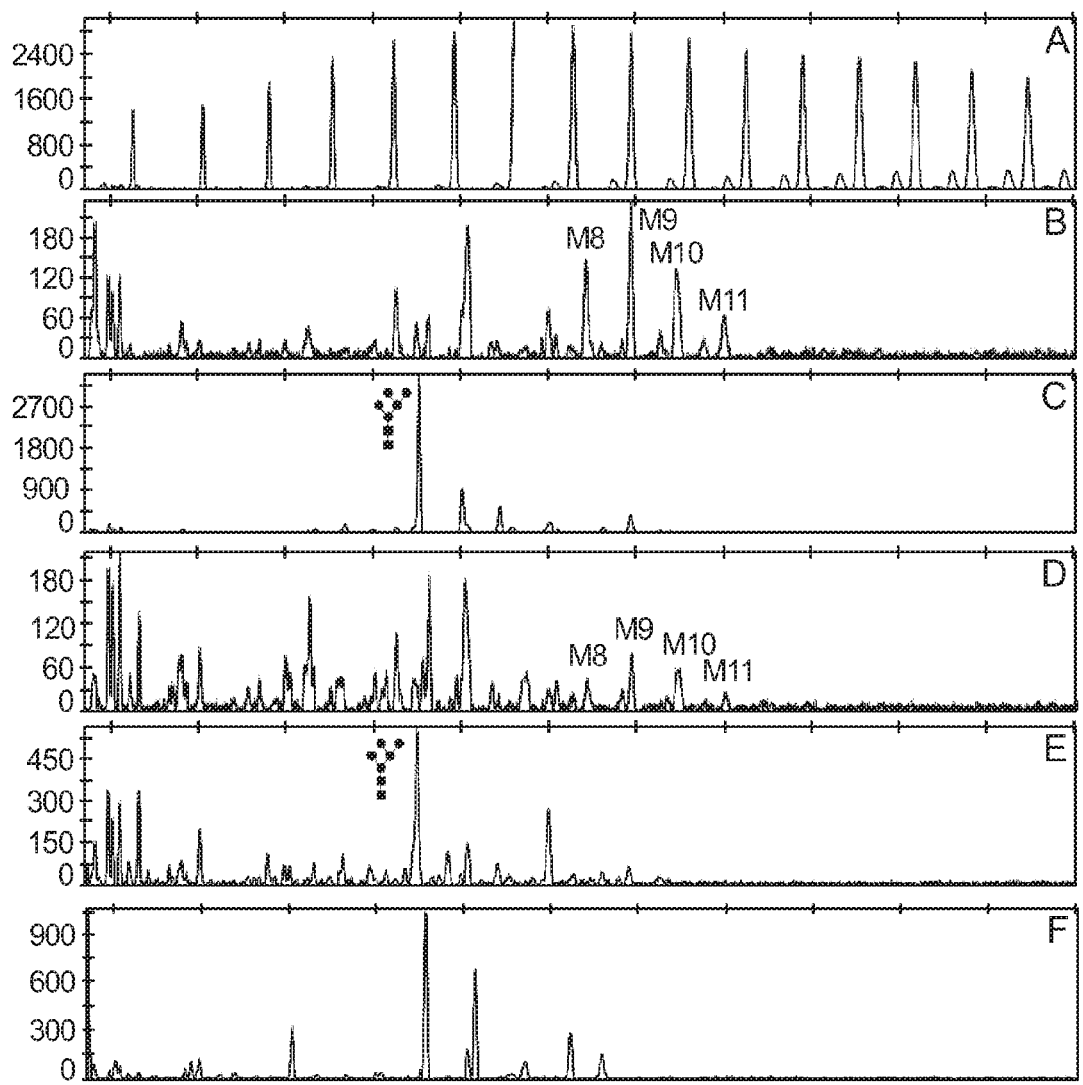
FIG. 15. DSA-FACE analysis of the total N-glycan pool on medium proteins from 'CalA' strains. A. result for a malto-dextrose reference. Panel B to F show results for N-glycans, as follows: B. GS CalA strain in microscale; C. M5 CalA strain in microscale; D. GS CalA strain in bioreactor; E. M5 CalA strain in bioreactor; F. reference N-glycans from bovine RNase B.

As shown in FIGS. 13-15, the N-glycans of proteins produced from the SuperM5 strain were substantially homogeneous, with Man5GlcNAc2 being the principal N-glycan. In contrast, the N-glycans of proteins produced from the M5-Blast were quite heterogeneous, especially from cultures in a bioreactor.

Example 9

In this Example, a diploid strain is created by mating the SuperM5 strain described in Example 1 and a wild-type *Pichia pastoris* strain of a different genetic background. The combination of the two genetic backgrounds allows a determination whether second site repressors or enhancers of the OCH1 disruption phenotype exist in either strain. The diploid is "held together" using two dominant selectable markers in identical genomic locations in each haploid strain. At the diploid OCH1 locus this strain transcribes two different mRNAs; one encoding the wild-type Och1p (from the wild-type haploid genomic copy) and the other encoding the mutant Och1p (from the SuperMan5 haploid genomic copy).

A double-crossover vector containing a Hygromycin B selection marker is constructed that replaces a highly conserved region of Och1p with a V5 epitope tag. This vector is designed so that integration into the diploid genome will, at approximately 50/50 distribution, replace the highly conserved domain in either the wild-type or mutant form of Och1p, creating both epitope insertions in the same starting genetic background. In the case where the vector integrates into the SuperM5 genomic copy of OCH1, the drug selection marker on the vector will be tightly linked to the existing Blasticidin marker adjacent to OCH1. Genomic PCR and DNA sequencing can be used to verify the construction of the two diploid strains, one with the wild-type and one with the mutant form of Och1p epitope tagged.

The diploids are sporulated and random spores grown and analyzed. After growth on non-selective medium, resulting haploid colonies are scored for Hygromycin B resistance. Distribution and growth characteristics of Hygromycin B resistance haploids can determine the lethality or growth deficiency of Och1p inactivation by epitope insertion.

Methods—An existing SuperMan5 strain with a Zeocin resistance marker at the prb1Δ locus is mated with a BG10 haploid strain with a nourseothricin resistance marker at the prb1Δ locus to create the starting diploid strain. The BG10 strain is created from a prb1Δ knockout DNA construct.

A Hygromycin B vector is constructed to replace 14 amino acids in the Och1p sequence (LFARGGLYADMDTML, SEQ ID NO: 92) with the 14 amino acid V5 epitope (GKPIPNPLLGLDST, SEQ ID NO: 93). This retains the full length coding region for both the wild-type and mutant forms of Och1p when integrated into the genome.

The Hygromycin B vector is integrated by homologous recombination into the diploid genome. PCR screening of genomic DNA can be used to verify the chromosome (either SuperMan5 or BG10) and location at which homologous recombination has occurred. PCR products from positive strains are sequenced to verify the replacement of the 14 amino acid domain from Och1p with the V5 tag, making sure the respective ORF lengths are retained in each of the two copies.

The two strains are grown and sporulated, and resultant haploids verified by sensitivity to one or the other drug marker at the prb1Δ locus. Haploids can be visually screened for growth phenotype at the plate level and, if a marked growth distribution is observed, scored for the presence of the V5 tagged construct at either or both of the SuperMan5 or BG10 och1 loci. If all haploids grow equally well, they can be scored for the presence of the Hygromycin B marker. Loss of the Hygromycin B marker on sporulation and subsequent germination will indicate that insertion of the V5 epitope into the Och1p protein is lethal in both the wild-type and mutant cases.

Detection of V5 tagged protein by Western blot in supernatants and extracts of both diploid strains, and, if viable, resultant haploids. As additional experimentation, subcellular location of the wild-type and mutant V5 tagged forms of Och1p can be performed by immunofluorescence on diploid cells.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

TABLE 1

```
                                                              SEQ ID NO: 1
   1 AACGTCAAAG ACAGCAATGG AGTCAATATT GATAACACCA CTGGCAGAGC GGTTCGTACG
  61 TCGTTTTGGA GCCGATATGA GGCTCAGCGT GCTAACAGCA CGATTGACAA GAAGACTCTC
 121 GAGTGACAGT AGGTTGAGTA AAGTATTCGC TTAGATTCCC AACCTTCGTT TTATTCTTTC
 181 GTAGACAAAG AAGCTGCATG CGAACATAGG GACAACTTTT ATAAATCCAA TTGTCAAACC
 241 AACGTAAAAC CCTCTGGCAC CATTTTCAAC ATATATTTGT GAAGCAGTAC GCAATATCGA
 301 TAAATACTCA CCGTTGTTTG TAACAGCCCC AACTTGCATA CGCCTTCTAA TGACCTCAAA
 361 TGGATAAGCC GCAGCTTG7G CTAACATACC AGCAGCACCG CCCGCGGTCA GCTGCGCCCA
 421 CACATATAAA GGCAATCTAC GATCATGGGA GGAATTAGTT TTGACCGTCA GGTCTTCAAG
 481 AGTTTTGAAC TCTTCTTCTT GAACTGTGTA ACCTTTTAAA TGACGGGATC TAAATACGTC
 541 ATGGATGAGA TCATGTGTGT AAAAACTGAC TCCAGCATAT GGAATCATTC CAAAGATTGT
 601 AGGAGCGAAC CCACGATAAA AGTTTCCCAA CCTTGCCAAA GTGTCTAATG CTGTGACTTG
 661 AAATCTGGGT TCCTCGTTGA AGACCCTGCG TACTATGCCC AAAAACTTTC CTCCACGAGC
 721 CCTATTAACT TCTCTATGAG TTTCAAATGC CAAACGGACA CGGATTAGGT CCAATGGGTA
 781 AGTGAAAAAC ACAGAGCAAA CCCCAGCTAA TGAGCCGGCC AGTAACCGTC TTGGAGCTGT
 841 TTCATAAGAG TCATTAGGGA TCAATAACGT TCTAATCTGT TCATAACATA CAAATTTTAT
 901 GGCTGCATAG GGAAAAATTC TCAACAGGGT AGCCGAATGA CCCTGATATA GACCTGCGAC
 961 ACCATCATAC CCATAGATCT GCCTGACAGC CTTAAAGAGC CCGCTAAAAG ACCCGGAAAA
1021 CCGAGAGAAC TCTGGATTAG CAGTCTGAAA AGAATCTTC ACTCTGTCTA GTGGAGCAAT
1081 TAATGTCTTA GCGGCACTTC CTGCTACTCC GCCAGCTACT CCTGAATAGA TCACATACTG
1141 CAAAGACTGC TTGTCGATGA CCTTGGGGTT ATTTAGCTTC AAGGGCAATT TTTGGGACAT
1201 TTTGGACACA GGAGACTCAG AAACAGACAC AGAGCGTTCT GAGTCCTGGT GCTCCTGACG
1261 TAGGCCTAGA ACAGGAATTA TTGGCTTTAT TTGTTTGTCC ATTTCATAGG CTTGGGGTAA
1321 TAGATAGATG ACAGAGAAAT AGAGAAGACC TAATATTTTT TGTTCATGGC AAATCGCGGG
1381 TTCGCGGTCG GGTCACACAC GGAGAAGTAA TGAGAAGAGC TGGTAATCTG GGTAAAAGG
1441 GTTCAAAAGA AGGTCGCCTG GTAGGGATGC AATACAAGGT TGTCTTGGAG TTTACATTGA
1501 CCAGATGATT TGGCTTTTTC TCTGTTCAAT TCACATTTTT CAGCGAGAAT CGGATTGACG
1561 GAGAAATGGC GGGGTGTGGG GTGGATAGAT GGCAGAAATG CTCGCAATCA CCGCGAAAGA
1621 AAGACTTTAT GGAATAGAAC TACTGGGTGG TGTAAGGATT ACATAGCTAG TCCAATGGAG
1681 TCCGTTGGAA AGGTAAGAAG AAGCTAAAAC CGGCTAAGTA ACTAGGGAAG AATGATCAGA
1741 CTTTGATTTG ATGAGGTCTG AAAATACTCT GCTGCTTTTT CAGTTGCTTT TTCCCTGCAA
1801 CCTATCATTT TCCTTTTCAT AAGCCTGCCT TTTCTGTTTT CACTTATATG AGTTCCGCCG
1861 AGACTTCCCC AAATTCTCTC CTGGAACATT CTCTATCGCT CTCCTTCCAA GTTGCGCCCC
1921 CTGGCACTGC CTAGTAATAT TACCACGCGA CTTATATTCA GTTCCAGAAT TCCAGTGTT
1981 CGTAGCAAAT ATCATCAGCC TACCGTTCGT ATAGCATACA TTATACGAAC GGTACTTTTT
2041 TGTAGAAATG TCTTGGTGTC CTCGTCCAAT CAGGTAGCCA TCTCTGAAAT ATCTGGCTCC
2101 GTTGCAACTC CGAACGACCT GCTGGCAACG TAAAATTCTC CGGGGTAAAA CTTAAATGTG
2161 GAGTAATGGA ACCAGAAACG TCTCTTCCCT TCTCTCTCCT TCCACCGCCC GTTACCGTCC
2221 CTAGGAAATT TTACTCTGCT GGAGAGCTTC TTCTACGGCC CCCTTGCAGC AATGCTCTTC
2281 CCAGCATTAC GTTGCGGGTA AAACGGAGGT CGTGTACCCG ACCTAGCAGC CCAGGGATGG
2341 AAAAGTCCCG GCCGTCGCTG GCAATAATAG CGGGCGGACG CATGTCATGA GATTATTGGA
```

TABLE 1-continued

```
2401 AACCACCAGA ATCGAATATA AAAGGCGAAC ACCTTTCCCA ATTTTGGTTT CTCCTGACCC
2461 AAAGACTTTA AATTTAATTT ATTTGTCCCT A7TTCAATCA ATTGAACAAC TATTTCGCGA
2521 AACGATGAGA TTTCCTTCAA TTTTTACTGC TGTTTTATTC GCAGCATCCT CCGCATTAGC
2581 TGCTCCAGTC AACACTACAA CAGAAGATGA AACGGCACAA ATTCCGGCTG AAGCTGTCAT
2641 CGGTTACTCA GATTTAGAAG GGGATTTCGA TGTTGCTGTT TTGCCATTTT CCAACAGCAC
2701 AAATAACGGG TTATTGTTTA TAAATACTAC TATTGCCAGC ATTGCTGCTA AAGAAGAAGG
2761 GGTATCTCTC GAGAAAAGAG AGGCTGAAGC TGAATTCGCC ACAAAACGTG GATCTCCCAA
2821 CCCTACGAGG GCGGCAGCAG TCAAGGCCGC ATTCCAGACG TCGTGGAACG CTTACCACCA
2381 TTTTGCCTTT CCCCATGACG ACCTCCACCC GGTCAGCAAC AGCTTTGATG ATGAGAGAAA
2941 CGGCTGGGGC TCGTCGGCAA TCGATGGCTT GGACACGGCT ATCCTCATGG GGATGCCGA
3001 CATTGTGAAC ACGATCCTTC AGTATGTACC GCAGATCAAC TTCACCACGA CTGCGGTTGC
3061 CAACCAAGGC ATCTCCGTGT TCGAGACCAA CATTCGGTAC CTCGGTGGCC TGCTTTCTGC
3121 CTATGACCTG TTGCGAGGTC CTTTCAGCTC CTTGGCGACA AACCAGACCC TGGTAAACAG
3181 CCTTCTGAGG CAGGCTCAAA CACTGGCCAA CGGCCTCAAG GTTGCGTTCA CCACTCCCAG
3241 CGGTGTCCCG GACCCTACCG TCTTCTTCAA CCCTACTGTC GGAGAAGTG GTGCATCTAG
3301 CAACAACGTC GCTGAAATTG GAAGCCTGGT GCTCGAGTGG ACACGGTTGA GCGACCTGAC
3361 GGGAAACCCG CAGTATGCCC AGCTTGCGCA GAAGGGCGAG TCGTATCTCC TGAATCCAAA
3421 GGGAAGCCCG GAGGCATGGC CTGGCCTGAT TGGAACGTTT GTCAGCACGA GCAACGGTAC
3481 CTTTCAGGAT AGCAGCGGCA GCTGGTCCGG CCTCATGGAC AGCTTCTACG AGTACCTGAT
3541 CAAGATGTAC CTGTACGACC CGGTTGCGTT TGCACACTAC AAGGATCGCT GGGTCCTTGC
3601 TGCCGACTCG ACCATTGCGC ATCTCGCCTC TCACCCGTCG ACGCGCAAGG ACTTGACCTT
3661 TTTGTCTTCG TACAACGGAC AGTCTACGTC GCCAAACTCA GGACATTTGG CCAGTTTTGC
3721 CGGTGGCAAC TTCATCTTGG GAGGCATTCT CCTGAACGAG CAAAAGTACA TTGACTTTGG
3781 AATCAAGCTT GCCAGCTCGT ACTTTGCCAC GTACAACCAG ACGGCTTCTG GAATCGGCCC
3841 CGAAGGCTTC GCGTGGGTGG ACAGCGTGAC GGGCGCCGGC GGCTCGCCGC CCTCGTCCCA
3901 GTCCGGGTTC TACTCGTCGG CAGGATTCTG GGTGACGGCA CCGTATTACA TCCTGCGGCC
3961 GGAGACGCTG GAGAGCTTGT ACTACGCATA CCGCGTCACG GGCGACTCCA AGTGGCAGGA
4021 CCTGGCGTGG GAAGCGTTCA GTGCCATTGA GGACGCATGC CGCGCCGGCA GCGCGTACTC
4081 GTCCATCAAC GACGTGACGC AGGCCAACGG CGGGGGTGCC TCTGACGATA TGGAGAGCTT
4141 CTGGTTTGCC GAGGCGCTCA AGTATGCGTA CCTGATCTTT GCGGAGGAGT CGGATGTGCA
4201 GGTGCAGGCC AACGGCGGGA ACAAATTTGT CTTTAACACG GAGGCGCACC CCTTTAGCAT
4261 CCGTTCATCA TCACGACGGG GCGGCCACCT TGCTCACGAC GAGTTGTAAT CTAGGGCGGC
4321 CGCCAGCTTG GGCCCGAACA AAAACTCATC TCAGAAGAGG ATCTGAATAG CGCCGTCGAC
4381 CATCATCATC ATCATCATTG AGTTTTAGCC TTAGACATGA CTGTTCCTCA GTTCAAGTTG
4441 GGCACTTACG AGAAGACCGG TCTTGCTAGA TTCTAATCAA GAGGATGTCA GAATGCCATT
4501 TGCCTGAGAG ATGCAGGCTT CATTTTTGAT ACTTTTTTAT TTGTAACCTA TATAGTATAG
4561 GATTTTTTTT GTCATTTTGT TTCTTCTCGT ACGAGCTTGC TCCTGATCAG CCTATCTCGC
4621 AGCTGATGAA TATCTTGTGG TAGGGGTTTG GGAAAATCAT TCGAGTTTGA TGTTTTTCTT
4681 GGTATTTCCC ACTCCTCTTC AGAGTACAGA AGATTAAGTG AGACCTTCGT TTGTGCGGAT
4741 CCCCCACACA CCATAGCTTC AAAATGTTTC TACTCCTTTT TTACTCTTCC AGATTTTCTC
```

TABLE 1-continued

```
4801 GGACTCCGCG CATCGCCGTA CCACTTCAAA ACACCCAAGC ACAGCATACT AAATTTCCCC
4861 TCTTTCTTCC TCTAGGGTGT CGTTAATTAC CCGTACTAAA GGTTTGGAAA AGAAAAAAGA
4921 GACCGCCTCG TTTCTTTTTC TTCGTCGAAA AAGGCAATAA AAATTTTTAT CACGTTTCTT
4981 TTTCTTGAAA ATTTTTTTTT TTGATTTTTT TCTCTTTCGA TGACCTCCCA TTGATATTTA
5041 AGTTAATAAA CGGTCTTCAA TTTCTCAAGT TTCAGTTTCA TTTTTCTTGT TCTATTACAA
5101 CTTTTTTTAC TTCTTGCTCA TTAGAAAGAA AGCATAGCAA TCTAATCTAA GGGCGGTGTT
5161 GACAATTAAT CATCGGCATA GTATATCGGC ATAGTATAAT ACGACAAGGT GAGGAACTAA
5221 ACCATGGCCA AGCCTTTGTC TCAAGAAGAA TCCACCCTCA TTGAAAGAGC AACGGCTACA
5281 ATCAACAGCA TCCCCATCTC TGAAGACTAC AGCGTCGCCA GCGCAGCTCT CTCTAGCGAC
5341 GGCCGCATCT TCACTGGTGT CAATGTATAT CATTTTACTG GGGGACCTTG TGCAGAACTC
5401 GTGGTGCTGG GCACTGCTGC TGCTGCGGCA GCTGGCAACC TGACTTGTAT CGTCGCGATC
5461 GGAAATGAGA ACAGGGGCAT CTTGAGCCCC TGCGGACGGT GCCGACAGGT GCTTCTCGAT
5521 CTGCATCCTG GGATCAAAGC CATAGTGAAG ACAGTGATG GACAGCCGAC GGCAGTTGGG
5581 ATTCGTGAAT TGCTGCCCTC TGGTTATGTG TGGGAGGGCT AAGCACTTCG TGGCCGAGGA
5641 GCAGGACTGA CACGTCCGAC GCGGCCCGAC GGGTCCGAGG CCTCGGAGAT CCGTCCCCCT
5701 TTTCCTTTGT CGATATCATG TAATTAGTTA TGTCACGCTT ACATTCACGC CCTCCCCCCA
5761 CATCCGCTCT AACCGAAAAG GAAGGAGTTA GACAACCTGA AGTCTAGGTC CCTATTTATT
5321 TTTTTATAGT TATGTTAGTA TTAAGAACGT TATTTATATT TCAAATTTTT CTTTTTTTTC
5881 TGTACAGACG CGTGTACGCA TGTAACATTA TACTGAAAAC CTTGCTTGAG AAGGTTTTGG
5941 GACGCTCGAA GGCTTTAATT TGCAAGCTGG AGACCAACAT GTGAGCAAAA GGCCAGCAAA
6001 AGGCCAGGAA CCGTAAAAAG GCCGCGTTGC TGGCGTTTTT CCATAGGCTC CGCCCCCCTG
6061 ACGAGCATCA CAAAAATCGA CGCTCAAGTC AGAGGTGGCG AAACCCGACA GGACTATAAA
6121 GATACCAGGC GTTTCCCCCT GGAAGCTCCC TCGTGCGCTC TCCTGTTCCG ACCCTGCCGC
6181 TTACCGGATA CCTGTCCGCC TTTCTCCCTT CGGGAAGCGT GGCGCTTTCT CATAGCTCAC
6241 GCTGTAGGTA TCTCAGTTCG GTGTAGGTCG TTCGCTCCAA GCTGGGCTGT GTGCACGAAC
6301 CCCCCGTTCA GCCCGACCGC TGCGCCTTAT CCGGTAACTA TCGTCTTGAG TCCAACCCGG
6361 TAAGACACGA CTTATCGCCA CTGGCAGCAG CCACTGGTAA CAGGATTAGC AGAGCGAGGT
6421 ATGTAGGCGG TGCTACAGAG TTCTTGAAGT GGTGGCCTAA CTACGGCTAC ACTAGAAGAA
6481 CAGTATTTGG TATCTGCGCT CTGCTGAAGC CAGTTACCTT CGGAAAAAGA GTTGGTAGCT
6541 CTTGATCCGG CAAACAAACC ACCGCTGGTA GCGGTGGTTT TTTGTTTGC AAGCAGCAGA
6601 TTACGCGCAG AAAAAAAGGA TCTCAAGAAG ATCCTTTGAT CTTTTCTACG GGTCTGACG
6661 CTCAGTGGAA CGAAAACTCA CGTTAAGGGA TTTTGGTCAT GAGATCAGAT CTAACATCCA
6721 TAATCGTATT CGCCGTTTCT GTCATTTGCG TTTTGTACGG ACCCTCACAA CAATTATCAT
6781 CTCCAAAAAT AGACTATGAT CCATTGACGC TCCGATCACT TGATTTGAAG ACTTTGGAAG
6841 CTCCTTCACA GTTGAGTCCA GGCACCGTAG AAGATAATCT TCGAAGACAA TTGGAGTTTC
6901 ATTTTCCTTA CCGCAGTTAC GAACCTTTTC CCCAACATAT TTGGCAAACG TGGAAAGTTT
6961 CTCCCTCTGA TAGTTCCTTT CCGAAAAACT TCAAAGACTT AGGTGAAAGT TGGCTGCAAA
7021 GGTCCCCAAA TTATGATCAT TTTGTGATAC CCGATGATGC AGCATGGGAA CTTATTCACC
7081 ATGAATACGA ACGTGTACCA GAAGTCTTGG AAGCTTCCA CCTGCTACCA GAGCCCATTC
7141 TAAAGGCCGA TTTTTTCAGG TATTTGATTC TTTTTGCCCG TGGAGGACTG TATGCTGACA
```

TABLE 1-continued

```
7201 TGGACACTAT GTTATTAAAA CCAATAGAAT CGTGGCTGAC TTTCAATGAA ACTATTGGTG
7261 GAGTAAAAAA CAATGCTGGG TTGGTCATTG GTATTGAGGC TGATCCTGAT AGACCTGATT
7321 GGCACGACTG GTATGCTAGA AGGATACAAT TTTGCCAATG GGCAATTCAG TCCAAACGAG
7381 GACACCCAGC ACTGCGTGAA CTGATTGTAA GAGTTGTCAG CACGACTTTA CGGAAAGAGA
7441 AAAGCGGTTA CTTGAACATG GTGGAAGGAA AGGATCGTGG AAGTGATGTG ATGGACTGGA
7501 CGGGTCCAGG AATATTTACA GACACTCTAT TTGATTATAT GACTAATGTC AATACAACAG
7561 GCCACTCAGG CCAAGGAATT GGAGCTGGCT CAGCGTATTA CAATGCCTTA TCGTTGGAAG
7621 AACGTGATGC CCTCTCTGCC CGCCCGAACG GAGAGATGTT AAAAGAGAAA GTCCCAGGTA
7681 AATATGCACA GCAGGTTGTT TTATGGGAAC AATTTACCAA CCTGCGCTCC CCCAAATTAA
7741 TCGACGATAT TCTTATTCTT CCGATCACCA GCTTCAGTCC AGGGATTGGC CACAGTGGAG
7801 CTGGAGATTT GAACCATCAC CTTGCATATA TTAGGCATAC ATTTGAAGGA AGTTGGAAGG
7861 ACTAAAGAAA GCTAGAGTAA AATAGATATA GCGAGATTAG AGAATGAATA CCTTCTTCTA
7921 AGCGATCGTC CGTCATCATA GAATATCATG GACTGTATAG TTTTTTTTTT GTACATATAA
7981 TGATTAAACG GTCATCCAAC ATCTCGTTGA CAGATCTCTC AGTACGCGAA ATCCCTGACT
8041 ATCAAAGCAA GAACCGATGA AGAAAAAAAC AACAGTAACC CAAACACCAC AACAAACACT
8101 TTATCTTCTC CCCCCCAACA CCAATCATCA AAGAGATGTC GGAACCAAAC ACCAAGAAGC
8161 AAAAACTAAC CCCATATAAA AACATCCTGG TAGATAATGC TGGTAACCCG CTCTCCTTCC
8221 ATATTCTGGG CTACTTCACG AAGTCTGACC GGTCTCAGTT GATCAACATG ATCCTCGAAA
8281 TGGGTGGCAA GATCGTTCCA GACCTGCCTC CTCTGGTAGA TGGAGTGTTG TTTTTGACAG
8341 GGGATTACAA GTCTATTGAT GAAGATACCC TAAAGCAACT GGGGGACGTT CCAATATACA
8401 GAGACTCCTT CATCTAGCAG TGTTTTGTGC ACAAGACATC TCTTCCCATT GACACTTTCC
8461 GAATTGACAA GAACGTCGAC TTGGCTCAAG ATTTGATCAA TAGGGCCCTT CAAGAGTCTG
8521 TGGATCATGT CACTTCTGCC AGCACAGCTG CAGCTGCTGC TGTTGTTGTC GCTACCAACG
8581 GCCTGTCTTC TAAACCAGAC GCTCGTACTA GCAAAATACA GTTCACTCCC GAAGAAGATC
8641 GTTTTATTCT TGACTTTGTT AGGAGAAATC CTAAACGAAG AAACACACAT CAACTGTACA
8701 CTGAGCTCGC TCAGCACATG AAAAACCATA CGAATCATTC TATCCGCCAC AGATTTCGTC
8761 GTAATCTTTC CGCTCAACTT GATTGGGTTT ATGATATCGA TCCATTGACC AACCAACCTC
8821 GAAAAGATGA AAACGGGAAC TACATCAAGG TACAAGATCT TCCACAAGGA ATTCGTGGTC
8881 ATTATTCTGC CCAAGATGAT TACAATTTGT GTTTATCGGT TCAACCTTTC ATTGAATCTG
8941 TAGATGAGAC AACAGGCCAA GAATTTTTCA AACCTCTGAA AGGTGTATTT GATGACTTGG
9001 AATCTCGCTT TCCTCACCAT ACAAAGACTT CCTGGAGAGA CAGATTCAGA AAGTTTGCCT
9061 CTAAATACGG TGTTCGTCAG TACATCGCGT ATTATGAAAA GACTGTTGAA CTCAATGGTG
9121 TTCCTAATCC GATGACGAAC TTTACCTCAA AGGCTTCCAT TGAAAAATTT AGAGAAAGAC
9181 GCGGGACTTC ACGTAACAGT GGCCTTCCAG GCCCGGTTGG TGTAGAAGCT GTAAGCTCTT
9241 TGGACCACAT ATCCCCATTG GTCACATCTA ATTCCAATTC TGCAGCTGCT GCAGCTGCTG
9301 CCGCAGCAGT TGCAGCCTCT GCCTCTGCTT CTTCAGCTCC TAATACTTCA ACTACCAA7T
9361 TCTTTGAACA GGAGAATATT GCCCAAGTTC TCTCTGCACA TAACAACGAG CAGTCTATTG
9421 CAGAAGTTAT TGAGTCCGCA CAGAATGTCA ACACCCATGA AAGTGAACCT ATAGCTGATC
9481 ATGTTCGAAA AAATCTTACA GACGATGAAT TGCTTGACAA AATGGATGAT ATTTTAAGCT
9541 CCAGAAGTCT AGGCGGACTA GATGACTTGA TAAAGATCCT CTAGACTGAG CTGGGATTTG
```

TABLE 1-continued

```
9601 CTCATCGTTA TACCGAATTT CTTTTTACCT CATGTTCTGG TGATGTGATT TTCTTCCGAC
9661 CATTAGTGGA ACATTTCCTT CTTACTGGTG AGTGGGAGCT GGAGAATACT CGTGGCA7CT
9721 GGACCGGTCG TCAAGACGAA ATGCTACGTG CTAGCAATCT AGATGACCTG CACAAGTTAA
9781 TTGACCTGCA TGGGAAAGAA CGTGTTGAGA CCAGAAGAAA AGCCATCAAG GGAGAATGAT
9841 CATAAGAAAT GAAAAACGTA TAAGT.
```

TABLE 2

SEQ ID NO: 2

(M)AKADGSLLY YNPHNPPRRY YFYMAIFAVS VICVLYGPSQ
QLSSPKIDYD PLTLRSLDLK TLEAPSQLSP GTVEDNLRRQ
LEFHFPYRSY EPFPQHIWQT WKVSPSDSSF PKNFKDLGES
WLQRSPNYDH FVIPDDAAWE LIHHEYERVP EVLEAFHLLP
EPILKADFFR YLILFARGGL YADMDTMLLK PIESWLTFNE
TIGGVKNNAG LVIGIEADPD RPDWHDWYAR RIQFCQWAIQ
SKRGHPALRE LIVRVVSTTL RKEKSGYLNM VEGKDRGSDV
MDWTGPGIFT DTLFDYMTNV NTTGHSGQGI GAGSAYYNAL
SLEERDALSA RPNGEMLKEK VPGKYAQQVV LWEQFTNLRS
PKLIDDILIL PITSFSPGIG HSGAGDLNHH LAYIRHTFEG
SWKD.

TABLE 3

| Nucleotides deleted from Upstream OCH1 | Amino acids corresponding to deleted nucleotides | Description |
|---|---|---|
| GCG AAG GCA GAT GGC (SEQ ID NO: 29) | AKADG (SEQ ID NO: 4) | 5 AAs deleted from Upstream OCH1 portion |
| GCG AAG GCA GAT GGC AGT (SEQ ID NO: 30) | AKADGS (SEQ ID NO: 5) | 6 AAs deleted from Upstream OCH1 portion |
| GCG AAG GCA GAT GGC AGT TTG (SEQ ID NO: 31) | AKADGSL (SEQ ID NO: 6) | 7 AAs deleted from Upstream OCH1 portion |
| GCG AAG GCA GAT GGC AGT TTG CTC (SEQ ID NO: 32) | AKADGSLL (SEQ ID NO: 7) | 8 AAs deleted from Upstream OCH1 portion |
| GCG AAG GCA GAT GGC AGT TTG CTC TAC (SEQ ID NO: 33) | AKADGSLLY (SEQ ID NO: 8) | 9 AAs deleted from Upstream OCH1 portion |
| GCG AAG GCA GAT GGC AGT TTG CTC TAC TAT (SEQ ID NO: 34) | AKADGSLLYY (SEQ ID NO: 9) | 10 AAs deleted from Upstream OCH1 portion |
| ATG GCG AAG GCA GAT GGC (SEQ ID NO: 35) | MAKADG (SEQ ID NO: 10) | 6 AAs deleted from Upstream OCH1 portion |
| ATG GCG AAG GCA GAT GGC AGT (SEQ ID NO: 36) | MAKADGS (SEQ ID NO: 11) | 7 AAs deleted from Upstream OCH1 portion |
| ATG GCG AAG GCA GAT GGC AGT TTG (SEQ ID NO: 37) | MAKADGSL (SEQ ID NO: 12) | 8 AAs deleted from Upstream OCH1 portion |
| ATG GCG AAG GCA GAT GGC AGT TTG CTC (SEQ ID NO: 38) | MAKADGSLL (SEQ ID NO: 13) | 9 AAs deleted from Upstream OCH1 portion |
| ATG GCG AAG GCA GAT GGC AGT TTG CTC TAC (SEQ ID NO: 39) | MAKADGSLLY (SEQ ID NO: 14) | 10 AAs deleted from Upstream OCH1 portion |
| ATG GCG AAG GCA GAT GGC AGT TTG CTC TAC TAT (SEQ ID No: 40) | MAKADGSLLYY (SEQ ID NO: 15) | 11 AAs deleted from Upstream OCH1 portion |
| ATG GCG AAG GCA GAT GGC AGT TTG CTC TAC TAT AAT (SEQ ID NO: 41) | MAKADGSLLYYN (SEQ ID NO: 16) | 12 AAs deleted from Upstream OCH1 portion |
| ATG GCG AAG GCA GAT GGC AGT TTG CTC TAC TAT AAT CCT (SEQ ID NO: 42) | MAKADGSLLYYNP (SEQ ID NO: 17) | 13 AAs deleted from Upstream OCH1 portion |
| ATG GCG AAG GCA GAT GGC AGT TTG CTC TAC TAT AAT CCT CAC (SEQ ID NO: 43) | MAKADGSLLYYNPH (SEQ ID NO: 18) | 14 AAs deleted from Upstream OCH1 portion |
| ATG GCG AAG GCA GAT GGC AGT TTG CTC TAC TAT AAT CCT CAC AAT (SEQ ID NO: 44) | MAKADGSLLYYNPHN (SEQ ID NO: 19) | 15 AAs deleted from Upstream OCH1 portion |
| ATG GCG AAG GCA GAT GGC AGT TTG CTC TAC TAT AAT CCT CAC AAT CCA (SEQ ID NO: 45) | MAKADGSLLYYNPHNP (SEQ ID NO: 20) | 16 AAs deleted from Upstream OCH1 portion |
| ATG GCG AAG GCA GAT GGC AGT TTG CTC TAC TAT AAT CCT CAC AAT CCA CCC (SEQ ID NO: 46) | MAKADGSLLYYNPHNP P (SEQ ID NO: 21) | 17 AAs deleted from Upstream OCH1 portion |
| ATG GCG AAG GCA GAT GGC AGT TTG CTC TAC TAT AAT CCT CAC AAT CCA CCC AGA (SEQ ID NO: 47) | MAKADGSLLYYNPHNP PR (SEQ ID NO: 22) | 18 AAs deleted from Upstream OCH1 portion |

TABLE 3-continued

| Nucleotides deleted from Upstream OCH1 | Amino acids corresponding to deleted nucleotides | Description |
|---|---|---|
| ATG GCG AAG GCA GAT GGC AGT TTG CTC TAC TAT AAT CCT CAC AAT CCA CCC AGA AGG (SEQ ID NO: 48) | MAKADGSLLYYNPHNP PRR (SEQ ID NO: 23) | 19 AAs deleted from Upstream OCH1 portion |
| ATG GCG AAG GCA GAT GGC AGT TTG CTC TAC TAT AAT CCT CAC AAT CCA CCC AGA AGG TAT (SEQ ID NO: 49) | MAKADGSLLYYNPHNP PRRY (SEQ ID NO: 24) | 20 AAs deleted from Upstream OCH1 portion |
| ATG GCG AAG GCA GAT GGC AGT TTG CTC TAC TAT AAT CCT CAC AAT CCA CCC AGA AGG TAT TAC (SEQ ID NO: 50) | MAKADGSLLYYNPHNP PRRYY (SEQ ID NO: 25) | 21 AAs deleted from Upstream OCH1 portion |
| GCG AAG GCA GAT GGC AGT TTG CTC TAC TAT AAT CCT CACA ATC CAC CCA GAA GGT ATT ACT TCT ACA TGG CTA (SEQ ID NO: 51) | AKADGSLLYYNPHNPP RRYYFYMA (SEQ ID NO: 26) | 24 AAs deleted from Upstream OCH1 portion |
| ATG GCG AAG GCA GAT GGC AGT TTG CTC TAC TAT AAT CCT CACA ATC CAC CCA GAA GGT ATT ACT TCT ACA TGG CIA (SEQ ID NO: 52) | MAKADGSLLYYNPHNP PRRYYFYMA (SEQ ID NO: 27) | 25 AAs deleted from Upstream OCH1 portion |

TABLE 4

SEQ ID NO: 53

```
   1 AACGTCAAAG ACAGCAATGG AGTCAATATT GATAACACCA CTGGCAGAGC GGTTCGTACG
  61 TCGTTTTGGA GCCGATATGA GGCTCAGCGT GCTAACAGCA CGATTGACAA GAAGACTCTC
 121 GAGTGACAGT AGGTTGAGTA AAGTATTCGC TTAGATTCCC AACCTTCGTT TTATTCTTTC
 181 GTAGACAAAG AAGCTGCATG CGAACATAGG GACAACTTTT ATAAATCCAA TTGTCAAACC
 241 AACGTAAAAC CCTCTGGCAC CATTTTCAAC ATATATTTGT GAAGCAGTAC GCAAATATCGA
 301 TAAATACTCA CCGTTGTTTG TAACAGCCCC AACTTGCATA CGCCTTCTAA TGACCTCAAA
 361 TGGATAAGCC GCAGCTTGTG CTAACATACC AGCAGCACCG CCCGCGGTCA GCTGCGCCCA
 421 CACATATAAA GGCAATCTAC GATCATGGGA GGAATTAGTT TTGACCGTCA GGTCTTCAAG
 481 ACTTTTGAAC TCTTCTTCTT GAACTGTGTA ACCTTTTAAA TGACGGGATC TAAATACGTC
 541 ATGGATGAGA TCATGTGTGT AAAAACTGAC TCCAGCATAT GGAATCATTC CAAAGATTGT
 601 AGGAGCGAAC CCACGATAAA AGTTTCCCAA CCTTGCCAAA GTGTCTAATG CTGTGACTTG
 661 AAATCTGCGT TCCTCGTTGA AGACCCTGCG TACTATGCCC AAAAACTTTC CTCCACGAGC
 721 CCTATTAACT TCTCTATGAG TTTCAAATGC CAAACGGACA CGGATTAGGT CCAATGGGTA
 781 AGTGAAAAAC ACAGACCAAA CCCCAGCTAA TGAGCCGGCC AGTAACCGTC TTGGAGCTGT
 841 TCATAAGAG TCATTAGGGA TCAATAACGT TCTAATCTGT TCATAACATA CAAATTTTAT
 901 GGCTGCATAG GGAAAAATTC TCAACAGGGT AGCCGAATGA CCGTGATATA GACCTGCGAC
 951 ACCATCATAC CCATACATCT GCCTGACAGC CTTAAAGAGC CCGCTAAAAG ACCCGGAAAA
1021 CCGAGAGAAC TCTGGATTAG GAGTCTGAAA AGAATCTTC ACTCTGTCTA GTGGAGCAAT
1081 TAATGTCTTA GCGGCACTTC CTGCTACTCC GCCAGCTACT CCTGAATAGA TCACATACTG
1141 CAAAGACTGC TTGTCGATGA CCTTGGGGTT ATTTAGCTTC AAGGGCAATT TTTGGGACAT
1201 TTTGGACACA GGAGACTCAG AAACAGACAC AGAGCGTTCT GAGTCCTGGT GCTCCTGACG
1261 TAGGCCTAGA ACAGGAATTA TTCGCTTTAT TTGTTTGTCC ATTTCATAGG CTTGGGGTAA
1321 TAGATAGATG ACAGACAAAT AGAGAAGACC TAATATTTTT TGTTCATGGC AAATCGCGGG
1381 TTCGCGGTCG GGTCACACAC GGAGAAGTAA TGAGAAGAGC TGGTAATCTG GGGTAAAAGG
1441 GTTCAAAAGA AGGTCGCCTG GTAGGGATGC AATACAAGGT TGTCTTGGAG TTTACATTGA
```

TABLE 4-continued

```
1501 CCAGATCATT TGGCTTTTTC TCTGTTCAAT TCACATTTTT CAGCGAGAAT CGGATTGACG
1561 GAGAAATGGC GGGGTGTGGG GTGGATAGAT GGCAGAAATG CTCGCAATCA CCGCGAAAGA
1621 AAGACTTTAT GGAATAGAAC TACTGGGTGG TGTAAGGATT ACATAGCTNG TCCAATGGAG
1681 TCCGTTGGAA AGGTAAGAAG AAGCTAAAAC CGGCTAAGTA ACTAGGGAAG AATGATCAGA
1741 CTTTGATTTG ATGAGGTCTG AAAATACTCT GCTGCTTTTT CAGTTGCTTT TTCCCTGCAA
1801 CCTATCATTT TCCTTTTCAT AAGCCTGCCT TTTCTGTTTT CACTTATATG AGTTCCGCCG
1861 AGACTTCCCC AAATTCTCTC CTGGAACATT CTCTATCGCT CTCCTTCCAA GTTGCGCCCC
1921 CTGGCACTGC CTAGTAATAT TACCACGCGA CTTATATTCA GTTCCACAAT TTCCAGTGTT
1981 CGTAGCAAAT ATCATCAGCC ATGGCGAAGG CAGATGGCAG TTTGCTCTAC TATAATCCTC
2041 ACAATCCACC CAGAAGGTAT TACTTCTACA TGGCTATATT CGCCGTTTCT GTCATTTGCG
2101 TTTTGTACGG ACCCTCACAA CAATTATCAT CTCCAAAAAT AGACTATGAT CCATTGACGC
2161 TCCGATCACT TGATTTGAAG ACTTTGGAAG CTCCTTCACA GTTGAGTCCA GGCACCGTAG
2221 AAGATAATCT TCGaagacaa ttagagtttc attttcctta ccgcagttac gaaccttttc
2281 cccaacatat ttggcaaacg tggaaagttt ctccctctga tagttccttt ccaaaaaact
2341 tcaaagactt aagtgaaagt tggctgcaaa ggtccccaaa ttatgatcat tttgtgatac
2401 ccgatgatgc agcatgggaa cttattcacc atgaatagaa acgtgtacca gaagtcttgg
2461 aagctctaga tgctcaccgc aatgctgtta aggttcgtat ggagaaactg ggacttattt
2521 aattatttag agattttaac ttacatttag attcgataga tccacaggac gggtgtggtc
2581 gccatgatcg cgtagtcgat agtggctcca agtagcgaag cgaacaggac tgggcggcgg
2641 ccaaagcggt cggacagtgc tccgagaacg ggtgcgcata gaaattgcat caacgcatat
2701 ggcgctaaca gcacgccata gtgactggcg atactatcgg aatggacgat atcccgcaag
2761 aggcccggca gtaccggcat aaccaagcct atgcctacag catccagggt gacggtgccg
2821 aggatgacga tgagcgcatt gttagatttc atacacggtg cctgactgcg ttagcaattt
2881 aactgtgata aactaccgca ttaaagctga tctttttgt agaaatgtct tggtgtcctc
2941 gtccaatcag gtagccatct ctgaaatatc tggctccgtt gcaactccga acgacctgct
3001 ggcaacgtaa aattctccgg ggtaaaactt aaatgtggag taatggaacc agaaacgtct
3061 cttccctcct ctctccttcc accgcccgtt accgtcccta ggaaatttta ctctgctgga
3121 gagcttcttc tacggccccc ttgcagcaat gctcttccca gcattacgtt gcgggtaaaa
3181 cggaggtcgt gtacccgacc tagcagcccg gggatggaaa agtcccggcc gtcgctggca
3241 ataatagcgg gcggacgcgt gtcatgagat tattggaaac caccagaatc gaatataaaa
3301 ggcgaacacc tttcccaatt ttgatttctc ctgacccana gactttaaat ttaatttatt
3361 tgtccctatt tcaatcaatt gaacaactat ttcgcgaaac gatgagattt ccttcaattt
3421 ttactgctgt tttattcaca gcatcctccg cattgactgc tccagtcaac actacaacag
3481 aagatgaaac ggcacaaatt ccggctgaag ctgtcatcgg ttatcaggat ttagaagggg
3541 atttcgatgt tgctgttttg ccatttccca acagcacaaa taacgggtta ttgtttataa
3601 atactactat tgccagcatt gctgctaaag aagaaggggt atctctcgag aaaagagagg
3661 ctgaagctga attcgccaca agacgtggat ctcccaaccc tacgagggcg cagcagtca
3721 aggccgcatt ccagacgtcg tggaacgctt accaccattt tgcctttccc catgacgacc
3781 tccacccggt cagcaacagc tttgatgatg agagaaccgg ctggagctcg tcggcaatcg
3841 atggcttgga cacagctatc ctcatggggg atgccgacat tgtgaacacg atccttcagt
```

TABLE 4-continued

```
3901 atataccgca gatcaacttc accacgactg cggttgccca ccaaggatcc tccatgttcg
3961 agaccaacat tcggtacctc ggtggcctgc tttctaccta tgacctgttg cgaggtcctt
4021 tcggctcctt ggcgacaaac cagaccctgg taaacagcct tctgaggcag gctcaaacac
4081 tggccaacgg cctcaaggtt gcgttcacca ctcccagcgg tgtcccggac cctaccgtct
4141 tcttcaaccc tactgtccgg agaagtggtg catctagcag caacgtcgct gaaattggaa
4201 gcctggtact cgggtggaca cggttgagcg acctgacagg aaacccgcag tgtacccagc
4261 ttgcgcagaa gggcgagtcg tatctcctga atccgaaggg aagcccggag gcatggcctg
4321 gcctaattgg gacatttatc agcacgagca acggtacctt tcaggatagc agcagcagct
4381 ggtccggcct catggacagc ttctacgagt acctgatcaa gatgtacctg tacgacccgg
4441 ttgcgtttgc acgctacaag gatcgctggg tccttggtgc cgactcgacc attgggcatc
4501 tcggctctca cccatcgacg cgcgaggact tgacctttt gtcttcgtac aacggacagt
4561 ctacgtcacc aaactcagga catttggcca gttttggcag tggcaacttc atcttgggag
4621 gcattctcct gaacgagcaa aagtacattg actttggaat caggcttgcc agctcgtact
4681 ttggcacgta cacccagacg gcttctggaa tcggccccga aggcttcgcg tggatgaaca
4741 gcgtgacgag cgccggcggc tcgccgccct cgtcccagtc cgggttctac tcgtcggcag
4801 gattctgggt gacgacaccg tattacatcc tgcgtccgga gacgctggag agcttgtact
4861 acgcataccg cgtcacgggc gactccaagt ggcaggacct ggcgtgggaa gcgttgagtg
4921 ccattgagga cgcataccgc gccggcagcg cgtactcgtc catcaacgac gtgacgcagg
4981 ccaacggcgg gggtgcctct gacgatatgg agagcttctg gtttgccgag gcgctcaagt
5041 atgcgtacct gatctttgcg gaggagtcgg atgtgcaggt gcaggccacc ggcgggaaca
5101 aatttgtctt tgacacggag gcgcaccect ttagcatccg ttcatcatca cgacggggcg
5161 gccaccttgc tcacgacgag ttgtaatcta gggcGGCCGC CAGCTTGGGC CCGAACAAAA
5221 ACTCATCTCA GAAGAGGATC TGAATAGCGC CGTCGACCAT CATCATCATC ATCATTGAGT
5281 TTTAGCCTTA GACATGACTG TTCCTCAGTT CAAGTTGGGC ACTTACGAGA AGACCGGTCT
5341 TGCTAGATTC TAATCAAGAG GATGTCAGAA TGCCATTTGC CTGAGAGATG CAGGCTTCAT
5401 TTTTGATACT TTTTTATTTG TAACCTATAT AGTATAGGAT TTTTTTTGTC ATTTTGTTTC
5461 TTCTCGTACG AGCTTGCTCC TGATCAGCCT ATCTCGCAGC TGATGAATAT CTTGTGGTAG
5521 GGGTTTGGGA AAATCATTCG AGTTTGATGT TTTTCTTGGT ATTTCCCACT CCTCTTCAGA
5581 GTACAGAAGA TTAAGTGAGA CCTTCGTTTG TGCGGATCCC CCACACACCA TAGCTTCAAA
5641 ATGTTTCTAC TCCTTTTTTA CTCTTCCAGA TTTTCTCGGA CTCCGCGCAT CGCCGTACCA
5701 CTTCAAAACA CCCAAGCACA GCATACTAAA TTTCCCCTCT TTCTTCCTCT AGGGTGTCGT
5761 TAATTACCCG TACTAAAGGT TTGGAAAAGA AAAAGAGAC CGCCTCGTTT CTTTTTCTTC
5821 GTCGAAAAAG GCAATAAAAA TTTTTATCAC GTTTCTTTTT CTTGAAAATT TTTTTTTTG
5881 ATTTTTTTCT CTTTCGATGA CCTCCCATTG ATATTTAAGT TAATAAACGG TCTTCAATTT
5941 CTCAAGTTTC AGTTTCATTT TTCTTGTTCT ATTACAACTT TTTTTACTTC TTGCTCATTA
6001 GAAAGAAAGC ATAGCAATCT AATCTAAGGG CGGTGTTGAC AATTAATCAT CGGCATAGTA
6061 TATCGGCATA GTATAATACG ACAAGGTGAG GAACTAAACC ATGGCCAAGC CTTTGTCTCA
6121 AGAAGAATCC ACCCTCATTG AAAGACCAAC GGCTACAATC AACAGCATCC CCATCTCTGA
6181 AGACTACAGC GTCGCCAGCG CAGCTCTCTC TAGCGACCGC CGCATCTTCA CTGGTGTCAA
6241 TGTATATCAT TTTACTGGGG GACCTTGTGC AGAACTCGTG GTGCTGGCCA CTGCTGCTGC
```

TABLE 4-continued

```
6301 TGCGCCAGCT GGCAACCTGA CTTGTATCGT CGCGATCGGA AATGAGAACA GGGGCATCTT
6361 GAGCCCCTGC GGACGGTGCC GACAGGTGCT TCTCGATCTG CATCCTGGGA TCAAAGCCAT
6421 AGTGAAGGAC AGTGATCGAC AGCCGACGGC AGTTGGGATT CGTGAATTGC TGCCCTCTGG
6481 TTATGTGTGG GAGGGCTAAG CACTTCGTGG CCGAGGAGCA GGACTGACAC GTCCGACGCG
6541 GCCCGACGGG TCCGAGGCCT CGGAGATCCG TCCCCCTTTT CCTTTGTCGA Tatcatgtaa
6601 ttagttatgt cgcacttaca ttcgcgccct cccccacat ccgctctaac cgaanaggag
6661 gaagttaaac aacctgaggt ctaggtccct atttattttt ttatagttat attagtatta
6721 agaacgttat ttatatttca gattttctt tttttctgt acagacgcgt gtacgcatgt
6781 aacattatac tgaaaacctt gcttgagaag gttttgggac gctcagaggc tttaatttgc
6841 aagctggagg ccaacatgtg agcaaaaggc cagcaaaagg ccaggaaccg taaaaaggcc
6901 gcgttgctgg cgttttcca taggctccgc cccctgaca agcatcacaa aaatcgacgc
6961 tcaagtcaga ggtggcgaaa cccgacagga ctataagaat accaggcgtt tccccctgga
7021 agctccctcg tgcgctctcc tattccgacc ctgccactta ccggatacct gtccgccttt
7081 ctcccttcgg gaagcgtggc gctttctcaa tgctcacgct gtaggtatct cagttcggtg
7141 taggtcgttc gctccaagct ggactgtgtg cacgaacccc ccgttccgcc cgaccgctgc
7201 gccttatccg gtaactatcg tcttgagtcc aacccggtaa gacacgactt atcgccactg
7261 gcagcagcca ctggtaacag gattagcaga gcgaggtatg taggcggtac tacagagttc
7321 ttgaagtggt ggcctaacta cggctacact agaaggacag tatttggtat ctgcgctctg
7381 ctgaagccag ttaccttcgg aaaaagagtt ggtagctctt gatccggcaa acaaaccacc
7441 actggtagcg gtggtttttt tgtttgcaag cagcagatta cgcgcagaaa aaaaggatct
7501 caagaagatc ctttgatctt ttctacgggg tctgacgctc agtggaacga aaactcacgt
7561 taagggattt tggtcatgag atcagatcta acatccataa tcgtattcgc cgtttctgtc
7621 atttgcgttt tgtacggacc ctcacaacaa ttatcatctc caaaaataga ctatgatcca
7681 ttgacgctcc gatcacttga tttgaagact ttggaagctc cttcacagtt gagtccaggc
7741 accgtagaaa ataatcttCG AAGACAATTG GAGTTTCATT TTCCTTACCG CAGTTACCAA
7801 CCTTTTCCCC AAGATATTTG GCAAACGTGG AAACTTTCTC CCTCTGATAG TTCCTTTCCG
7861 AAAAACTTCA AAGACTTAGG TGAAAGTTGG CTGCAAAGGT CCCCAAATTA TGATCATTTT
7921 GTGATACCCC ATGATGCAGC ATGGGAACTT ATTCACCATC AATACGAACG TGTACCAGAA
7981 GTCTTGGAAG CTTTCCACCT GCTACCAGAC CCGATTCTAA AGGCCGATTT TTTCAGGTAT
8041 TTGATTCTTT TTGCCCGTGG AGGACTGTAT GCTGACATGC ACACTATGTT ATTAAAACCA
8101 ATAGAATCGT GGCTGACTTT CAATGAAACT ATTGGTGGAG TAAAAAACAA TGCTGCGTTC
8161 GTCATTGGTA TTGAGGCTGA TCCTGATAGA CCTGATTGGC ACGACTGGTA TGCTAGAAGG
8221 ATACAATTTT GCGAATGGGC AATTCAGTCC AAACGAGGAC ACCCAGCACT GCGTGAACTG
8281 ATTGTAAGAG TTGTCAGCAC GACTTTACGG AAAGAGAAAA GCGGTTACTT CAACATGGTG
8341 GAAGGAAAGG ATCGTGGAAG TGATGTGATG GACTGGACGG GTCGAGGAAT ATTTACAGAC
8401 ACTCTATTTG ATTATATGAC TAATGTCAAT ACAACAGGCC ACTCAGGCCA ACGAATTGGA
8461 GCTGGCTCAG CGTATTACAA TGCCTTATCG TTGGAAGAAC GTGATGCCCT CTCTGCCCGC
8521 CCGAACGGAG AGATGTTAAA AGAGAAAGTC CCAGGTAAAT ATCCACAGCA GGTTGTTTTA
8581 TGGGAACAAT TTACCAACCT GCGCTCCCCC AAATTAATCG ACGATATTCT TATTCTTCCG
8641 ATCACCAGCT TCAGTCCAGG GATTGGCCAC ACTGGAGCTG ACATTTGAA CCATCACCTT
```

TABLE 4-continued

```
8701  CCATATATTA GGCATACATT TGAAGGAAGT TGGAAGGACT AAAGAAAGCT AGAGTAAAAT
8761  AGATATAGCG AGATTAGAGA ATGAATACCT TCTTCTAAGC GATCGTCCGT CATCATACAA
8821  TATCATGGAC TGTATAGTTT TTTTTTTGTA CATATAATGA TTAAACGGTC ATCCAACATC
8881  TCGTTGACAG ATCTCTCAGT ACGCGAAATC CCTCACTATC AAAGCAAGAA CCGATGAAGA
8941  AAAAACAAC AGTAACCCAA ACACCACAAC AAACACTTTA TCTTCTCCCC CCCAACACCA
9001  ATCATCAAAG AGATGTCGGA ACCAAACACC AAGAAGCAAA AACTAACCCC ATATAAAAAC
9061  ATCCTGGTAG ATAATGCTGG TAACCCGCTG TCCTTCCATA TTCTGGGCTA CTTCACGAAG
9121  TCTGACCGGT CTCAGTTGAT CAACATGATC CTCGAAATGG GTGGCAAGAT CGTTCCAGAC
9181  CTGCCTCCTC TGGTAGATGG AGTGTTGTTT TTGACAGCGG ATTACAAGTC TATTGATCAA
9241  GATACCCTAA AGCAACTGGG GGACGTTCCA ATATACAGAC ACTCCTTCAT CTACCAGTGT
9301  TTTGTGCACA AGACATCTCT TCCCATTGAC ACTTTCCGAA TTGACAAGAA CGTCGACTTG
9361  GCTCAAGATT TGATCAATAG CGCCCTTCAA GAGTCTGTGG ATCATGTCAC TTCTGCCAGC
9421  ACAGCTGCAC CTCCTGCTGT TGTTGTCGCT ACCAACGGCC TGTCTTCTAA ACGAGACGCT
9481  CGTACTAGCA AAATACAGTT CACTCCCGAA GAACATCCTT TTATTCTTCA CTTTGTTAGG
9541  AGAAATCCTA AACCAAGAAA CACACATCAA CTGTACACTG AGCTCGCTCA GCACATGAAA
9601  AACCATACGA ATCATTCTAT CCGCCACAGA TTTCGTCGTA ATCTTTCCGC TCAACTTGAT
9661  TGGGTTTATG ATATCGATCC ATTGACCAAC CAACCTCGAA AAGATGAAAA CGGGAACTAC
9721  ATCAAGGTAC AAGATCTTCC ACAAGGAATT CGTGCTCATT ATTCTCCCCA AGATGATTAC
9781  AATTTGTGTT TATCGGTTCA ACCTTTCATT GAATCTGTAG ATGACACAAC AGGCCAAGAA
9841  TTTTTCAAAC CTCTGAAAGG TGTATTTGAT GACTTGGAAT CTCGCTTTCC TCACCATACA
9901  AAGACTTCCT GGAGAGACAG ATTCAGAAAG TTTGCCTCTA AATACGGTGT TCGTCAGTAC
9961  ATCCCGTATT ATGAAAAGAC TGTTGAACTC AATGGTGTTC CTAATCCGAT GACCAACTTT
10021 ACCTCAAAGG CTTCCATTGA AAAATTTAGA GAAAGACGCC GGACTTCACG TAACACTGGC
10081 CTTGCAGGCC CGGTTGGTGT AGAAGCTGTA AGCTCTTTGG ACCACATATC CCCATTGGTC
10141 ACATCTAATT CCAATTCTCC AGCTGCTCCA CCTGCTGCCG CAGCACTTGC AGCCTCTGCC
10201 TCTGCTTCTT CAGCTCCTAA TACTTCAACT ACCAATTTCT TTGAACAGGA GAATATTGCC
10261 CAAGTGCTCT CTGCACATAA CAACGACCAG TCTATTCCAG AAGTTATTGA GTCCGCACAG
10321 AATGTCAACA CCCATGAAAG TGAACCTATA CCTGATCATG TTCGAAAAAA TCTTACAGAC
10381 GATGAATTGC TTGACAAAAT GGATGATATT TTAAGCTCCA GAACTCTAGG CGGACTAGAT
10441 GACTTGATAA AGATCCTCTA CACTGAGCTG GGATTTGCTC ATCGTTATAC CGAATTTCTT
10501 TTTACCTCAT GTTCTCCTGA TGTGATTTTC TTCCGACCAT TAGTGGAACA TTTCCTTCTT
10561 ACTGGTGAGT CGGAGCTGCA GAATACTCGT GGCATCTGGA CCGCTCGTCA AGACCAAATG
10621 CTACGTGCTA GCAATCTAGA TGACCTGCAC AAGTTAATTG ACCTGCATGG GAAAGAACGT
10681 GTTGAGACCA GAAGAAAAGC CATCAAGGGA GAATGATCAT AAGAAATGAA AAACCTATAA
10741 GT
```

TABLE 5

SEQ ID NO: 54 (top) and SEQ ID NO: 55 (bottom)

AMINO ACID SEQUENCE
MAKADGSLLY YNPHNPPRRY YFYMAIFAVS VICVLYGPSQ

QLSSPKIDYD PLTLRSLDLK TLEAPSQLSP GTVEDNLRRQ

LEFHFPYRSY EPFPQHIWQT WKVSPSDSSF PKNFKDLGES

WLQRSPNYDH FVIPDDAAWE LIHHEYERVP EVLEALDAHR

NAVKVRMEKL GLI

DNA SEQUENCE
ATGGCGAAGG CAGATGGCAG TTTGCTCTAC TATAATCCTC

ACAATCCACC CAGAAGGTAT TACTTCTACA TGGCTATATT

CGCCGTTTCT GTCATTTGCG TTTTGTACGG ACCCTCACAA

CAATTATCAT CTCCAAAAAT AGACTATGAT CCATTGACGC

TCCGATCACT TGATTTGAAG ACTTTGGAAG CTCCTTCACA

GTTGAGTCCA GGCACCGTAG AAGATAATCT TCGAAGACAA

TTGGAGTTTC ATTTTCCTTA CCGCAGTTAC GAACCTTTTC

CCCAACATAT TTGGCAAACG TGGAAAGTTT CTCCCTCTGA

TAGTTCCTTT CCGAAAAACT TCAAAGACTT AGGTGAAAGT

TGGCTGCAAA GGTCCCCAAA TTATGATCAT TTTGTGATAC

CCGATGATGC AGCATGGGAA CTTATTCACC ATGAATACGA

ACGTGTACCA GAAGTCTTGG AAGCTCTAGA TGCTCACCGC

AATGCTGTTA AGGTTCGTAT GGAGAAACTG GGACTTATTT AA.

TABLE 6

SEQ ID NO: 56 (top) and SEQ ID NO: 57 (bottom)

AMINO ACID SEQUENCE
MRSDLTSIIV FAVSVICVLY GPSQQLSSPK IDYDPLTLRS

LDLKTLEAPS QLSPGTVEDN LRRQLEFHFP YRSYEPFPQH

IWQTWKVSPS DSSFPKNFKD LGESWLQRSP NYDHFVIPDD

AAWELIHHEY ERVPEVLEAF HLLPEPILKA DFFRYLILFA

RGGLYADMDT MLLKPIESWL TFNETIGGVK NNAGLVIGIE

ADPDRPDWHD WYARRIQFCQ WAIQSKRGHP ALRELIVRVV

STTLRKEKSG YLNMVEGKDR GSDVMDWTGP GIFTDTLFDY

MTNVNTTGHS GQGIGAGSAY YNALSLEERD ALSARPNGEM

LKEKVPGKYA QQVVLWEQFT NLRSPKLIDD ILILPITSFS

PGIGHSGAGD LNHHLAYIRH TFEGSWKD

DNA SEQUENCE
```
   1 atgagatcag atctaacatc cataatcgta ttcgccgttt
     ctgtcatttg cgttttgtac 61 ggaccctcac aacaattatc atctccaaaa atagactatg
     atccattgac gctccgatca 121 cttgatttga agactttgga agctccttca cagttgagtc
     caggcaccgt agaagataat

181 CTTCGAAGAC AATTGGAGTT TCATTTTCCT TACCGCAGTT
     ACGAACCTTT TCCCCAACAT

241 ATTTGGCAAA CGTGGAAAGT TTCTCCCTCT GATAGTTCCT
     TTCCGAAAAA CTTCAAAGAC

301 TTAGGTGAAA GTTGGCTGCA AAGGTCCCCA AATTATGATC
     ATTTTGTGAT ACCCGATGAT

361 GCAGCATGGG AACTTATTCA CCATGAATAC GAACGTGTAC
     CAGAAGTCTT GGAAGCTTTC

421 CACCTGCTAC CAGAGCCCAT TCTAAAGGCC GATTTTTTCA
     GGTATTTGAT TCTTTTTGCC

481 CGTGGAGGAC TGTATGCTGA CATGGACACT ATGTTATTAA
     AACCAATAGA ATCGTGGCTG

541 ACTTTCAATG AAACTATTGG TGGAGTAAAA ACAATGCTGG
     GGTTGGTCAT TGGTATTGAG

601 GCTGATCCTG ATAGACCTGA TTGGCACGAC TGGTATGCTA
     GAAGGATACA ATTTTGCCAA

661 TGGGCAATTC AGTCCAAACG AGGACACCCA GCACTGCGTG
     AACTGATTGT AAGAGTTGTC

721 AGCACGACTT TACGGAAAGA GAAAAGCGGT TACTTGAACA
     TGGTGGAAGG AAAGGATCGT

781 GGAAGTGATG TGATGGACTG ACGGGTCCA GGAATATTTA
     CAGACACTCT ATTTGATTAT

841 ATGACTAATG TCAATACAAC AGGCCACTCA GGCCAAGGAA
     TTGGAGCTGG CTCAGCGTAT

901 TACAATGCCT TATCGTTGGA AGAACGTGAT GCCCTCTCTG
     CCCGCCCGAA CGGAGAGATG

961 TTAAAAGAGA AAGTCCCAGG TAAATATGCA CAGCAGGTTG
     TTTTATGGGA ACAATTTACC

1021 AACCTGCGCT CCCCCAAATT AATCGACGAT ATTCTTATTC
     TTCCGATCAC CAGCTTCAGT

1081 CCAGGGATTG GCCACAGTGG AGCTGGAGAT TTGAACCATC
     ACCTTGCATA TATTAGGCAT

1141 ACATTTGAAG GAAGTTGGAA GGACTAA.
```

What is claimed is:

1. A method of making recombinant proteins:
expressing a heterologous protein in an engineered strain of *Pichia pastoris* comprising a mutant OCH1 allele which is transcribed into a mRNA coding for a mutant OCH1 protein,
wherein said mutant OCH1 protein comprises a catalytic domain that (i) comprises residues 45-404 of the wild type OCH1 protein of the amino acid sequence of SEQ ID NO 2, or (ii) is at least 90% identical to the amino acids corresponding to residues 45-404 of the wild type OCH1 protein of SEQ ID NO. 2 and has α-1,6-mannosyltransferase activity;
wherein said mutant OCH1 protein lacks an N-terminal sequence for targeting the mutant OCH1 protein to the Golgi apparatus; and
wherein said strain further comprises a nucleic acid coding for and expressing an α-1,2-mannosidase; and
isolating the heterologous protein from the engineered strain, thereby obtaining a preparation of the heterologous protein substantially homogeneous in its N-glycans with Man$_5$GlcNAc2 as the predominant N-glycan form.

2. The method of claim 1, wherein the mutant OCH1 protein lacks a membrane anchor domain at the N-terminal region.

3. The strain of claim 1, wherein said mutant OCH1 protein comprises the amino acid sequence as set forth in SEQ ID NO: 3.

4. The method of claim 1, wherein said mutant OCH1 allele is present on a chromosome.

5. The method of claim 4, wherein said mutant OCH1 allele replaces the wild type OCH1 allele at the OCH1 locus.

6. The method of claim 1, wherein said mutant OCH1 allele is maintained on a plasmid, and wherein the wild type OCH1 allele on the chromosome has been disrupted.

7. The method of claim 1, wherein said nucleic acid coding for and expressing said α-1,2-mannosidase is integrated at the OCH1 locus of the strain.

8. The method of claim 7, wherein said OCH1 locus comprises the nucleotide sequence as set forth in SEQ ID NO: 1.

* * * * *